(12) United States Patent
Saito et al.

(10) Patent No.: US 9,463,451 B2
(45) Date of Patent: Oct. 11, 2016

(54) LIGAND, METAL COMPLEX CONTAINING LIGAND, AND REACTION USING METAL COMPLEX CONTAINING LIGAND

(71) Applicant: National University Corporation Nagoya University, Nagoya-shi (JP)

(72) Inventors: Susumu Saito, Nagoya (JP); Ryoji Noyori, Nagoya (JP); Takashi Miura, Nagoya (JP); Masayuki Naruto, Nagoya (JP); Kazuki Iida, Nagoya (JP); Yuki Takada, Nagoya (JP); Katsuaki Toda, Nagoya (JP); Sota Nimura, Nagoya (JP); Santosh Agrawal, Nagoya (JP); Sunkook Lee, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 14/772,197

(22) PCT Filed: Mar. 4, 2014

(86) PCT No.: PCT/JP2014/055510
§ 371 (c)(1),
(2) Date: Dec. 8, 2015

(87) PCT Pub. No.: WO2014/136795
PCT Pub. Date: Sep. 12, 2014

(65) Prior Publication Data
US 2016/0107151 A1 Apr. 21, 2016

(30) Foreign Application Priority Data
Mar. 4, 2013 (JP) .................................. 2013-042385

(51) Int. Cl.
*C07F 15/00* (2006.01)
*C07F 9/28* (2006.01)
(Continued)

(52) U.S. Cl.
CPC ............ *B01J 31/2414* (2013.01); *B01J 31/24* (2013.01); *C07C 29/132* (2013.01); *C07C 29/145* (2013.01); *C07C 29/149* (2013.01); *C07C 67/28* (2013.01); *C07C 209/50* (2013.01); *C07C 213/00* (2013.01); *C07C 213/02* (2013.01); *C07D 207/33* (2013.01); *C07F 9/582* (2013.01); *C07F 9/6561* (2013.01); *C07F 15/004* (2013.01); *C07F 15/008* (2013.01); *C07F 15/0053* (2013.01); *C07F 15/0066* (2013.01); *C07F 15/0093* (2013.01); *C07F 15/025* (2013.01); *C07F 15/045* (2013.01); *C07F 15/065* (2013.01); *B01J 2231/641* (2013.01); *B01J 2231/76* (2013.01); *B01J 2531/821* (2013.01); *B01J 2531/822* (2013.01); *B01J 2531/827* (2013.01); *B01J 2531/828* (2013.01); *B01J 2531/842* (2013.01); *B01J 2531/845* (2013.01); *B01J 2531/847* (2013.01)

(58) Field of Classification Search
USPC .......................... 546/2, 10, 22, 23; 502/162
See application file for complete search history.

(56) References Cited

U.S. PATENT DOCUMENTS

| 2010/0063294 A1 | 3/2010 | Kuriyama et al. |
| 2012/0253042 A1 | 10/2012 | Milstein et al. |
| 2013/0006020 A1 | 1/2013 | Kuriyama et al. |

FOREIGN PATENT DOCUMENTS

| JP | 2010-215604 A | 9/2010 |
| JP | 2011-037809 A | 2/2011 |
| WO | WO-2012/102247 A1 | 8/2012 |

OTHER PUBLICATIONS

Ziessel, R., "A new family of aromatic polyimine chelates substituted with two diphenylphosphines," Tetrahedron Letters, vol. 30, No. 4, 1989, pp. 463-466.

(Continued)

*Primary Examiner* — Charanjit Aulakh
(74) *Attorney, Agent, or Firm* — Locke Lord LLP; James E. Armstrong, IV; Nicholas J. DiCeglie, Jr.

(57) ABSTRACT

A hydrogen transfer reaction may be more efficiently promoted by using a metal complex represented by Formula (2):

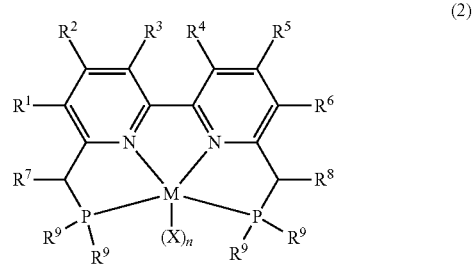

(wherein, $R^1$ to $R^8$ are the same or different, and each represents a hydrogen atom, a substituted or unsubstituted alkyl group or the like; or wherein; $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group;
$R^9$ are the same or different, and each represents an alkyl group or cycloalkyl group;
M is ruthenium (Ru) or the like;
X is a ligand; and
n is 0, 1 or 2).
More specifically, the metal complex enables a hydrogenation reaction of various substrates having a stable carbonyl group or the like to be advanced with a high yield under mild conditions.

10 Claims, 3 Drawing Sheets

(51) Int. Cl.

| | |
|---|---|
| *B01J 31/28* | (2006.01) |
| *B01J 31/24* | (2006.01) |
| *C07C 29/145* | (2006.01) |
| *C07C 29/149* | (2006.01) |
| *C07F 9/6561* | (2006.01) |
| *C07C 209/50* | (2006.01) |
| *C07C 213/02* | (2006.01) |
| *C07F 9/58* | (2006.01) |
| *C07F 15/02* | (2006.01) |
| *C07F 15/04* | (2006.01) |
| *C07F 15/06* | (2006.01) |
| *C07C 29/132* | (2006.01) |
| *C07C 67/28* | (2006.01) |
| *C07C 213/00* | (2006.01) |
| *C07D 207/33* | (2006.01) |

(56) References Cited

OTHER PUBLICATIONS

Langer, R. et al., "Stepwise metal-ligand cooperation by a reversible aromatization/deconjugation sequence in ruthenium complexes with a tetradentate phenanthroline-based ligand," Chemistry—A European Journal, vol. 19, No. 10, 2013, pp. 3407-3414.

Liu, X. et al., "Flexible Redox-Active Binuclear Macrocycles Formed via the Weak-Link Approach and Novel Hemilabile Ligands with N,N,N',N'-Tetramethyl-1,4-phenylenediamine Units," Inorganic Chemistry, vol. 40, No. 13, 2001, pp. 2940-2941.

International Search Report mailed Apr. 8, 2014, issued for PCT/JP2014/055510.

Compound 2c

Compound 2f

Compound 2h

Compound 2i

Compound 2j

LIGAND, METAL COMPLEX CONTAINING LIGAND, AND REACTION USING METAL COMPLEX CONTAINING LIGAND

TECHNICAL FIELD

The present invention relates to a ligand, a metal complex comprising the ligand, and a reaction (specifically, hydrogen transfer reaction) using the metal complex as a catalyst.

BACKGROUND ART

Hydrogen transfer reactions including hydrogenation reactions and dehydrogenation reactions are widely used to synthesize low-molecular and polymeric organic compounds.

However, a catalytic hydrogenation reaction in which hydrogenation (hydrogen reduction) is performed using molecular hydrogen in the presence of a homogeneous catalyst is highly substrate-dependent; thus, significant changes in the central metal or the ligand of the catalyst, the reaction conditions, and the like, according to the type of substrate have been necessary. In particular, hydrogenation reactions with substrates containing ester, amide, carbamate, urea, carboxylic acid, carboxylic acid anhydride, or the like are generally considered difficult because they have a carbonyl group stable (inactive) in the hydrogenation reaction.

A recent report discloses that a ruthenium complex in which two bidentate ligands having a nitrogen atom (N) and a phosphorus atom (P) in the molecule are coordinated with ruthenium (Ru) serves as an effective catalyst for hydrogenation reaction with stable carbonyl groups, such as amide, carbamate, urea, carboxylic acid, or the like (Patent Document 1). However, there has been a demand for a catalyst capable of advancing hydrogen transfer reactions, such as a hydrogenation reaction, of various substrates having a stable carbonyl group with a high yield under milder conditions.

CITATION LIST

Patent Documents

Patent Document 1: International Publication WO2012/102247 pamphlet

SUMMARY OF INVENTION

Technical Problem

An object of the present invention is to provide a metal complex (catalyst) capable of more efficiently promoting hydrogen transfer reactions. More specifically, an object of the present invention is to provide a metal complex (catalyst) capable of advancing hydrogen transfer reactions, such as a hydrogenation reaction (reduction reaction using molecular hydrogen) or a dehydrogenation reaction (oxidation reaction), with various substrates having a stable carbonyl group or the like, with a high yield under mild conditions.

Another object of the present invention is to provide a ligand compound for constituting the metal complex (catalyst).

Still another object of the present invention is to provide a method for producing a hydrogen transfer reaction product (a hydrogenation reaction product, a dehydrogenation reaction product, etc., in particular, a hydrogenation reaction product) using the metal complex (catalyst).

Solution to Problem

The inventors of the present invention conducted extensive research to attain the above objects, and found that a complex formed of ruthenium and a 6,6'-bis(dicyclohexylphosphino)methyl-2,2'-bipyridine, which is a tetradentate ligand, and a complex formed of a similar compound enable hydrogenation of a compound having a stable carbonyl group, such as ester, amide, carbamate, urea, carboxylic acid or the like, with a high yield under mild conditions. The inventors conducted further research based on this finding, and completed the present invention.

Specifically, the present invention provides the following compounds (ligand compounds, metal complexes (catalysts)) and methods for producing a hydrogen transfer reaction product using these metal complexes.

Item 1: A compound (ligand compound) represented by Formula (1a):

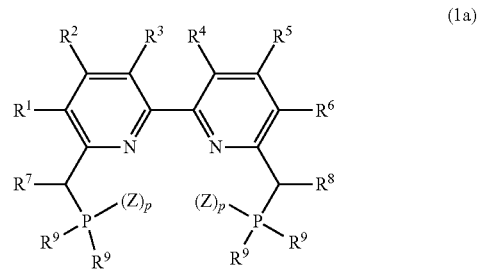

(1a)

wherein $R^1$ to $R^8$ are the same or different, and each represents a hydrogen atom, a substituted or unsubstituted alkyl group, a substituted or unsubstituted alkoxy group, or a substituted or unsubstituted aryl group; or wherein $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group, which may have one or more substituents.

$R^9$ are the same or different, and each represents a substituted or unsubstituted alkyl group, a substituted or unsubstituted cycloalkyl group, or a substituted or unsubstituted aryl group.

Z are the same or different, and each represents a phosphorus atom-protecting group.

p are the same or different, and each represents 0 or 1.

The formula excludes a case where $R^1$, $R^2$, and $R^5$ to $R^8$ are hydrogen atoms, $R^3$ and $R^4$ are bonded to form a group represented by —CH=CH—, and $R^9$ is a t-butyl group.

Item 2: The compound according to Item 1, wherein p is 1 in Formula (1a).

Item 3: The compound according to Item 1 or 2, wherein Z is $BH_3$ in Formula (1a).

Item 4: The compound according to any one of Items 1 to 3, wherein, in Formula (1a), $R^9$ are the same or different, and each represents a linear or branched $C_{1-10}$ alkyl group, a $C_{3-8}$ cycloalkyl group, or a monocyclic or bicyclic aryl group.

Item 5: The compound according to any one of Items 1 to 4, wherein, in Formula (1a), $R^3$ and $R^4$ each represent a hydrogen atom.

Item 6: The compound according to any one of Items 1 to 4, wherein, in Formula (1a), $R^3$ and $R^4$ are bonded to form a group represented by —CH=CH—.

Item 7: The compound according to any one of Items 1 to 6, wherein the compound is used to produce a catalyst for hydrogenation reaction or dehydrogenation reaction.

Item 8: A compound (metal complex) represented by Formula (2a):

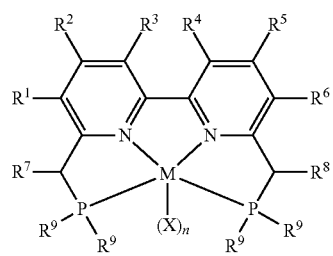

wherein $R^1$ to $R^8$ are the same or different, and each represents a hydrogen atom, a substituted or unsubstituted alkyl group, a substituted or unsubstituted alkoxy group, or a substituted or unsubstituted aryl group; or wherein $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group, which may have one or more substituents.

$R^9$ are the same or different, and each represents a substituted or unsubstituted alkyl group, a substituted or unsubstituted cycloalkyl group, or a substituted or unsubstituted aryl group.

M is ruthenium (Ru), nickel (Ni), cobalt (Co), iron (Fe), rhodium (Rh), iridium (Ir), platinum (Pt), palladium (Pd), gold (Au), or copper (Cu).

X is a ligand.

n is 0, 1 or 2.

The formula excludes a case where $R^1$, $R^2$, and $R^5$ to $R^8$ are hydrogen atoms, $R^3$ and $R^4$ are bonded to form a group represented by —CH=CH—, and $R^9$ is a t-butyl group.

Item 9: The compound according to Item 8, wherein, in Formula (2a), $R^9$ are the same or different, and each represents a linear or branched $C_{1-10}$ alkyl group, a $C_{3-8}$ cycloalkyl group, or a monocyclic or bicyclic aryl group.

Item 10: The compound according to Item 8 or 9, wherein, in Formula (2a), $R^3$ and $R^4$ each represent a hydrogen atom.

Item 11: The compound according to Item 8 or 9, wherein, in Formula (2a), $R^3$ and $R^4$ are bonded to form a group represented by —CH=CH—.

Item 12: The compound according to any one of Items 8 to 11, wherein the compound is a catalyst for hydrogenation reaction or dehydrogenation reaction.

Item 13: A method for producing a hydrogen transfer reaction product, comprising the step of:

subjecting an organic compound to a hydrogenation reaction (reduction reaction using molecular hydrogen) or dehydrogenation reaction (oxidation reaction) in the presence of the compound according to any one of Items 8 to 11.

Item 14: A compound used for producing a catalyst for hydrogenation reaction, represented by Formula (1):

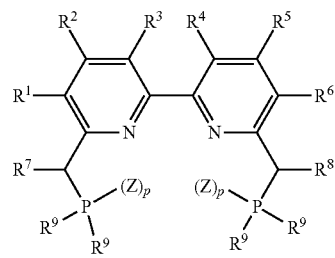

wherein $R^1$ to $R^8$ are the same or different, and each represents a hydrogen atom, a substituted or unsubstituted alkyl group, a substituted or unsubstituted alkoxy group, or a substituted or unsubstituted aryl group; or wherein $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group, which may have one or more substituents.

$R^9$ are the same or different, and each represents a substituted or unsubstituted alkyl group, a substituted or unsubstituted cycloalkyl group, or a substituted or unsubstituted aryl group.

Z are the same or different, and each represents a phosphorus atom-protecting group.

p are the same or different, and each represents 0 or 1.

Item 15: A catalyst for hydrogenation reaction, represented by Formula (2):

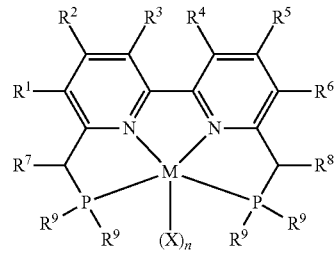

wherein $R^1$ to $R^8$ are the same or different, and each represents a hydrogen atom, a substituted or unsubstituted alkyl group, a substituted or unsubstituted alkoxy group, or a substituted or unsubstituted aryl group; or wherein $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group, which may have one or more substituents.

$R^9$ are the same or different, and each represents a substituted or unsubstituted alkyl group, a substituted or unsubstituted cycloalkyl group, or a substituted or unsubstituted aryl group.

M is ruthenium (Ru), nickel (Ni), cobalt (Co), iron (Fe), rhodium (Rh), iridium (Ir), platinum (Pt), palladium (Pd), gold (Au), or copper (Cu).

X is a ligand.

n is 0, 1 or 2.

Item 16: A method for producing a hydrogen transfer reaction product (a hydrogenation reaction product), comprising the step of:

subjecting an organic compound to a hydrogenation reaction in the presence of the catalyst for hydrogenation reaction according to Item 14 or 15.

ADVANTAGEOUS EFFECTS OF THE INVENTION

The metal complex of the present invention formed of a ligand compound and a metal is capable of efficiently promoting a hydrogen transfer reaction of an organic compound. The metal complex of the present invention has a significantly superior catalytic activity in a hydrogen transfer reaction, compared with the metal complex specifically disclosed in Patent Document 1.

More specifically, by using the metal complex (catalyst) of the present invention, it is possible to perform a hydrogenation reaction (a reduction reaction using molecular hydrogen) of a substrate having a stable carbonyl group, such as ester, carbonate, amide, carbamate, urea, carboxylic acid, carboxylic acid anhydride or the like, with a high yield under milder conditions. Further, by using the metal complex of the present invention, for example, it is possible to perform a dehydrogenation reaction (an oxidation reaction) of alcohols with a high yield under milder conditions, thereby producing a ketone. The present invention is particularly useful in that a hydrogenation reaction (a reduction reaction using molecular hydrogen) can be performed with a high yield under milder conditions even for a compound having a stable (inactive) carbonyl group.

Further, the present invention can simplify the treatment after the hydrogenation, compared with the known hydride reduction reaction using metal hydrides.

In the hydrogen transfer reaction (such as a hydrogenation reaction or a dehydrogenation reaction, in particular, a hydrogenation reaction) using the metal complex (catalyst) of the present invention, it is assumed that the proton is pulled from the ligand of the metal complex by the act of the coexisting base or salt, thereby generating a catalytic active species, thus advancing the reaction. It is assumed that the catalytic active species is further activated by using a tetradentate ligand having two N and two P in the molecule, such as the metal complex (catalyst) of the present invention.

Further, it has also been confirmed that the substituent in the phosphorus (P) of the ligand tends to affect the catalytic activity. Regarding Formula (2), there is a tendency for a metal complex in which $R^9$ bonded to the phosphorus (P) is an isopropyl group, a cyclohexyl group, a phenyl group, or the like to have higher catalytic activity than that of a metal complex in which $R^9$ is a bulky t-butyl group. Although the reason is not clear, it is assumed that, to ensure a high catalytic activity expression, it is important not only that $R^9$ is a bulky group, but also that the carbon atom (C) bonded to the phosphorus (P) is bonded to at least one hydrogen atom (H). However, the hydrogen transfer reaction can be advanced both in the case where the carbon atom (C) bonded to the phosphorus (P) has a hydrogen atom (H) and in the case where the carbon atom (C) bonded to the phosphorus (P) does not have a hydrogen atom (H).

The ligand compound of the present invention is economical because its preparation is very simple. Further, when the ligand compound is protected by a predetermined protecting group (Z), the ligand compound has superior storage stability, and thus can be easily handled.

The metal complex (catalyst) of the present invention is also economical because its preparation is very simple. Further, since it is a stable compound, the metal complex can be easily handled.

DESCRIPTION OF EMBODIMENTS

Figure 1:
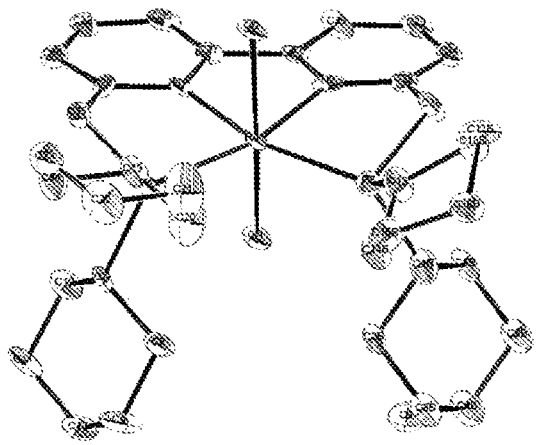
FIG. 1 shows a result of the X-ray single crystal structural analysis of a ruthenium complex (Compound 2c) used in Reaction Example A3 (Oak Ridge Thermal Ellipsoid Plot).

The compounds of the present invention (ligand compounds and metal complexes (catalysts)) and the methods for producing hydrogen transfer reaction products using the metal complexes are described below in detail.

1. Ligand Compound and Metal Complex (1) Ligand Compound

The ligand compound of the present invention is a compound represented by Formula (1):

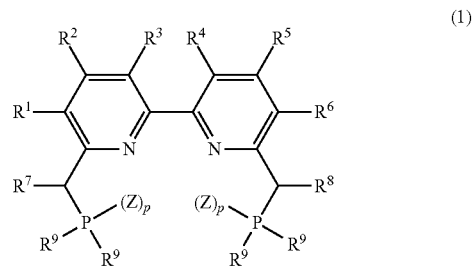

(1)

wherein $R^1$ to $R^8$ are the same or different, and each represents a hydrogen atom, a substituted or unsubstituted alkyl group, a substituted or unsubstituted alkoxy group, or a substituted or unsubstituted aryl group; or wherein $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group, which may have one or more substituents.

$R^9$ are the same or different, and each represents a substituted or unsubstituted alkyl group, a substituted or unsubstituted cycloalkyl group, or a substituted or unsubstituted aryl group.

Z are the same or different, and each represents a phosphorus atom-protecting group.

p are the same or different, and each represents 0 or 1. The ligand compound may form a complex by coordinating with a later-described metal at four bonding sites (two nitrogen atoms and two phosphorus atoms).

Examples of alkyl groups of the substituted or unsubstituted alkyl groups represented by $R^1$ to $R^8$ include linear or branched $C_{1-6}$ alkyl groups, preferably $C_{1-4}$ alkyl groups. More specifically, examples include methyl group, ethyl group, n-propyl group, isopropyl group, n-butyl group, isobutyl group, sec-butyl group, tert-butyl group, pentyl group, and hexyl group. Examples of substituents of the alkyl group include halogen atoms (fluorine atom, chlorine atom, etc.).

Examples of alkoxy groups of the substituted or unsubstituted alkoxy groups represented by $R^1$ to $R^8$ include linear or branched $C_{1-6}$ alkoxy groups, preferably $C_{1-4}$ alkoxy groups. More specifically, examples include methoxy group, ethoxy group, n-propoxy group, and isopropoxy group. Examples of substituents of the alkoxy group include halogen atoms (fluorine atom, chlorine atoms, etc.).

Examples of aryl groups of the substituted or unsubstituted aryl groups represented by $R^1$ to $R^8$ include monocyclic or bicyclic aryl groups. More specifically, examples include phenyl group, toluyl group, xylyl group, and naphthyl group. Examples of substituents of the aryl group include halogen atoms (fluorine atom, chlorine atoms, etc.) and $C_{1-4}$ alkyl groups (methyl group, ethyl group, t-butyl group, etc.).

When $R^1$ and $R^2$, $R^2$ and $R^3$, $R^4$ and $R^5$, and $R^5$ and $R^6$ are respectively bonded to each other to form a bivalent hydrocarbon group, examples of the resulting bivalent hydrocarbon groups include —$(CH_2)_q$— (q is an integer of 2 to 5), —$(CH=CH)_m$— (m is 1, 2 or 3), and —CH=CH—$(CH_2)_r$— (r is an integer of 1 to 3).

The bivalent hydrocarbon group may be substituted, and examples of the substituents include the aforementioned $C_{1-6}$ alkyl groups, the aforementioned aryl groups (such as phenyl group), and oxo groups (=O). The bivalent hydrocarbon group may have 1 or 2 substituents selected from the above groups.

When $R^3$ and $R^4$ are bonded to each other to form a bivalent hydrocarbon group, examples of the bivalent hydrocarbon groups include the group represented by formula: —$(CH_2)_s$— (s is an integer of 1 to 3), the group represented by formula: —CH=CH—, and the group represented by the formula below.

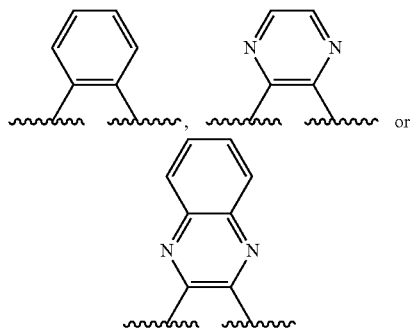

The bivalent hydrocarbon group formed by the bond of $R^3$ and $R^4$ may be substituted, and examples of the substituents include the aforementioned $C_{1-6}$ alkyl groups, and the aforementioned aryl groups (such as phenyl group). The bivalent hydrocarbon group may have 1 or 2 substituents selected from these groups.

The alkyl group of the substituted or unsubstituted alkyl group represented by $R^9$ is, for example a linear or branched $C_{1-10}$ alkyl group, preferably a $C_{1-8}$ alkyl group, and more preferably a $C_{2-6}$ alkyl group. More specifically, examples of the alkyl group include methyl group, ethyl group, n-propyl group, isopropyl group, n-butyl group, isobutyl group, sec-butyl group, tert-butyl group, pentyl group, and hexyl group. Ethyl group, n-propyl group, isopropyl group, n-butyl group, isobutyl group, sec-butyl group or the like is preferable, and isopropyl group, isobutyl group, 3-pentyl group, or the like is more preferable in terms of the yield in the hydrogenation reaction and dehydrogenation reaction using a metal complex having the ligand compound of the present invention as a catalyst. Examples of the substituents of the alkyl group include halogen atoms (fluorine atom, chlorine atom, etc.), alkoxy groups (methoxy group, ethoxy group, etc.), nitro group, amino group, hydroxy group, cyano group, silyl group (trimethylsilyl group, etc.), thiol group, phenyl group, naphthyl group, pyrenyl group, toluyl group, xylyl group, mesityl group, pyridyl group, furyl group, thiophenyl group, and pyrrolyl group.

Examples of the cycloalkyl groups of the substituted or unsubstituted cycloalkyl group represented by $R^9$ include $C_{3-8}$ cycloalkyl groups, such as cyclopropyl group, cyclobutyl group, cyclopentyl group, cyclohexyl group, cycloheptyl group, or cyclooctyl group. Cyclopentyl group and cycloalkyl group are preferable and cyclohexyl group and cyclopentyl group are more preferable in terms of the yield in the hydrogenation reaction and dehydrogenation reaction using a metal complex having the ligand compound of the present invention as a catalyst. Examples of the substituents of the cycloalkyl groups include halogen atoms (fluorine atom, chlorine atom, etc.), alkoxy group (methoxy group, ethoxy group, etc.), nitro group, amino group, hydroxy group, cyano group, silyl group (trimethylsilyl group, etc.), thiol group, phenyl group, naphthyl group, pyrenyl group, toluyl group, xylyl group, mesityl group, pyridyl group, furyl group, thiophenyl group, and pyrrolyl group.

Examples of the aryl groups of the substituted or unsubstituted aryl groups represented by $R^9$ include monocyclic or bicyclic aryl groups. More specifically, examples of the aryl groups include phenyl groups, toluyl groups, xylyl groups, and naphthyl groups. Examples of the substituents of the aryl groups include halogen atoms (fluorine atom, chlorine atom, etc.) and $C_{1-4}$ alkyl groups (methyl group, ethyl group, t-butyl group, etc.).

Examples of the phosphorus atom-protecting group represented by Z includes groups and compounds capable of containing the covalent electron pair in the phosphorus atom and suppressing oxidation of the phosphorus atom. Examples include boron compounds, such as borane ($BH_3$), methyl borane ($MeBH_2$), dimethyl borane ($Me_2BH$), and trifluoro borane ($BF_3$); and aluminum compounds, such as aluminum hydride ($AlH_3$), trimethyl aluminum ($AlMe_3$), triethyl aluminum ($AlEt_3$), tributyl aluminum ($AlBu_3$), or diisobutyl aluminum hydride ($iBu_2AlH$). Boron compounds are preferable in terms of stability, and borane ($BH_3$) is more preferable.

p is 0 or 1. With the aforementioned phosphorus atom-protecting group (p=1), the oxidation of the phosphorus atom of the compound represented by Formula (1) can be suppressed, compared with a compound in which the phosphorus atom is not protected (p=0), thereby stabilizing the compound, thus easing the handling of the compound. However, a compound in which the phosphorus atom is not protected (p=0) is also useful as a precursor to be used immediately before synthesizing the metal complex of the present invention.

Preferable examples of Formula (1) include a compound wherein $R^3$ and $R^4$ are hydrogen atoms.

Other preferable examples of Formula (1) include a compound wherein all of $R^1$, $R^2$, and $R^5$ to $R^8$ are hydrogen atoms.

Other preferable examples of Formula (1) include a compound wherein all of $R^1$ to $R^8$ are hydrogen atoms.

Other preferable examples of Formula (1) include a compound wherein $R^3$ and $R^4$ are bonded to form a group represented by —CH=CH—.

Other preferable examples of Formula (1) include a compound wherein all of $R^1$, $R^2$, and $R^5$ to $R^8$ are hydrogen atoms, and $R^3$ and $R^4$ are bonded to form a group represented by —CH=CH—.

Other preferable examples of Formula (1) include a compound wherein $R^9$ is an alkyl group, cycloalkyl group, or aryl group, and the carbon atom (C) bonded to the phosphorus (P) is bonded to at least one hydrogen atom (H). More specifically, $R^9$ is preferably a linear or branched $C_{1-4}$ alkyl group such as ethyl group, isopropyl group, n-butyl group, isobutyl group, or s-butyl group; $C_{5-7}$ cycloalkyl groups, such as cyclopentyl group, cyclohexyl group, or cyclo heptyl group; and monocyclic or bicyclic aryl groups, such as phenyl group, toluyl group, xylyl group, or naphthyl group. In particular, isopropyl group, cyclohexyl group or phenyl group are preferable.

Among the compounds represented by Formula (1), compounds other than a compound wherein $R^1$, $R^2$, and $R^5$ to $R^8$ are hydrogen atoms, $R^3$ and $R^4$ are bonded to form a group represented by —CH═CH—, and $R^9$ is a t-butyl group are novel compounds. The compounds are represented by Formula (1a). In particular, among the compounds represented by Formula (1), the novel ligand compound represented by Formula (1a) is capable of causing a hydrogen transfer reaction, such as a hydrogenation reaction or dehydrogenation reaction, with a high yield in the synthesis of the metal complex of the present invention.

In terms of the yield in the hydrogenation reaction and dehydrogenation reaction using a metal complex having the ligand compound of the present invention as a catalyst, the ligand compound of the present invention satisfying the above conditions is preferably a compound represented by Formula (1a1):

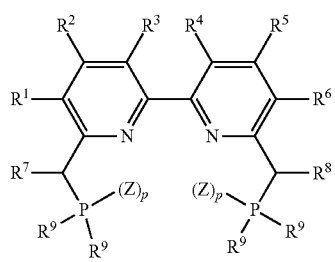

(1a1)

wherein $R^1$ to $R^8$ are the same or different, and each represents a hydrogen atom, a substituted or unsubstituted alkyl group, a substituted or unsubstituted alkoxy group, or a substituted or unsubstituted aryl group; or wherein $R^1$ and $R^2$, $R^2$ and $R^3$, $R^4$ and $R^5$, and $R^5$ and $R^6$ are respectively bonded to each other to form a bivalent hydrocarbon group, which may have one or more substituents.

$R^9$, Z and p are as defined above. The ligand compound of the present invention satisfying the above conditions is more preferably a compound represented by Formula (1a1a):

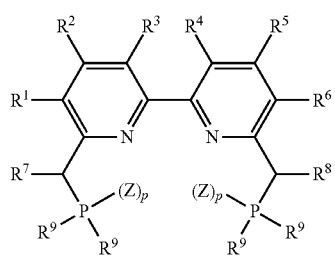

(1a1)

wherein $R^1$ to $R^8$ are the same or different, and each represents a hydrogen atom, a substituted or unsubstituted alkyl group, a substituted or unsubstituted alkoxy group, or a substituted or unsubstituted aryl group.

$R^9$, Z and p are as defined above. The ligand compound of the present invention satisfying the above conditions is further preferably a compound represented by Formula (1a1a1):

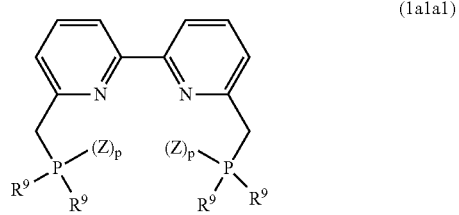

(1a1a1)

wherein, $R^9$, Z and p are as defined above.

Examples of such ligand compounds of the present invention include the compounds below:

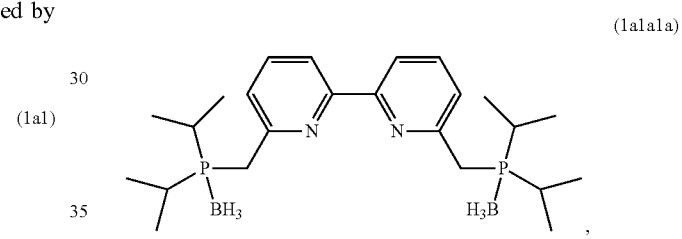

(1a1a1a)

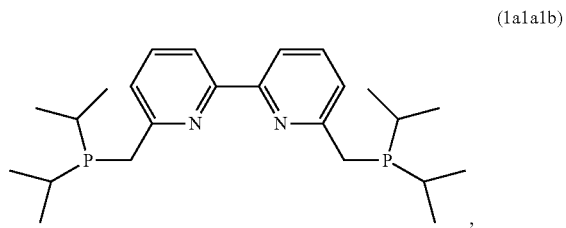

(1a1a1b)

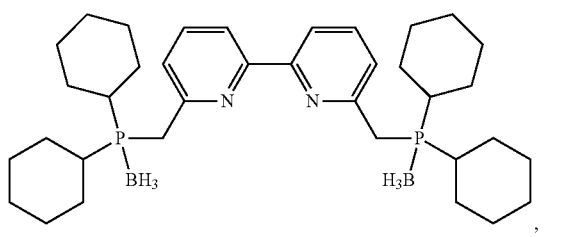

(1a1a1c)

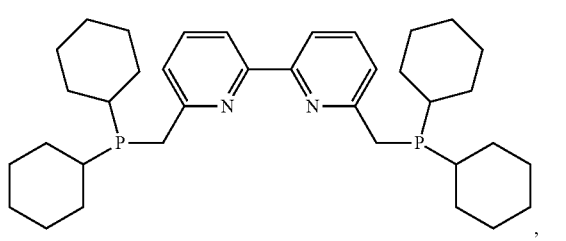

(1a1a1d)

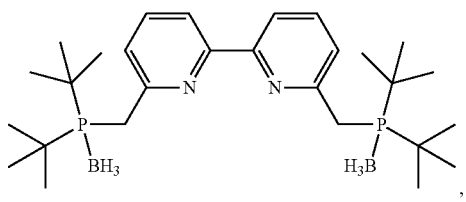
(1a1a1e)

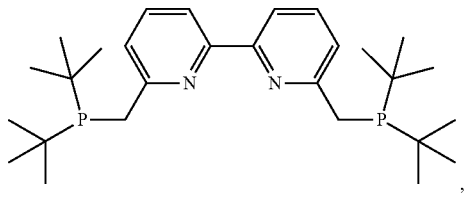
(1a1a1f)

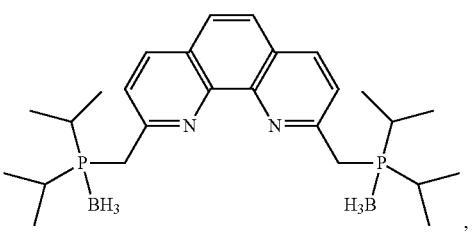
(1a1a2a)

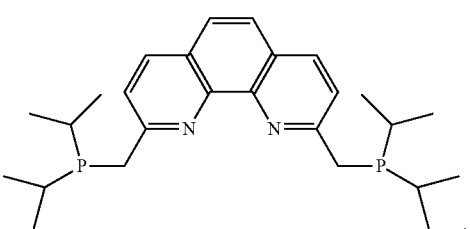
(1a1a2b)

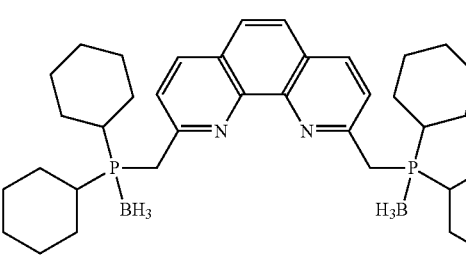
(1a1a2c)

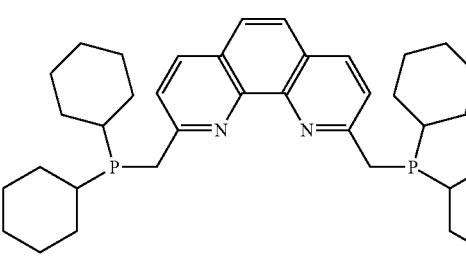
(1a1a2d)

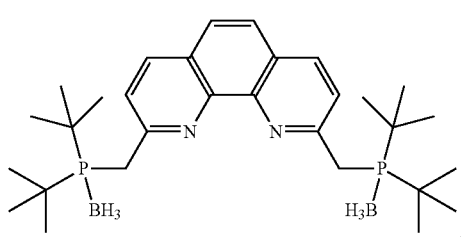
(1a1a2e)

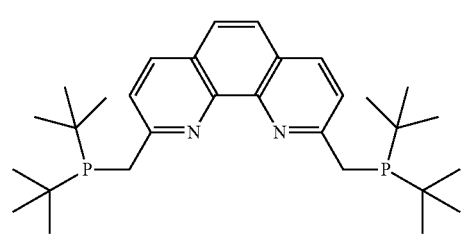
(1a1a2f)

In terms of the yield in the hydrogenation reaction and dehydrogenation reaction using a metal complex having the ligand compound of the present invention as a catalyst, Compounds (1a1a1a), (1a1a1b), (1a1a1c), (1a1a1d), (1a1a1e), and (1a1a1f) and the like are preferable, and Compounds (1a1a1a), (1a1a1b), (1a1a1c), (1a1a1d) and the like are more preferable.

(2) Metal Complex (Catalyst)

The metal complex of the present invention is represented by Formula (2):

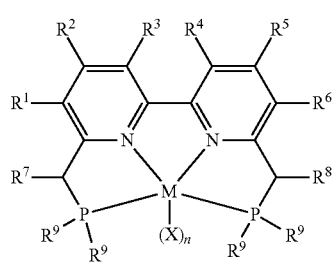
(2)

wherein, $R^1$ to $R^9$ are as defined in Formula (1).

M is ruthenium (Ru), nickel (Ni), cobalt (Co), iron (Fe), rhodium (Rh), iridium (Ir), platinum (Pt), palladium (Pd), gold (Au), or copper (Cu).

X is a ligand.

n is 0, 1 or 2. The metal complex may be used as a catalyst for hydrogen transfer reaction, more specifically a hydrogenation reaction (a reduction reaction using molecular hydrogen) or a dehydrogenation reaction (an oxidation reaction) of organic compounds. In particular, since the metal complex is capable of enabling a reaction with a high yield under milder conditions even when an organic compound having a stable (inactive) carbonyl group is used, the metal complex is particularly useful as a catalyst for a hydrogenation reaction (a reduction reaction using molecular hydrogen).

The same groups as those described in "(1) ligand compound" above may be used as the group represented by $R^1$ to $R^9$.

Preferable metals among the above metals represented by M include Ru, Ni, Co, Fe, Rh, Ir, Pt, and Pd. These metals may have a valence of 1 to 3. In terms of the yield of the hydrogenation reaction and dehydrogenation reaction, M is preferably Ru, Co, Ni, or Ir, more preferably Ru, Co, or Ni, further preferably Ru.

The ligand represented by X is not particularly limited insofar as the ligand can coordinate with the above-described metal (M). Examples of the ligand include hydrogen atom (hydride; H⁻), halogen atom; lower alkoxy groups (for example, $C_{1-3}$ alkoxy groups, etc.); carbon monoxide (CO); boron-based ligand (for example, tetraphenyl borate, tetrakis (bis(trifluoromethyl)phenyl)borate, tetrakis (pentafluorophenyl)borate, tetrafluoro borate, alkyl trifluoro borate, aryl trifluoro borate, etc.); phosphorus-based ligand (for example, hexafluoro phosphate); antimony-based ligand (for example, hexafluoroantimonate, etc.); arsenic-based ligand (for example, hexafluoroarsenate, etc.); sulfonic acid-based ligand (for example, tosylate, mesylate, triflate, etc.); sulfates; perchlorates; nitrates; bis(triflyl)imide; tris(triflyl) methane; bis(triflyl)methane; and carboxylates (for example, acetate, etc.).

Examples of a halogen atom represented by X include a fluorine atom, chlorine atom, bromine atom, and iodine atom.

Preferably, X is a chlorine atom, bromine atom, or the like, and more preferably a chlorine atom.

Examples of lower alkoxy group represented by X include $C_{1-3}$ alkoxy groups or the like, such as a methoxy, ethoxy, n-propoxy, or isopropoxy group.

The ligand represented by X is preferably a halogen atom, more preferably a chlorine atom, bromine atom or the like, and further preferably a chlorine atom.

n may vary depending on the type or the oxidation number of metal (M). n is preferably 1 or 2, and more preferably 2.

The bond of M with nitrogen atoms (N), and the bond of M with phosphorus atoms (P) are generally considered to be coordinate bonds. However, for convenience, these bonds are represented by solid lines in Formula (2).

Among the metal complexes represented by Formula (2), metal complexes other than a compound wherein $R^1$, $R^2$, and $R^5$ to $R^8$ are hydrogen atoms, $R^3$ and $R^4$ are bonded to each other to form a group represented by —CH=CH—, and $R^9$ is a t-butyl group are novel compounds. These compounds are represented by Formula (2a).

The compound represented by Formula (2a) has significantly superior catalytic activity in a hydrogen transfer reaction (a hydrogenation reaction, dehydrogenation reaction, etc.; in particular, a hydrogenation reaction), compared with the compound wherein $R^1$, $R^2$, and $R^5$ to $R^8$ are hydrogen atoms, $R^3$ and $R^4$ are bonded to each other to form a group represented by —CH=CH—, and $R^9$ is a t-butyl group.

In terms of the yield in a hydrogenation reaction and dehydrogenation reaction, the metal complex of the present invention satisfying such conditions is preferably a compound represented by Formula (2a1):

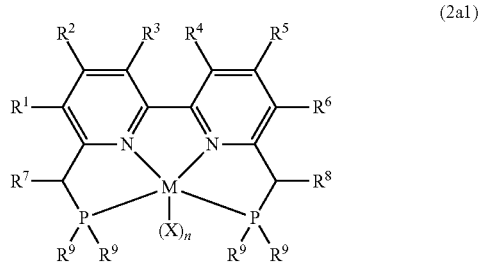

(2a1)

wherein $R^1$ to $R^8$ are the same or different, and each represents a hydrogen atom, a substituted or unsubstituted alkyl group, a substituted or unsubstituted alkoxy group, or a substituted or unsubstituted aryl group; or wherein $R^1$ and $R^2$, $R^2$ and $R^3$, $R^4$ and $R^5$, and $R^5$ and $R^6$ are respectively bonded to each other to form a bivalent hydrocarbon group, which may have one or more substituents.

$R^9$, M, X and n are as defined above. The metal complex of the present invention above is more preferably a compound represented by Formula (2a1a):

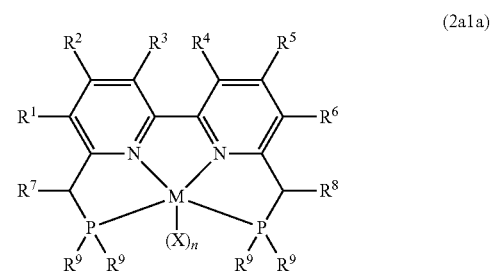

(2a1a)

wherein, $R^1$ to $R^8$ are the same or different, and each represents a hydrogen atom, a substituted or unsubstituted alkyl group, a substituted or unsubstituted alkoxy group, or a substituted or unsubstituted aryl group.

$R^9$, M, X and n are as defined above. The metal complex of the present invention above is further preferably a compound represented by Formula (2a1a1):

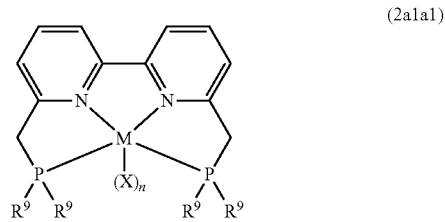

(2a1a1)

wherein, $R^9$, M, X and n are as defined above.

Examples of such metal complexes (catalysts) of the present invention include the compounds below.

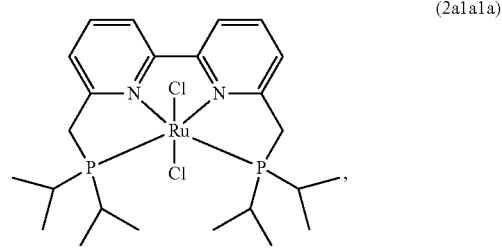

(2a1a1a)

-continued (2a1a1b)
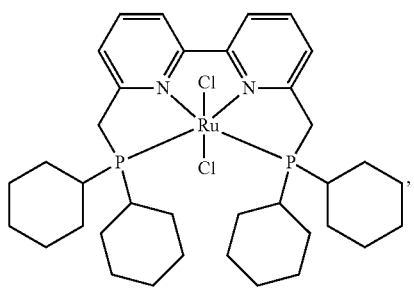

(2a1a1c)
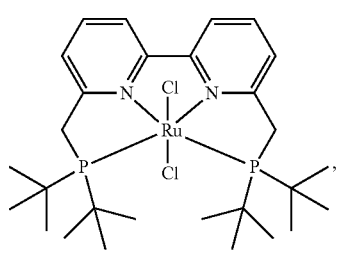

(2a1a2a)
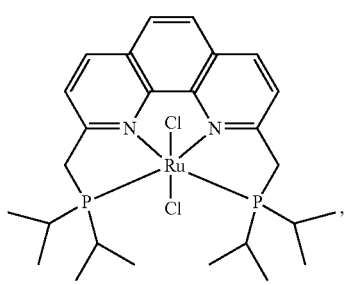

(2a1a2b)
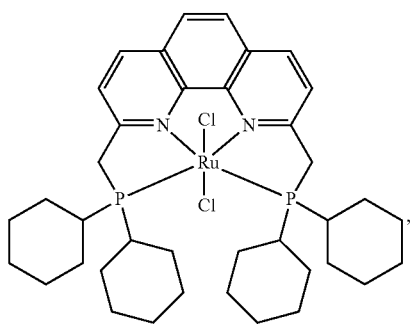

(2a1a2c)
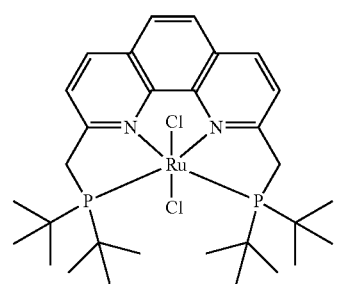

In terms of the yield in a hydrogenation reaction and dehydrogenation reaction, Compounds (2a1a1a), (2a1a1b), (2a1a1c) and the like are preferable, and Compounds (2a1a1a), (2a1a1b) and the like are more preferable.

(3) Method for Producing Ligand Compound and Metal Complex

The ligand compound represented by Formula (1) and the metal complex represented by Formula (2) are produced, for example, through a reaction represented by the following reaction formula:

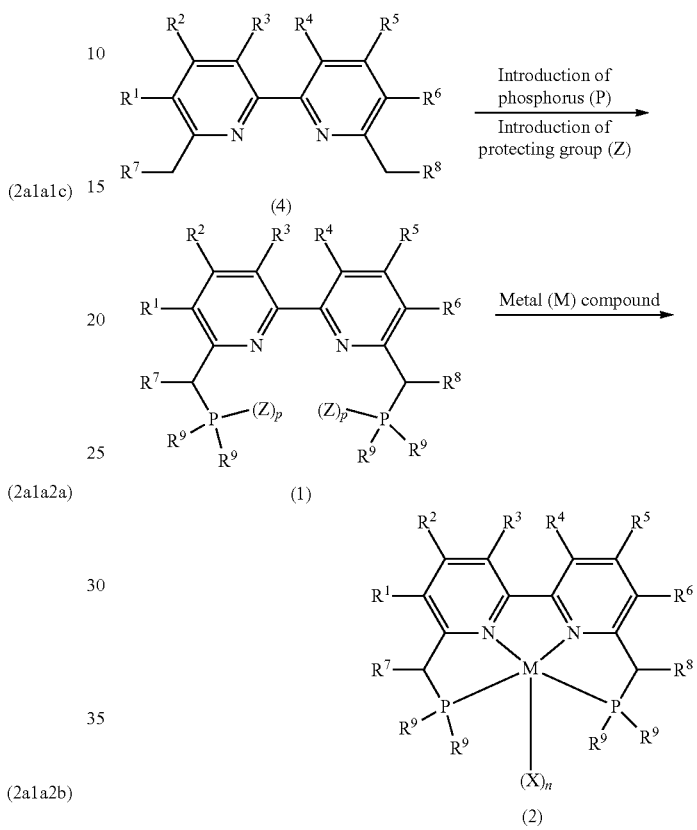

wherein, $R^1$ to $R^9$, Z, p, M, X, and n are as defined above.

Synthesis (4)→(1)

The compound represented by Formula (1) may be produced by reacting the phosphorus compound represented by Formula (5):

$$(R^9)_2P-Y \quad (5)$$

(wherein, Y is a leaving group and $R^9$ is as defined above)

with the compound represented by Formula (4) in the presence of a base, and, as necessary, introducing a protecting group (Z).

Known or commercially available compounds may be used as the compound represented by Formula (4).

Examples of the leaving group represented by Y in Formula (5) include halogen atoms (for example, a chlorine atom, bromine atom, etc.), alkyl sulfonate (for example, methane sulfonate, etc.), haloalkyl sulfonate (for example, trifluoromethane sulfonate, etc.), aryl sulfonate (for example, p-toluene sulfonate, etc.). In terms of the yield in a hydrogenation reaction and a dehydrogenation reaction using the metal complex of the present invention, the leaving group is preferably a halogen atom (in particular, a chlorine atom).

Examples of the base include metal amides, such as lithium diisopropylamide (LDA), lithium bis(trimethylsilyl)amide, sodium bis(trimethylsilyl)amide, or potassium bis(trimethylsilyl)amide (in particular, alkali metal amides);

alkyl lithium, such as methyllithium, ethyllithium, n-butyllithium, s-butyllithium, or t-butyllithium; aryl lithium, such as phenyl lithium; and a Grignard reaction agent. In terms of the yield, the base is preferably LDA, n-butyllithium, t-butyllithium, s-butyllithium, or the like.

Generally, the reaction may be performed in a solvent. Examples of the solvent include ethers, such as diethylether, tetrahydrofuran (THF, hereinafter), dioxane, t-butylmethylether, cyclopentylmethylether, 1,2-dimethoxyethane, or diglyme; aromatic hydrocarbons, such as benzene, toluene, xylene, or mesitylene; and aliphatic hydrocarbons, such as pentane, hexane, heptane, or cyclohexane. These solvents may be used solely or in a combination of two or more.

In terms of the yield, the amount of the base is generally about 2 to 20 mol, and preferably about 3 to 10 mol, per mole of the compound represented by Formula (4).

In terms of the yield, the amount of the phosphorus compound represented by Formula (5) is generally about 2 to 10 mol, preferably about 2 to 5 mol, per mole of the compound represented by Formula (4).

The reaction may be performed by reacting a base with the compound represented by Formula (4) at about −20 to 20° C. (in particular, at about −5 to 5° C.), and adding the phosphorus compound represented by Formula (5) at about 0 to 30° C. This reaction is preferably performed under an anhydrous condition. Further, by introducing a protecting group (Z), such as borane ($BH_3$), into the reaction mixture for the protection of the phosphorus atom, as necessary, it is possible to obtain a ligand compound of the present invention wherein p=1.

The reaction is followed by general isolation and a purification step, thereby obtaining the ligand compound of the present invention represented by Formula (1).
Synthesis of (1)→(2)

By reacting the metal (M) compound with the bisphosphine compound represented by Formula (1) (ligand compound of the present invention), it is possible to produce a metal complex represented by Formula (2) (metal complex of the present invention). When the bisphosphine compound represented by Formula (1) (ligand compound of the present invention) is protected with the protecting group (Z), the above reaction is performed after deprotection.

When the bisphosphine compound represented by Formula (1) (ligand compound of the present invention) is protected with a protecting group, such as borane ($BH_3$), for example, it is possible to perform deprotection of borane by reacting the compound with a deprotection agent.

Examples of deprotection agents include secondary amine compounds such as dimethylamine, diethylamine, diisopropylamine, morpholine, piperidine, or pyrrolidine; and tertiary amine compounds such as triethylamine, tributylamine, 1,4-diazabicyclo[2.2.2]octane(DABCO), or quinuclidine.

A large excess of the deprotection agent relative to the bisphosphine compound represented by Formula (1) (ligand compound of the present invention) may be used. The deprotection reaction may be performed generally under an anhydrous condition and in an inert gas (argon, etc.) atmosphere at about 25 to 160° C. After the reaction, the deprotection agent, such as morpholine, is removed, thereby preparing the bisphosphine compound represented by Formula (1) wherein p=0, i.e., the bisphosphine compound represented by Formula (1) from which a protecting group, such as borane, is removed (ligand compound of the present invention wherein p=0).

After the above reaction, the bisphosphine compound represented by Formula (1) wherein p=0 (ligand compound of the present invention wherein p=0) is isolated, and is then subjected to the subsequent reaction with a metal (M) compound. The bisphosphine compound may be subjected to the reaction with a metal (M) compound without being isolated. The latter case is preferable in terms of preventing oxidation of the bisphosphine compound (ligand compound of the present invention).

Subsequently, a metal (M) compound is reacted with the bisphosphine compound represented by Formula (1) (p=0) (ligand compound of the present invention wherein p=0), thereby obtaining the metal complex represented by Formula (2) (metal complex of the present invention).

The metal (M) compound may be appropriately selected according to the type of metal of the metal complex to be obtained. Examples of the metal (M) compound include dichlorotris(triphenylphosphino)ruthenium(II)($RuCl_2$ $(PPh_3)_3$), $RuCl_3$ hydrate, $RuBr_3$ hydrate, $RuI_3$ hydrate, $RuCl_2(DMSO)_4$, $[Ru(cod)Cl_2]_n$, $[Ru(nbd)Cl_2]_n$, $(cod)Ru(2$-metallyl$)_2$, $[Ru(benzene)Cl_2]_2$, $[Ru(benzene)Br_2]_2$, $[Ru(benzene)I_2]_2$, $[Ru(p$-cymene$)Cl_2]_2$, $[Ru(p$-cymene$) Br_2]_2$, $[Ru(p$-cymene$)I_2]_2$, $[Ru(mesitylene)Cl_2]_2$, $[Ru(mesitylene)Br_2]_2$, $[Ru(mesitylene)I_2]_2$, $[Ru(hexamethylbenzene)Cl_2]_2$, $[Ru(hexamethylbenzene)Br_2]_2$, $[Ru(hexamethylbenzene)I_2]_2$, $RuBr_2(PPh_3)_3$, $RuI_2(PPh_3)_3$, $RuH_4(PPh_3)_3$, $RuH(OAc)(PPh_3)_3$, $RuH_2(PPh_3)_4$ and like ruthenium compounds; $NiCl_2$, $NiF_2$, $NiBr_2$, $NiI_2$, $Ni(BF_4)_2 \cdot 6H_2O$, $Ni(OAc)_2 \cdot 4H_2O$, $Ni(acac)_2$, $NiCl_2(PPh_3)_2$, $NiBr_2(PPh_3)_2$, $NiCl_2(PCy_3)_2$ and like nickel compounds; $CoCl_2$, $CoBr_2$, $CoI_2$, $Co(OAc)_2$, cobalt benzoate(II), cobalt(II)isopropoxide, $Co(acac)_2$ dihydrate, $Co(BF_4)_2 \cdot 6H_2O$, oxalic acid cobalt(II), $CoBr_2(PPh_3)_3$, $CoCl_2(PPh_3)_3$ and like cobalt compounds; $FeCl_2$, $FeF_2$, $FeBr_2$, $FeI_2$ or like inorganic iron compounds or $Fe(OAc)_2$, $Fe(BF_4)_2 \cdot 6H_2O$, $Fe(OTf)_2$, oxalic acid iron(II)dihydrate, $Fe(ClO_4)_2 \cdot 6H_2O$, $Fe(NH_4)_2(SO_4)_2 \cdot 6H_2O$ or like iron compounds; rhodium trichloride.trihydrate($RhCl_3 \cdot 6H_2O$), cyclooctadiene rhodium chloride dimer($[Rh(cod)Cl]_2$), $RhCl(PPh_3)_3$, $RhCl(CO)(PPh_3)_2$, $Rh(cod)_2(BF_4)_2$, $Rh(cod)(CH_3CN)_2(BF_4)_2$, $RhH(CO)(PPh_3)_3$, $RhH(PPh_3)_4$, $Rh(acac)(cod)$, $Rh(acac)(nbd)$ and like rhodium compounds; cyclooctadiene iridium chloride dimer($[Ir(cod)Cl]_2$), bis(cyclooctene)iridium chloride dimer($[IrCl(C_8H_{14})_2]_2$), $IrCl(CO)(PPh_3)_3$, $Ir(cod)_2(BF_4)_2$, $Ir(cod)(acac)$, $Ir(CO)_2(acac)$, $IrH(CO)(PPh_3)_3$ and like iridium compounds; dichloro cyclooctadiene platinum($Pt(cod)Cl_2$), $PtCl_2$, $PtBr_2$, $PtI_2$, $Pt(cod)Br_2$, $Pt(acac)_2$, $PtCl_2(PPh_3)_2$, $PtCl_2(PEt_3)_2$, $Pt(cod)I_2$ and like platinum compounds; dichloro cyclooctadiene palladium($Pd(cod)Cl_2$), $PdCl_2(PPh_3)_2$, $PdCl_2(PCy_3)_2$, $Pd(cod)Cl_2$, $Pd(nbd)Cl_2$, $Pd(OAc)_2$, $PdCl_2(CH_3CN)_2$, allyl palladium chloride dimer($[PdCl(C_3H_5)]_2$) and like palladium compounds; $AuCl$, $AuCl_3$, $AuCl(PtBu_3)$, $AuCl(PEt_3)$, $AuCl(PMe_3)$, $AuCl(PPh_3)$, $Au(CH_3)_2(OAc)$ and like gold compounds; and $CuCl$, $CuCl_2$, $CuBr$, $CuBr_2$, $CuI$, $CuOAc$, $Cu(OAc)_2$, $Cu(acac)_2$, $Cu(PPh_3)_2(NO_3)$ and like copper compounds(in these examples, DMSO represents dimethyl sulfoxide, cod represents 1,5-cyclooctadiene, nbd represents norbornadiene, Ph represents phenyl group, Ac represents acetyl group, acac represents acetylacetonate, Cy group represents cyclohexyl group, Tf represents trifluoromethylsulfonyl group, Et represents ethyl group, tBu represents tert-butyl group, and Me represents methyl group; the same hereinafter).

The amount of metal (M) compound is generally about 0.1 to mol, preferably about 1 to 3 mol, more preferably about 1 to 1.5 mol, per mole of the bisphosphine compound represented by Formula (1) (ligand compound of the present invention).

As necessary, additives, such as metal salts, may be added to stabilize the metal complex. Examples of metal salts include alkali metal lower (in particular $C_{1-4}$)alkoxide, alkali metal tetraphenyl borate, alkali metal tetra fluoro borate, alkali metal tetrakis(bis(trifluoro methyl)phenyl)borate, alkali metal tetrakis(pentafluorophenyl)borate, alkali metal alkyl(in particular $C_{1-4}$ alkyl)trifluoro borate, alkali metal aryl (in particular monocyclic or dicyclic aryl)trifluoro borate, alkali metal hexafluoro phosphate, alkali metal hexafluoroantimonate, alkali metal hexafluoroarsenate, alkali metal tosylate, alkali metal mesylate, alkali metal triflate, alkali metal sulfate, alkali metal perchlorate, alkali metal nitrate, alkali metal bis(triflyl)imide, alkali metal tris(triflyl)methyl, alkali metal bis(triflyl)methyl, and alkali metal carboxylate. Examples of the above alkali metals include lithium, sodium, and potassium.

Further, the alkali metal of the above metal salts may be replaced by silver (i.e., silver salts having the same counter anions as those of the above metal salts) or the like may also be used.

The amount of each additive is generally about 1 to 4 mol, preferably about 1 to 2 mol, per mol of the bisphosphine compound represented by Formula (1) (ligand compound of the present invention).

This reaction may use a solvent. Examples of the solvent include alcohols, such as methanol, ethanol, isopropanol, t-butyl alcohol, or t-amyl alcohol; aromatic hydrocarbons, such as benzene, toluene, xylene, or mesitylene; aliphatic hydrocarbons, such as pentane, hexane, heptane, octane, cyclo pentane, or cyclohexane.

This reaction may be performed generally under an anhydrous condition and in an inert gas (argon, etc.) atmosphere at about to 150° C.

The reaction is followed by general isolation and a purification step, thereby obtaining the metal complex of the present invention represented by Formula (2) (metal complex of the present invention).

2. Hydrogen Transfer Reaction

The metal complex (catalyst) of the present invention is useful as a catalyst for a hydrogen transfer reaction (in particular, a catalyst for a hydrogenation reaction or a dehydrogenation reaction) for efficiently promoting a hydrogen transfer reaction (a hydrogenation reaction or a dehydrogenation reaction). The metal complex (catalyst) of the present invention has high catalytic activity, and therefore enables a hydrogen transfer reaction (both a hydrogenation reaction and a dehydrogenation reaction) with various substrates as raw materials.

(1) Hydrogenation Reaction (Reduction Reaction Using Molecular Hydrogen)

This reaction reacts an organic compound in the presence of the metal complex (catalyst) of the present invention and hydrogen, thereby producing a hydrogenated product (a reduction reaction using molecular hydrogen). More specifically, this reaction enables a reaction of substrates (organic compounds, etc.) in a solvent in the presence of a base or a salt, the metal complex of the present invention, and hydrogen.

Examples of solvents include ethers, such as diethylether, diisopropylether, tetrahydrofuran (THF), dioxane, t-butyl methyl ether, cyclopentyl methyl ether, 1,2-dimethoxyethane, diglyme, or triglyme; aromatic hydrocarbons, such as benzene, toluene, xylene, or mesitylene; aliphatic hydrocarbons, such as pentane, hexane, heptane, cyclo pentane, cyclohexane, octane, nonane, decane, or petroleum ether; and branched-chain $C_{3-6}$ alcohols, such as isopropanol, n-butyl alcohol, t-butyl alcohol, or s-butyl alcohol.

These solvents may be used solely or in a combination of two or more. Among them, aromatic hydrocarbons, such as toluene, xylene, or mesitylene are preferable. These solvents may be used solely or in a combination of two or more.

The amount of the metal complex (catalyst) of the present invention may be appropriately selected according to the type of the substrate (the number of reaction sites, oxidation condition, etc.). For example, the amount is generally about 0.0001 to 0.9 mol, preferably about 0.0005 to 0.5 mol, more preferably about 0.001 to 0.3 mol, and particularly preferably about 0.005 to 0.1 mol, per mole of the substrate.

A base or a salt is used to pull the proton (H) from the metal complex of the present invention, thereby preparing an active species.

Examples of the base include alkali metal hydrides, such as lithium hydride(LiH), or sodium hydride(NaH); alkaline earth metal hydrides, such as calcium hydride($CaH_2$); metal amides (in particular, alkali metal amides), such as lithium diisopropylamide (LDA), lithium bistrimethylsilylamide, sodium bistrimethylsilylamide, or potassium bistrimethylsilylamide; alkyl lithium (in particular, branched C3 or C4 alkyl lithium), such as methyllithium, ethyllithium, n-butyllithium, s-butyllithium, or t-butyllithium; alkali metal alkoxides, such as sodium methoxide, sodium ethoxide, sodium t-butoxide, potassium t-butoxide, lithium t-butoxide, or sodium adamantoxide; alkali metal phenoxide, such as sodium phenoxide; aryl lithium, such as phenyl lithium; and a Grignard reaction agent. Among them, alkali metal hydrides, such as sodium hydride, and alkali metal alkoxides, such as sodium adamantoxide, are preferable in terms of easy handling in air.

Examples of salts include alkali metal lower (in particular $C_{1-4}$)alkoxide, alkali metal tetraphenyl borate, alkali metal tetra fluoro borate, alkali metal tetrakis(bis(trifluoro methyl)phenyl)borate, alkali metal tetrakis(pentafluorophenyl)borate, alkali metal alkyl(in particular $C_{1-4}$alkyl)trifluoro borate, alkali metal aryl (in particular monocyclic or dicyclic aryl)trifluoro borate, alkali metal hexafluoro phosphate, alkali metal hexafluoroantimonate, alkali metal hexafluoroarsenate, alkali metal tosylate, alkali metal mesylate, alkali metal triflate, alkali metal sulfate, alkali metal perchlorate, alkali metal nitrate, alkali metal bis(triflyl)imide, alkali metal tris(triflyl)methyl, alkali metal bis(triflyl)methyl, and alkali metal carboxylate. Examples of the above alkali metals include lithium, sodium, and potassium. Further, silver metal salts in which the alkali metals are replaced by silver (i.e., silver salts having the same counter anions as those of the above metal salts) or the like may also be used.

The amount of the base or salt is generally 1 to 50 mol, preferably 1 to 20 mol, more preferably 2 to 10 mol, per mole of the metal complex (catalyst) of the present invention.

In this reaction, alcohol may be added to promote the hydrogen reduction. Examples of alcohol include methanol, ethanol, n-propanol, isopropanol, n-butyl alcohol, t-butyl alcohol, s-butyl alcohol, and benzyl alcohol. Isopropanol, t-butyl alcohol, s-butyl alcohol, and benzyl alcohol are preferable.

The amount of alcohol is generally about 0.01 to 2 mol, and preferably about 1 to 0.5 mol, per mole of the substrate.

Hydrogen gas may be used as hydrogen, and the hydrogen partial pressure in the reaction is generally about 0.1 to 20 MPa, preferably about 0.5 to 10 MPa, and more preferably about 0.5 to 8 MPa.

The substrate subjected to the reaction is not particularly limited insofar as the substrate has one or more sites that can be reduced by hydrogen in the molecule. Examples of the site that can be reduced by hydrogen include a carbon-carbon unsaturated bond, carbon-nitrogen unsaturated bond, carbon-oxygen unsaturated bond, nitrogen-oxygen unsaturated bond, and sulfur-oxygen unsaturated bond. More specifically, examples include a carbon-carbon double bond, carbon-carbon triple bond, ketone, aldehyde, alkine, ester, lactone, amide, lactam, carbamate, urea, carboxylic acid, carboxylic acid anhydride, nitro group, and cyano group. Examples of the substrates include substrates having at least one of the sites listed above. Examples of the substrate include any linear or branched, or cyclic compounds insofar as the compound has at least one of the above sites.

The reaction of the present invention also has a feature that, generally, the reduction reaction is efficiently advanced with a substrate having a site stable (inactive) to reduction reaction using molecular hydrogen. More specifically, examples of such substrates include substrates with a moiety of ester, lactone, amide, lactam, carbamate, urea, carboxylic acid, carboxylic acid anhydride, quinoline, isoquinoline, indole, benzothiophene, and the like.

When the substrate has a plurality of the sites listed above, it is possible to perform the reduction based on the difference in reactivity by appropriately specifying the reaction conditions, thus selectively reducing sites with high reactivity while leaving the sites with low reactivity.

Further, depending on the oxidation condition of the substrate, it is possible to perform a reduction in stages (decrease the oxidation condition of the substrate in stages) by appropriately specifying the reaction conditions.

Although the reaction temperature and time may vary depending on the type of substrate, the reaction temperature is generally about 0 to 200° C., preferably about 10 to 180° C., and more preferably about 20 to 160° C. The reaction time is generally about 10 minutes to 50 hours, and preferably about 1 to 20 hours. This reaction can generally be performed using an autoclave or the like.

In this reaction, it is possible to react the metal complex of the present invention and a base or salt in the presence or absence of hydrogen, and then react a substrate (an organic compound, etc.) in the presence of hydrogen. Since a catalytic active species with high hydrogenation reduction ability is obtained first by the reaction of the metal complex with a base or salt, by reacting this species with a substrate, it is possible to efficiently obtain a hydrogenation reaction product.

In the reaction of the metal complex with a base or salt, hydrogen pressure is generally about 0 to 50 MPa, preferably about 0.1 to 20 MPa, more preferably about 0.5 to 10 MPa, and further preferably about 0.5 to 8M Pa. The reaction temperature is generally about 0 to 200° C., preferably about 10 to 180° C., and more preferably about 20 to 160° C. The reaction time is generally about 10 minutes to 10 hours, and preferably about 1 to 7 hours.

In the subsequent reaction of the substrate with the catalytic active species thus prepared in the system, the hydrogen pressure is generally about 0.1 to 20 MPa, preferably about 0.5 to 10 MPa, and more preferably about 0.5 to 8 MPa. The reaction temperature is generally about 0 to 200° C., preferably about 10 to 180° C., and more preferably about 20 to 160° C. The reaction time is generally about 10 minutes to 96 hours, and preferably about 1 to 48 hours.

The reaction is followed by general isolation and a purification step, thereby obtaining a hydrogenation reaction product.

(2) Dehydrogenation Reaction (Oxidation Reaction)

This reaction reacts an organic compound in the presence of the metal complex (catalyst) of the present invention, thereby producing a dehydrogenation reaction product (dehydrogenation reaction). More specifically, this reaction enables a reaction of substrates (organic compounds, etc.) in a solvent in the presence of a base or salt, and the metal complex of the present invention (catalyst).

Examples of solvents include ethers, such as diethylether, diisopropylether, tetrahydrofuran (THF), dioxane, t-butyl methyl ether, cyclopentyl methyl ether, 1,2-dimethoxyethane, diglyme, or triglyme; aromatic hydrocarbons, such as benzene, toluene, xylene, or mesitylene; aliphatic hydrocarbons, such as pentane, hexane, heptane, cyclo pentane, cyclohexane, octane, nonane, decane, or petroleum ether; tertiary $C_{4-6}$ alcohols, such as t-butyl alcohol; dimethyl sulfoxide; and amides, such as dimethyl formamide, dimethyl acetamide, or N-methylpyrrolidone. These solvents may be used solely or in a combination of two or more. Among them, aromatic hydrocarbons, such as toluene, xylene, or mesitylene; and ethers such as THF, dioxane, t-butyl methyl ether, or cyclopentyl methyl ether are preferable. These solvents may be used solely or in a combination of two or more.

The amount of the metal complex (catalyst) of the present invention may be appropriately selected according to the type of substrate (the number of reaction sites, oxidation condition, etc.). For example, the amount is generally about 0.0001 to 0.9 mol, preferably about 0.0005 to 0.5 mol, more preferably about 0.001 to 0.3 mol, and particularly preferably about 0.005 to 0.1 mol, per mole of the substrate.

Examples of the base include alkali metal hydrides, such as lithium hydride(LiH), or sodium hydride(NaH); alkaline earth metal hydrides, such as calcium hydride($CaH_2$); metal amides (in particular, alkali metal amides), such as lithium diisopropylamide (LDA), lithium bistrimethylsilylamide, sodium bistrimethylsilylamide, or potassium bistrimethylsilylamide; alkyl lithium (in particular, branched C3 or C4 alkyl lithium), such as methyllithium, ethyllithium, n-butyllithium, s-butyllithium, or t-butyllithium; alkali metal alkoxides, such as sodium methoxide, sodium ethoxide, sodium t-butoxide, potassium t-butoxide, lithium t-butoxide, or sodium adamantoxide; alkali metal phenoxide, such as sodium phenoxide; aryl lithium, such as phenyl lithium; and a Grignard reaction agent. Among them, alkali metal hydrides such as sodium hydride and alkali metal alkoxides (in particular, alkali metal t-butoxide), such as potassium t-butoxide, are preferable in terms of easy handling in air.

Examples of salts include alkali metal lower (in particular $C_{1-4}$) alkoxide, alkali metal tetraphenyl borate, alkali metal tetra fluoro borate, alkali metal tetrakis(bis(trifluoro methyl)phenyl)borate, alkali metal tetrakis(pentafluorophenyl)borate, alkali metal alkyl(in particular $C_{1-4}$alkyl)trifluoro borate, alkali metal aryl (in particular monocyclic or dicyclic aryl)trifluoro borate, alkali metal hexafluoro phosphate, alkali metal hexafluoroantimonate, alkali metal hexafluoroarsenate, alkali metal tosylate, alkali metal mesylate, alkali metal triflate, alkali metal sulfate, alkali metal perchlorate, alkali metal nitrate, alkali metal bis(triflyl)imide, alkali metal tris(triflyl)methyl, alkali metal bis(triflyl)methyl, and alkali metal carboxylate. Examples of the above alkali metals include lithium, sodium, and potassium. Further, the alkali metal of the above metal salts may be replaced by silver (i.e., silver salts having the same counter anions as those of the above metal salts) or the like may also be used.

The amount of the base or salt is generally 1 to 50 mol, preferably 1 to 20 mol, and more preferably 2 to 10 mol, per mole of the metal complex (catalyst) of the present invention.

The substrate subjected to the reaction is not particularly limited insofar as the substrate has at least one site that can be dehydrogenated and oxidized in the molecule. Examples of the sites to be oxidized include primary hydroxyl groups and secondary hydroxyl groups. Examples of the substrates include compounds having at least one of the above sites. Insofar as the compound has at least one of the above sites, the substrate may be a linear, branched, or cyclic compound.

When the substrate has a plurality of the sites listed above, it is possible to perform the dehydrogenation (oxidation) based on the difference in reactivity by appropriately specifying the reaction conditions, thus selectively reducing sites with high reactivity while leaving the sites with low reactivity.

Further, depending on the oxidation condition of the substrate, it is possible to perform dehydrogenation (oxidation) in stages (increase the oxidation condition of the substrate in stages) by appropriately specifying the reaction conditions.

The reaction pressure is generally about 0.05 to 1 MPa, and preferably atmospheric pressure.

Although the reaction temperature and time vary depending on the type of the substrate, the reaction temperature is generally about 0 to 200° C., preferably about 10 to 180° C., and more preferably about 20 to 160° C. The reaction time is generally about 10 minutes to 50 hours, and preferably about 1 to 20 hours. This reaction is generally performed using an autoclave or the like.

This reaction is preferably performed under an anhydrous condition. The reaction may be performed in an inert gas atmosphere or hydrogen atmosphere; however, the reaction is preferably performed in an inert gas (argon, etc.) atmosphere.

In this reaction, it is possible to react the metal complex of the present invention and a base or salt, and then react a substrate (an organic compound, etc.). Since a catalytic active species with high dehydrogenation reduction ability is obtained first by the reaction of the metal complex with a base or salt, by reacting this species with a substrate, it is possible to efficiently obtain a dehydrogenation reaction product.

In the reaction of the metal complex with a base or salt, the reaction pressure is generally about 0.05 to 1 MPa, preferably atmospheric pressure. The reaction temperature is generally about 0 to 200° C., preferably about 10 to 180° C., and more preferably about 20 to 160° C. The reaction time is generally about 10 minutes to 10 hours, and preferably about 1 to 7 hours.

In the subsequent reaction of the substrate with the catalytic active species thus prepared in the system, the reaction pressure is generally about 0.05 to 1 MPa, and preferably atmospheric pressure. The reaction temperature is generally about 0 to 200° C., preferably about 10 to 180° C., and more preferably about 20 to 165° C. The reaction time is generally about 10 minutes to 72 hours, and preferably about 1 to 48 hours.

The reaction is followed by general isolation and a purification step, thereby obtaining a dehydrogenation reaction product.

EXAMPLES

The present invention is explained below in reference to Examples. However, the present invention is not limited to those examples.

A. Ruthenium Complex

Example A1

Synthesis of Compound 2b: RUPIP2

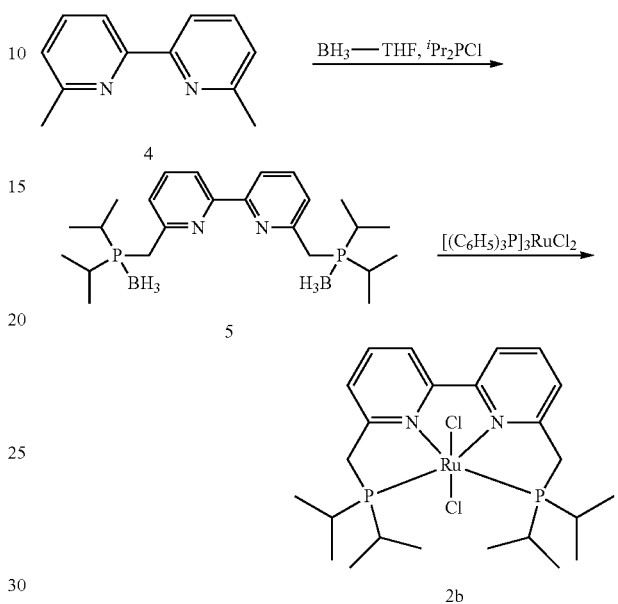

wherein, $^i$Pr represents an isopropyl group; the same hereinafter.

(1) Synthesis of Compound 5

A stirrer, 6,6'-bi-2-picoline (184.2 mg, 1.0 mmol), and THF (10 mL) were placed in a 200-mL double neck flask that had been dried and substituted with argon gas, and the mixture was sufficiently stirred. Thereafter, while stirring, the flask was sufficiently cooled by being immersed in a refrigerant (icy water) at 0° C., thereby obtaining a 6,6'-bi-2-picoline-THF solution.

THF (10 mL) and diisopropylamine (0.85 mL, 6.0 mmol) were placed in a 300-mL double neck flask that had been dried and substituted with argon gas, and the mixture was sufficiently stirred. Thereafter, while stirring, the flask was sufficiently cooled by being immersed in a refrigerant (icy water) at 0° C. A n-butyllithium-hexane solution (4.0-mL, 1.5-M hexane solution, 6.0 mmol) was gradually added dropwise to the solution, thereby causing a reaction. Subsequently, stirring of the reaction solution continued for another 10 minutes while keeping the temperature of the reaction solution at 0° C., thereby obtaining a lithium diisopropylamide-THF solution.

Subsequently, the lithium diisopropylamide-THF solution was added dropwise to the double neck flask containing the 6,6'-bi-2-picoline-THF solution using a cannular, thereby causing a reaction; as a result, a colorless and transparent reaction solution was changed to a bluish-purple solution. While thus adding the lithium diisopropylamide-THF solution dropwise, the temperature inside the flask was kept at 0° C. After the dropwise addition was completed, the flask was taken out of the refrigerant. While stirring of the reaction solution continued, the solution was restored to room temperature (25° C.). After an hour, chlorodiisopropylphosphine (314.6 μL, 2.0 mmol) was added dropwise to the reaction solution, and stirring of the solution continued for another 4 hours. Subsequently, a borane-THF solution (10-mL, 1.0-M THF solution, 10 mmol) was added, and stirring continued overnight. Thereafter, the flask was sufficiently cooled by being immersed in a refrigerant (icy water) at 0° C. After cooling, water was added to the reaction solution, and the whole solution was concentrated by an evaporator. The obtained residue was transferred to a 500-mL separatory funnel, and 100 mL of distilled water, 50 mL of dichloromethane and a small amount of saturated saline were added. This mixture was subjected to separation and extraction five times in total, and the desired organic compound was extracted in the organic layer (dichloromethane layer). The resulting organic layer was dehydrated with sodium sulfate. A filtrate obtained by filtration was concentrated by an evaporator. The concentrated filtrate was then subjected to column chromatography (developing solvent: dichloromethane/hexane=8/1) in which silica gels were shortly accumulated. Subsequently, the resulting dichloromethane/hexane solution containing the resulting purified product was concentrated under reduced pressure (0.1 to 2 mmHg), thereby obtaining 244.3 mg (0.55 mmol) of 6,6'-bis diisopropyl phosphino methyl-2,2'-bipyridine borane complex (Compound 5) as a white powder at an isolation yield of 55%.

The spectral data of Compound 5 is shown below.

$^1$H NMR (600 MHz, CDCl$_3$): δ 8.24 (d, 2H, J=7.6 Hz, C$_{10}$H$_6$N$_2$), 7.76 (t, 2H, J=7.6 Hz, C$_{10}$H$_6$N$_2$), 7.34 (d, 2H, J=7.6 Hz, C$_{10}$H$_6$N$_2$), 3.33 (d, 4H, J=11.0 Hz, PCH$_2$), 2.12-2.23 (m, 4H, CH(CH$_3$)$_2$), 1.17-1.27 (m, 24H, CH(CH$_3$)$_2$), 0.10-0.70 (br, 6H, BH$_3$). $^{13}$C NMR (151 MHz, CDCl$_3$): δ 155.3, 154.2 (d, $^2J_{PC}$=7.2 Hz), 137.3, 124.9, 118.8, 30.6 (d, $J_{PC}$=26.0 Hz), 21.8 (d, $^1J_{PC}$=31.8 Hz), 17.0 (d, 2$J_{PC}$=5.8 Hz). $^{31}$P{$^1$H} NMR (243 MHz, CDCl$_3$): δ36.0, 36.3, HRMS (ESI, (M+H)$^+$) Calcd for C$_{24}$H$_{44}$B$_2$N$_2$P$_2$$^+$: 445.3247. Found m/z=445.3247.

(2) Synthesis of Compound 2b

Compound 5 (300.0 mg, 0.68 mmol) and degassed morpholine (10 mL) were placed in a 100-mL Young-Schlenk container substituted with argon gas. Thereafter, the Young-Schlenk container was placed in an oil bath, and heated to 120° C. while stirring the components in the Young-Schlenk container, thereby causing a reaction. The progress of the reaction was confirmed by thin-layer chromatography (TLC), and the heating was stopped after two hours. Subsequently, the morpholine in the reaction mixture restored to room temperature (25° C.) was removed after collection with a liquid nitrogen trap under reduced pressure (0.1 to 2 mmHg). At this time, the reaction mixture was sufficiently stirred, and the Young-Schlenk container was immersed in water at room temperature (25° C.) to prevent cooling of the Young-Schlenk container by the heat of vaporization.

After sufficiently removing the morpholine, dichlorotris(triphenylphosphino)ruthenium (II) (648.6 mg, 0.68 mmol) and dehydrated toluene (15 mL) were added while introducing argon gas into the container, and the mixture was heated to 110° C. using an oil bath, thereby causing a reaction. The heating was stopped after two hours, and the reaction mixture was restored to room temperature (25° C.).

Subsequently, dehydrated hexane (40 mL) was added to the reaction mixture in an argon gas atmosphere. Thereafter, the whole mixture, including the hexane layer and the toluene layer, in the Young-Schlenk container was stirred and completely mixed.

After leaving the mixture unattended for an hour, the generated purple substance was filtered out in an argon atmosphere while being washed with dehydrated diethylether, thereby obtaining a crude product.

Subsequently, the resulting crude product was subjected to column chromatography (developing solvent: chloroform/ethyl acetate=5/1) in which silica gels are accumulated to about 10 cm, thereby removing a compound with high polarity. The effluent was collected to a flask and the collection was continued until the color of the purple liquid was slightly diluted. After this operation, the solution collected in the recovery flask was rapidly concentrated by an evaporator, thereby obtaining 204.3 mg (0.35 mmol, 51%) of substantially pure Compound 2b (RUPIP2) as a purple substance.

The spectral data of Compound 2b (RUPIP2) is shown below.

$^1$H NMR (600 MHz, CDCl$_3$): δ 7.89 (d, 2H, J=8.3 Hz, C$_{10}$H$_6$N$_2$), 7.69 (t, 2H, J=7.6 Hz, C$_{10}$H$_6$N$_2$), 7.59 (d, 2H, J=8.3 Hz, C$_{10}$H$_6$N$_2$), 3.89 (d, 4H, J=7.6 Hz, PCH$_2$), 2.67-2.78 (m, 4H, CH(CH$_3$)$_2$), 1.35-1.43 (m, 24H, CH(CH$_3$)$_2$). $^{13}$C NMR (151 MHz, CDCl$_3$): δ 163.3, 158.3, 134.4, 121.9, 120.0, 42.1 (d, $^1J_{PC}$=20.2 Hz), 25.4, 20.5, 19.4. $^{31}$P{$^1$H} NMR (243 MHz, CDCl$_3$): δ 60.6. HRMS (ESI, (M-Cl)$^+$) Calcd for C$_{24}$H$_{38}$ClN$_2$P$_2$Ru$^+$: 553.1242. Found m/z=553.1240.

Example A2

Synthesis of Compound 2c: RUPCY2

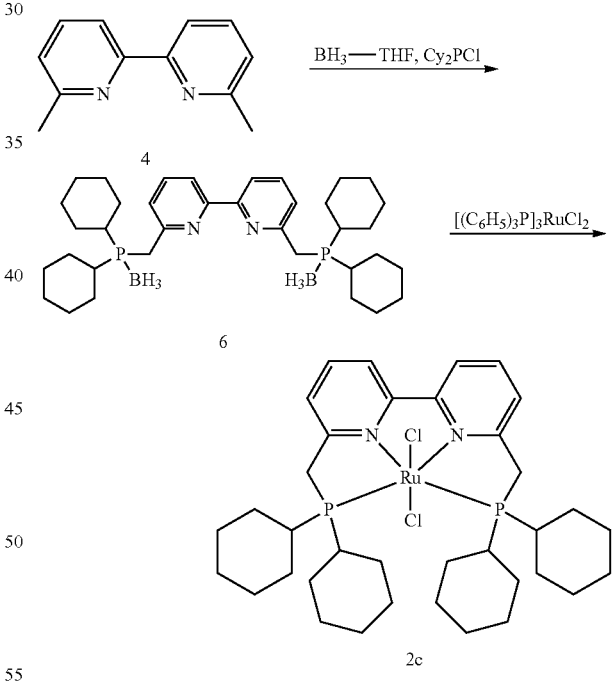

(1) Synthesis of Compound 6

A stirrer, 6,6'-bi-2-picoline (1850.0 mg, 10 mmol) and THF (60 mL) were placed in a 1,000-mL double neck flask that had been dried and substituted with argon gas, and the mixture was sufficiently stirred. Thereafter, while stirring, the flask was sufficiently cooled by being immersed in a refrigerant (icy water) at 0° C., thereby obtaining a 6,6'-bi-2-picoline-THF solution.

THF (30 mL) and diisopropylamine (8.4 mL, 60 mmol) were placed in a 300-mL double neck flask that had been dried and substituted with argon gas, and the mixture was sufficiently stirred. Thereafter, while stirring, the flask was sufficiently cooled by being immersed in a refrigerant (icy water) at 0° C. A n-butyllithium-hexane solution (40-mL, 1.5-M hexane solution, 60 mmol) was gradually added dropwise to the solution, thereby causing a reaction. Subsequently, the stirring of the reaction solution continued for another 10 minutes while keeping the temperature of the reaction solution at 0° C., thereby obtaining a lithium diisopropylamide-THF solution.

Subsequently, the lithium diisopropylamide-THF solution was added dropwise to the double neck flask containing the 6,6'-bi-2-picoline-THF solution using a cannular, thereby causing a reaction; as a result, a colorless and transparent reaction solution was changed to a bluish-purple solution. While thus adding the lithium diisopropylamide-THF solution dropwise, the temperature inside the flask was kept at 0° C. After the dropwise addition was completed, the flask was taken out of the refrigerant. While the stirring of the reaction solution continued, the solution was restored to room temperature (25° C.). After an hour, chlorodicyclohexylphosphine (4.4 mL, 20 mmol) was added dropwise to the reaction solution, and the stirring of the solution continued for another 2 and a half hours. Subsequently, a borane-THF solution (100-mL, 1.0-M THF solution, 100 mmol) was added, and the stirring continued overnight. Thereafter, the flask was sufficiently cooled by being immersed in a refrigerant (icy water) at 0° C. After cooling, water was added to the reaction solution, and the whole solution was concentrated by an evaporator. The obtained residue was transferred to a 1,000-mL separatory funnel, and 100 mL of distilled water, 50 mL of dichloromethane and a small amount of saturated saline were added. This mixture was subjected to separation and extraction four times in total, and the desired organic compound was extracted in the organic layer (dichloromethane layer). The resulting organic layer was dehydrated with sodium sulfate. A filtrate obtained by filtration was concentrated by an evaporator. After the concentration, a small amount of THF was added to the resulting residue to suspend the residue. White powder was obtained by filtration. The white powder was washed with THF several times, thereby obtaining 2,417.6 mg (4.0 mmol) of a 6,6'-bis dicyclohexyl phosphino methyl-2,2'-bipyridine borane complex (Compound 6) as a white powder at an isolation yield of 40%.

The spectral data of Compound 6 is shown below.

$^1$H NMR (600 MHz, CDCl$_3$): δ 8.29 (d, 2H, J=8.3 Hz, C$_{10}$H$_6$N$_2$), 7.75 (t, 2H, J=7.6 Hz, C$_{10}$H$_6$N$_2$), 7.31 (d, 2H, J=7.6 Hz, C$_{10}$H$_6$N$_2$), 3.31 (d, 4H, J=11.0 Hz, PCH$_2$), 1.60-2.00 (m, 24H, C$_6$H$_{11}$), 1.11-1.50 (m, 20H, C$_6$H). $^{13}$C NMR (151 MHz, CDCl$_3$): δ 155.2, 154.5 (d, $^2J_{PC}$=7.2 Hz), 137.2, 125.0, 118.7, 31.5 (d, $^1J_{PC}$=30.3 Hz), 30.5 (d, $^1J_{PC}$=27.5 Hz), 27.01, 26.94, 26.86, 26.75, 26.63, 25.97. $^{31}$P{$^1$H} NMR (243 MHz, CDCl$_3$): δ 28.6, HRMS (ESI, (M+H)$^+$) Calcd for C$_{36}$H$_{60}$B$_2$N$_2$P$_2$$^+$: 605.4502. Found m/z=605.4502.

(2) Synthesis of Compound 2c

Compound 6 (604.4 mg, 1.0 mmol) and degassed morpholine (20 mL) were placed in a 100-mL Young-Schlenk container substituted with argon gas. Thereafter, the Young-Schlenk container was placed in an oil bath, and heated to 120° C. while stirring the components in the Young-Schlenk container, thereby causing a reaction. The progress of the reaction was confirmed by TLC, and the heating was stopped after two hours. Subsequently, the morpholine in the reaction mixture restored to room temperature (25° C.) was removed after collection with a liquid nitrogen trap under reduced pressure (0.1 to 2 mmHg). At this time, the reaction mixture was sufficiently stirred, and the Young-Schlenk container was immersed in water at room temperature (25° C.) to prevent cooling of the Young-Schlenk container by the heat of vaporization.

After sufficiently removing the morpholine, dichlorotris (triphenylphosphino)ruthenium (II) (958.8 mg, 1.0 mmol) and dehydrated toluene (20 mL) were added while introducing argon gas into the container, and the mixture was heated to 110° C. using an oil bath, thereby causing a reaction. The heating was stopped after three hours, and the reaction mixture was restored to room temperature (25° C.).

Subsequently, dehydrated hexane (40 mL) was added to the reaction mixture in an argon gas atmosphere. Thereafter, the whole mixture, including the hexane layer and the toluene layer, in the Young-Schlenk container was stirred and completely mixed. After leaving the mixture unattended for 15 minutes, the generated purple substance was filtered out in an argon atmosphere while being washed with dehydrated diethylether, thereby obtaining a crude product.

Subsequently, the resulting crude product was subjected to column chromatography (developing solvent: chloroform/ethyl acetate=5/1) in which silica gels were accumulated to about 10 cm, thereby removing a compound with high polarity. The effluent was collected to a flask and the collection was continued until the color of the purple liquid was slightly diluted. After this operation, the solution collected in the recovery flask was rapidly concentrated by an evaporator, thereby obtaining 435.1 mg (0.58 mmol, 58%) of substantially pure Compound 2c (RUPCY2) as a purple substance.

The spectral data of Compound 2c (RUPCY2) is shown below.

$^1$H NMR (500 MHz, CDCl$_3$): δ 7.86 (d, 2H, J=7.4 Hz, C$_{10}$H$_6$N$_2$), 7.66 (t, 2H, J=7.5 Hz, C$_{10}$H$_6$N$_2$), 7.56 (d, 2H, J=7.5 Hz, C$_{10}$H$_6$N$_2$), 3.87 (d, 4H, J=8.1 Hz, PCH$_2$), 2.41 (br, 4H, C$_6$H$_{11}$), 2.18 (d, 4H, J=12.1 Hz, C$_6$H$_{11}$), 2.05 (d, 4H, J=10.9 Hz, C$_6$H$_{11}$), 1.54-1.81 (m, 20H, C$_6$H$_{11}$), 1.20-1.34 (m, 20H, C$_6$H$_{11}$). $^{13}$C NMR (150 MHz, CDCl$_3$): δ 163.3, 158.3, 134.1, 122.0, 119.9, 40.5 (d, 1J$_{PC}$=13.0 Hz), 36.3, 30.3, 29.4, 27.7, 27.5, 26.4. $^{31}$P{$^1$H} NMR (241 MHz, CDCl$_3$): δ 54.1. HRMS (ESI, (M-Cl)$^+$) Calcd for C$_{36}$H$_{54}$ClN$_2$P$_2$Ru$^+$: 713.2494. Found m/z=713.2476.

FIG. 1 shows a result of X-ray single crystal structural analysis (Oak Ridge Thermal Ellipsoid Plot) of Compound 2c.

Example A3

Synthesis of Compound 2d: RUPTBU2

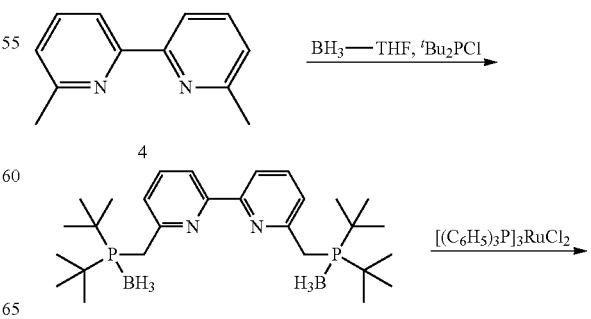

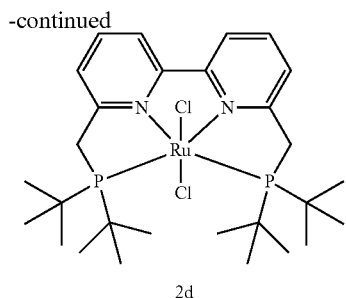

2d

(1) Synthesis of Compound 7

A stirrer, 6,6'-bi-2-picoline (557.6 mg, 3.0 mmol) and THF (30 mL) were placed in a 300-mL double neck flask that had been dried and substituted with argon gas, and the mixture was sufficiently stirred. Thereafter, while stirring, the flask was sufficiently cooled by being immersed in a refrigerant (icy water) at 0° C., thereby obtaining a 6,6'-bi-2-picoline-THF solution.

THF (20 mL) and diisopropylamine (2.52 mL, 18.0 mmol) were placed in a 200-mL double neck flask that had been dried and substituted with argon gas, and the mixture was sufficiently stirred. Thereafter, while stirring, the flask was sufficiently cooled by being immersed in a refrigerant (icy water) at 0° C. A n-butyllithium-hexane solution (12.0-mL, 1.5-M hexane solution, 18.0 mmol) was gradually added dropwise to the solution, thereby causing a reaction. Subsequently, the stirring of the reaction solution continued for another 10 minutes while keeping the temperature of the reaction solution at 0° C., thereby obtaining a lithium diisopropylamide-THF solution.

Subsequently, the lithium diisopropylamide-THF solution was added dropwise to the double neck flask containing the 6,6'-bi-2-picoline-THF solution using a cannular, thereby causing a reaction; as a result, a colorless and transparent reaction solution was changed to a bluish-purple solution. While thus adding the lithium diisopropylamide-THF solution dropwise, the temperature inside the flask was kept at 0° C. After the dropwise addition was completed, the flask was taken out of the refrigerant. While the stirring of the reaction solution continued, the solution was restored to room temperature (25° C.). After an hour, chloro di-t-butyl phosphine (1.20 mL, 6.3 mmol) was added dropwise to the reaction solution, and the stirring of the solution continued for another two hours. Subsequently, a borane-THF solution (35-mL, 1.0-M THF solution, 35 mmol) was added, and the stirring continued overnight. Thereafter, the flask was sufficiently cooled by being immersed in a refrigerant (icy water) at 0° C. After cooling, water was added to the reaction solution, and the whole solution was concentrated by an evaporator. The obtained residue was transferred to a 500-mL separatory funnel, and 100 mL of distilled water, 50 mL of dichloromethane and a small amount of saturated saline were added. This mixture was subjected to separation and extraction five times in total, and the desired organic compound was extracted in the organic layer (dichloromethane layer). The resulting organic layer was dehydrated with sodium sulfate. A filtrate obtained by filtration was concentrated by an evaporator. After the concentration, a small amount of ethyl acetate was added to the resulting residue to suspend the residue. A pale red solid was obtained by filtration. The solid was washed with ethyl acetate several times, thereby obtaining 540 mg (1.08 mmol) of a 6,6'-bis di-t-phosphino methyl-2,2'-bipyridine borane complex (Compound 7) as a pale red powder at an isolation yield of 36%.

The spectral data of Compound 7 is shown below.

$^1$H NMR (600 MHz, CDCl$_3$): δ 8.22 (d, 2H, J=8.3 Hz, C$_{10}$H$_6$N$_2$), 7.73 (t, 2H, J=7.8 Hz, C$_{10}$H$_6$N$_2$), 7.56 (d, 2H, J=7.8 Hz, C$_{10}$H$_6$N$_2$), 3.43 (d, 4H, J=12.0 Hz, PCH$_2$), 1.321 (s, 18H, C(CH$_3$)$_3$), 1.30 (s, 18H, C(CH$_3$)$_3$), 0.20-0.80 (br, 6H, BH$_3$). $^{13}$C NMR (149 MHz, CDCl$_3$): δ 154.9 (d, $^1J_{PC}$=11.3 Hz), 136.8, 125.9, 118.8, 32.8 (d, $^1J_{PC}$=25.6 Hz), 29.4 (d, $^1J_{PC}$=22.9 Hz), 28.2, $^{31}$P{$^1$H} NMR (241 MHz, CDCl$_3$): δ 48.1, 47.8, (ESI, (M+H)$^+$) Calcd for C$_{28}$H$_{52}$B$_2$N$_2$P$_2^+$: 501.3874. Found m/z=501.3869.

(2) Synthesis of Compound 2d

Compound 7 (250.2 mg, 0.50 mmol) and degassed morpholine (10 mL) were placed in a 100-mL Young-Schlenk container substituted with argon gas. Thereafter, the Young-Schlenk container was placed in an oil bath, and heated to 120° C. while stirring the components in the Young-Schlenk container, thereby causing a reaction. The progress of the reaction was confirmed by TLC, and the heating was stopped after two hours. Subsequently, the morpholine in the reaction mixture restored to room temperature (25° C.) was removed after collection with a liquid nitrogen trap under reduced pressure (0.1 to 2 mmHg). At this time, the reaction mixture was sufficiently stirred, and the Young-Schlenk container was immersed in water at room temperature (25° C.) to prevent cooling of the Young-Schlenk container by the heat of vaporization.

After sufficiently removing the morpholine, dichlorotris(triphenylphosphino)ruthenium (II) (479.5 mg, 0.50 mmol) and dehydrated toluene (10 mL) were added while introducing argon gas into the container, and the mixture was heated to 110° C. using an oil bath, thereby causing a reaction. The heating was stopped after five hours, and the reaction mixture was restored to room temperature (25° C.).

Subsequently, dehydrated hexane (40 mL) was added to the reaction mixture in an argon gas atmosphere. Thereafter, the whole mixture, including the hexane layer and the toluene layer, in the Young-Schlenk container was stirred and completely mixed.

After leaving the mixture unattended for an hour, the generated purple substance was filtered out in an argon atmosphere while being washed with dehydrated diethylether, thereby obtaining a crude product.

Subsequently, the resulting crude product was subjected to column chromatography (developing solvent: chloroform/ethyl acetate=5/1) in which silica gels were accumulated to about 10 cm, thereby removing a compound with high polarity. The effluent was collected to a flask and the collection was continued until the color of the purple liquid was slightly diluted. After this operation, the solution collected in the recovery flask was rapidly concentrated by an evaporator, thereby obtaining 64.5 mg (0.1 mmol, 20%) of substantially pure Compound 2d (RUPTBU2) as a purple substance.

The spectral data of Compound 2d (RUPTBU2) is shown below.

$^1$H NMR (600 MHz, CDCl$_3$): δ 7.83 (d, 2H, J=6.8 Hz, C$_{10}$H$_6$N$_2$), 7.58 (t, 2H, J=7.9 Hz, C$_{10}$H$_6$N$_2$), 7.55 (d, 2H, J=7.6 Hz, C$_{10}$H$_6$N$_2$), 3.86 (d, 4H, J=8.3 Hz, PCH$_2$), 1.46 (s, 18H, C(CH$_3$)$_3$), 1.44 (s, 18H, (C(CH$_3$)$_3$). $^{13}$C NMR (151 MHz, CDCl$_3$): δ 166.4, 159.4, 133.9, 122.2, 120.3, 39.1 (d, $^1J_{PC}$=13 Hz), 37.3, 30.6, $^{31}$P{$^1$H} NMR (243 MHz, CDCl$_3$):

Example A4

Synthesis of Compound 2e: RUPIP3

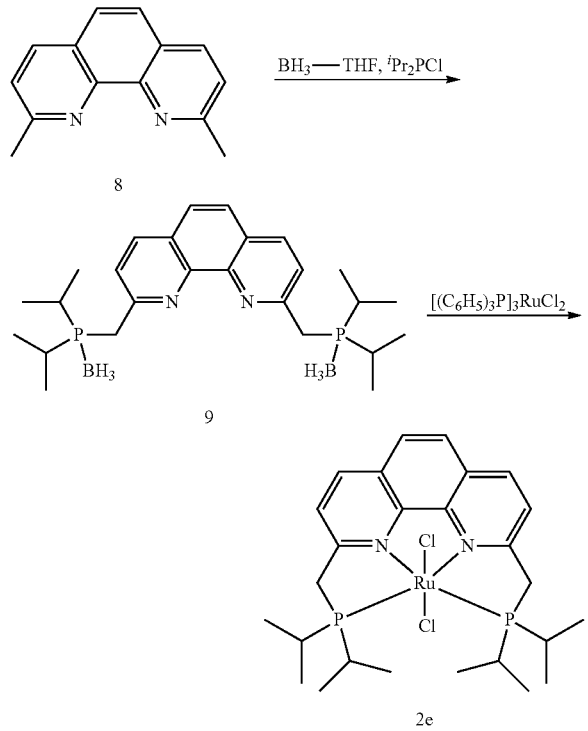

(1) Synthesis of Compound 9

A stirrer, neocuproine 0.5 hydrate (1041.5 mg, 5.0 mmol) and THF (100 mL) were placed in a 1,000 mL double neck flask that had been dried and substituted with argon gas, and the mixture was sufficiently stirred. Thereafter, while stirring, the flask was sufficiently cooled by being immersed in a refrigerant (icy water) at 0° C., thereby obtaining a neocuproine-THF solution.

THF (50 mL) and diisopropylamine (4.2 mL, 30 mmol) were placed in a 300-mL double neck flask that had been dried and substituted with argon gas, and the mixture was sufficiently stirred. Thereafter, while stirring, the flask was sufficiently cooled by being immersed in a refrigerant (icy water) at 0° C. A n-butyllithium-hexane solution (20 mL, 1.5 M hexane solution, 30 mmol) was gradually added dropwise to the solution, thereby causing a reaction. Subsequently, the stirring of the reaction solution continued for another 10 minutes while keeping the temperature of the reaction solution at 0° C., thereby obtaining a lithium diisopropyl-amide-THF solution.

Subsequently, the lithium diisopropylamide-THF solution was added dropwise to the double neck flask containing the neocuproine-THF solution using a cannular, thereby causing a reaction; as a result, a colorless and transparent reaction solution was changed to a bluish-purple solution. While thus adding the lithium diisopropylamide-THF solution dropwise, the temperature inside the flask was kept at 0° C. After the dropwise addition was completed, the flask was taken out of the refrigerant. While the stirring of the reaction solution continued, the solution was restored to room temperature (25° C.). After an hour, chlorodiisopropylphosphine (1.59 mL, 10 mmol) was added dropwise to the reaction solution, and the stirring of the solution continued overnight. Subsequently, a borane-THF solution (50 mL, 1.0 M THF solution, 50 mmol) was added, and the stirring continued overnight. Thereafter, the flask was sufficiently cooled by being immersed in a refrigerant (icy water) at 0° C. After cooling, water was added to the reaction solution, and the whole solution was concentrated by an evaporator. The obtained residue was transferred to a 1,000-mL separatory funnel, and 100 mL of distilled water, 50 mL of dichloromethane and a small amount of saturated saline were added. This mixture was subjected to separation and extraction five times in total, and the desired organic compound was extracted in the organic layer (dichloromethane layer). The resulting organic layer was dehydrated with sodium sulfate. A filtrate obtained by filtration was concentrated by an evaporator. The concentrated filtrate was then subjected to column chromatography (developing solvent: chloroform/ethyl acetate/hexane=1/1/3) in which silica gels were shortly accumulated. Subsequently, a chloroform/ethyl acetate/hexane solution containing the resulting purified product was concentrated under reduced pressure (0.1 to 2 mmHg), thereby obtaining 1,248 mg (2.7 mmol) of a 2,9-bis diisopropyl phosphino methyl-1,10-phenanthroline borane complex (Compound 9) as a pale yellow powder at an isolation yield of 53%.

The spectral data of Compound 9 is shown below.

$^1$H NMR (600 MHz, CDCl$_3$): δ 8.19 (d, 2H, J=8.3 Hz, C$_{12}$H$_6$N$_2$), 7.76 (d, 2H, J=7.6 Hz, C$_{12}$H$_6$N$_2$), 7.76 (s, 2H, C$_{12}$H$_6$N$_2$), 3.63 (d, 4H, J=11.7 Hz, PCH$_2$), 2.18-2.26 (m, 4H, CH(CH$_3$)$_2$), 1.16-1.24 (m, 24H, CH(CH$_3$)$_2$). $^{13}$C NMR (151 MHz, CDCl$_3$): δ 155.3 (d, $^2J_{PC}$=4.3 Hz), 145.3, 136.2, 127.5, 126.1, 124.7, 31.9 (d, $^1J_{PC}$=24.6 Hz), 22.2 (d, $^1J_{PC}$=31.8 Hz), 17.1 (d, $^2J_{PC}$=4.3 Hz). $^{31}$P{$^1$H} NMR (243 MHz, CDCl$_3$): δ36.2, 36.4. (ESI, (M+H)$^+$) Calcd for C$_{26}$H$_{44}$B$_2$N$_2$P$_2$$^+$: 469.3247. Found m/z=469.3235.

(2) Synthesis of Compound 2e

Compound 9 (362.2 mg, 0.77 mmol) and degassed morpholine (15 mL) were placed in a 100-mL Young-Schlenk container substituted with argon gas. Thereafter, the Young-Schlenk container was placed in an oil bath, and heated to 120° C. while stirring the components in the Young-Schlenk container, thereby causing a reaction. The progress of the reaction was confirmed by TLC, and the heating was stopped after two hours. Subsequently, the morpholine in the reaction mixture restored to room temperature (25° C.) was removed after collection with a liquid nitrogen trap under reduced pressure (0.1 to 2 mmHg). At this time, the reaction mixture was sufficiently stirred, and the Young-Schlenk container was immersed in water at room temperature (25° C.) to prevent cooling of the Young-Schlenk container by the heat of vaporization.

After sufficiently removing the morpholine, dichlorotris(triphenylphosphino)ruthenium (II) (738.2 mg, 0.77 mmol) and dehydrated toluene (15 mL) were added while introducing argon gas into the container, and the mixture was heated to 110° C. using an oil bath, thereby causing a reaction overnight. Thereafter, the heating was stopped, and the reaction mixture was restored to room temperature (25° C.).

Subsequently, dehydrated hexane (40 mL) was added to the reaction mixture in an argon gas atmosphere. Thereafter, the whole mixture, including the hexane layer and the toluene layer, in the Young-Schlenk container was stirred and completely mixed. After leaving the mixture unattended (δ 66.8, HRMS (FAB, M$^+$) Calcd for C$_{28}$H$_{46}$Cl$_2$N$_2$P$_2$Ru$^+$: 644.1557. Found m/z=644.1344.)

for an hour, the generated purple substance was filtered out in an argon atmosphere while being washed with dehydrated diethylether, thereby obtaining a crude product.

Subsequently, the resulting crude product was subjected to column chromatography (developing solvent: chloroform/acetone=3/1) in which silica gels were accumulated to about 10 cm, thereby removing a compound with high polarity. The effluent was collected to a flask and the collection was continued until the color of the purple liquid was slightly diluted. After this operation, the solution collected in the recovery flask was rapidly concentrated by an evaporator, thereby obtaining 180.4 mg (0.29 mmol, 38%) of substantially pure Compound 2e (RUPIP3) as a purple substance.

The spectral data of Compound 2e (RUPIP3) is shown below.

$^1$H NMR (600 MHz, CDCl$_3$): δ 8.13 (d, 2H, J=8.3 Hz, C$_{12}$H$_6$N$_2$), 7.88 (d, 2H, J=8.3 Hz, C$_{12}$H$_6$N$_2$), 7.81 (s, 2H, C$_{12}$H$_6$N$_2$), 4.07 (d, 4H, J=8.2 Hz, PCH$_2$), 2.75-2.85 (m, 4H, CH(CH$_3$)$_2$), 1.38-1.52 (CH(CH$_3$)$_2$). $^{13}$C NMR (151 MHz, CDCl$_3$): δ 163.6, 149.3, 132.9, 128.7, 125.4, 121.7 (d, J$_{PC}$=5.8 Hz), 43.0 (d, $^1$J$_{PC}$=24.6 Hz), 25.6 (t, $^1$J$_{PC}$=7.2 Hz), 20.9, 19.4. $^{31}$P{$^1$H} NMR (202 MHz, CDCl$_3$): δ 62.9. HRMS (ESI, (M-Cl)$^+$) Calcd for C$_{26}$H$_{38}$ClN$_2$P$_2$Ru$^+$: 577.1242. Found m/z=577.1210.

Example A5

Synthesis of Compound 2f: RUPCY3

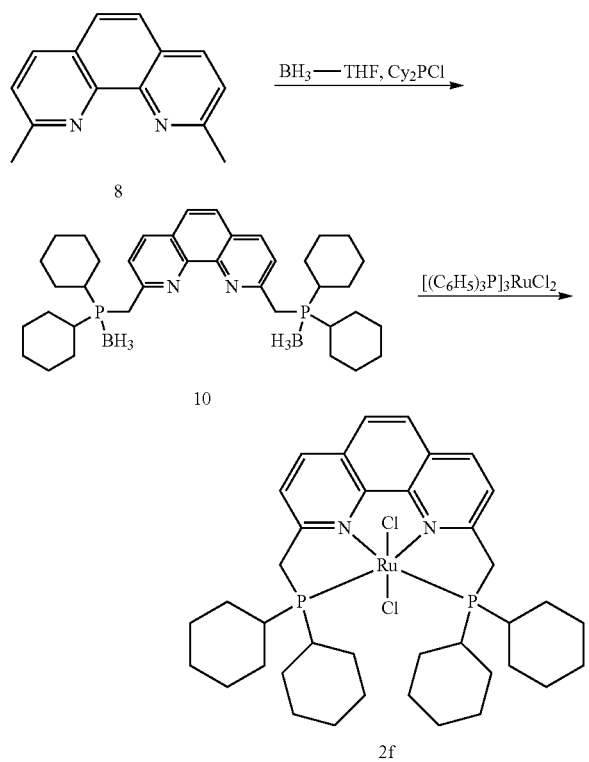

(1) Synthesis of Compound 10

A stirrer, neocuproine 0.5 hydrate (1041.5 mg, 5.0 mmol) and THF (100 mL) were placed in a 1,000-mL double neck flask that had been dried and substituted with argon gas, and the mixture was sufficiently stirred. Thereafter, while stirring, the flask was sufficiently cooled by being immersed in a refrigerant (icy water) at 0° C., thereby obtaining a neocuproine-THF solution.

THF (50 mL) and diisopropylamine (4.2 mL, 30 mmol) were placed in a 300-mL double neck flask that had been dried and substituted with argon gas, and the mixture was sufficiently stirred. Thereafter, while stirring, the flask was sufficiently cooled by being immersed in a refrigerant (icy water) at 0° C. A n-butyllithium-hexane solution (20-mL, 1.5-M hexane solution, 30 mmol) was gradually added dropwise to the solution, thereby causing a reaction. Subsequently, the stirring of the reaction solution continued for another 10 minutes while keeping the temperature of the reaction solution at 0° C., thereby obtaining a lithium diisopropylamide-THF solution.

Subsequently, the lithium diisopropylamide-THF solution was added dropwise to the double neck flask containing the neocuproine-THF solution using a cannular, thereby causing a reaction. As a result, a colorless and transparent reaction solution was changed to a reddish brown solution. While thus adding the lithium diisopropylamide-THF solution dropwise, the temperature inside the flask was kept at 0° C. After the dropwise addition was completed, the flask was taken out of the refrigerant. While the stirring of the reaction solution continued, the solution was restored to room temperature (25° C.). After an hour, chloro dicyclohexyl phosphine (2.2 mL, 10 mmol) was added dropwise to the reaction solution, and the stirring of the solution continued overnight. Subsequently, a borane-THF solution (50-mL, 1.0-M THF solution, 50 mmol) was added, and the stirring continued overnight. Thereafter, the flask was sufficiently cooled by being immersed in a refrigerant (icy water) at 0° C. After cooling, water was added to the reaction solution, and the whole solution was concentrated by an evaporator. The obtained residue was transferred to a 1,000-mL separatory funnel, and 100 mL of distilled water, 50 mL of dichloromethane and a small amount of saturated saline were added. This mixture was subjected to separation and extraction five times in total, and the desired organic compound was extracted in the organic layer (dichloromethane layer). The resulting organic layer was dehydrated with sodium sulfate. A filtrate obtained by filtration was concentrated by an evaporator. After the concentration, a small amount of ethyl acetate was added to the resulting residue to suspend the residue. A pale red powder was obtained by filtration. The powder was washed with acetone several times, thereby obtaining 1,580.0 mg (2.5 mmol) of a 2,9-bis dicyclohexyl phosphino methyl-1,10-phenanthroline borane complex (Compound 10) as a pale red powder at an isolation yield of 50%.

The spectral data of Compound 10 is shown below.

$^1$H NMR (600 MHz, CDCl$_3$): δ 8.16 (d, 2H, J=8.3 Hz, C$_{12}$H$_6$N$_2$), 7.75 (s, 2H, C$_{12}$H$_6$N$_2$), 7.7 (d, 2H, J=8.3 Hz, C$_{12}$H$_6$N$_2$), 3.57 (d, 4H, J=11.3 Hz, PCH$_2$), 1.60-2.03 (m, 24H, C$_6$H$_{11}$), 1.13-1.57 (m, 20H, C$_6$H$_{11}$) $^{13}$C NMR (149 MHz, CDCl$_3$): δ 155.3 (d, $^1$J$_{PC}$=5.8 Hz), 145.5, 136.0, 127.4, 126.1, 124.6, 31.9 (d, $^1$J$_{PC}$=31.8 Hz), 31.5 (d, $^1$J$_{PC}$=26.1 Hz), 27.13, 27.05, 27.02, 26.94, 26.81, 26.64, 25.9. $^{31}$P{$^1$H} NMR (243 MHz, CDCl$_3$): δ 28.5, (ESI, (M+H)$^+$) Calcd for C$_{38}$H$_{60}$B$_2$N$_2$P$_2$$^+$: 629.4503. Found m/z=629.4503.

(2) Synthesis of Compound 2f

Compound 10 (628.5 mg, 1.0 mmol) and degassed morpholine (15 mL) were placed in a 100-mL Young-Schlenk container substituted with argon gas. Thereafter, the Young-Schlenk container was placed in an oil bath, and heated to 120° C. while stirring the components in the Young-Schlenk container, thereby causing a reaction. The progress of the reaction was confirmed by TLC, and the heating was stopped after two hours. Subsequently, the morpholine in the reaction mixture restored to room temperature (25° C.) was removed after collection with a liquid nitrogen trap under reduced pressure (0.1 to 2 mmHg). At this time, the reaction mixture was sufficiently stirred, and the Young-Schlenk container was immersed in water at room temperature (25° C.) to prevent cooling of the Young-Schlenk container by the heat of vaporization.

After sufficiently removing the morpholine, dichlorotris (triphenylphosphino)ruthenium (II) (958.8 mg, 1.0 mmol) and dehydrated toluene (20 mL) were added while introducing argon gas into the container, and the mixture was heated to 110° C. using an oil bath, thereby causing a reaction. The heating was stopped after two hours, and the reaction mixture was restored to room temperature (25° C.).

Subsequently, dehydrated hexane (40 mL) was added to the reaction mixture in an argon gas atmosphere. Thereafter, the whole mixture, including the hexane layer and the toluene layer, in the Young-Schlenk container was stirred and completely mixed. After leaving the mixture unattended for an hour, the generated purple substance was filtered out in an argon atmosphere while being washed with dehydrated diethylether, thereby obtaining a crude product.

Subsequently, the resulting crude product was subjected to column chromatography (developing solvent: chloroform/THF=10/1) in which silica gels were accumulated to about 10 cm, thereby removing a compound with high polarity. The effluent was collected to a flask and the collection was continued until the color of the purple liquid was slightly diluted. After this operation, the solution collected in the recovery flask was rapidly concentrated by an evaporator, thereby obtaining 563.7 mg (0.73 mmol, 73%) of substantially pure Compound 2f (RUPCY3) as a purple substance.

The spectral data of Compound 2f (RUPCY3) is shown below.

$^1$H NMR (600 MHz, CDCl$_3$): δ 8.12 (d, 2H, J=8.2 Hz, C$_{12}$H$_6$N$_2$), 7.86 (d, 2H, J=8.2 Hz, C$_{12}$H$_6$N$_2$), 7.80 (s, 2H, C$_{12}$H$_6$N$_2$), 4.05 (d, 4H, J 35=7.6 Hz, PCH$_2$), 2.42-2.51 (br, 4H, C$_6$H$_{11}$), 2.31 (d, 4H, J=11.0 Hz C$_6$H$_{11}$), 2.12 (d, 4H, J=12.4 Hz, C$_6$H$_{11}$), 1.61-1.94 (m, 20H, C$_6$H$_{11}$), 1.18-1.37 (m, 12H, C$_6$H$_{11}$). $^{13}$C NMR (151 MHz, CDCl$_3$): δ 163.6, 149.3, 132.6, 128.6, 125.3, 121.8, 41.4, (d, $^1J_{PC}$=23.1 Hz) 36.6 (t, $^1J_{PC}$=7.2 Hz), 30.7, 29.4, 27.8, 27.6, 26.4. $^{31}$P{$^1$H} NMR (243 MHz, CDCl$_3$): δ 56.8. HRMS (ESI, (M-Cl)$^+$) Calcd for C$_{38}$H$_{54}$ClN$_2$P$_2$Ru$^+$: 737.2494. Found m/z=737.2483.

Figure 2:
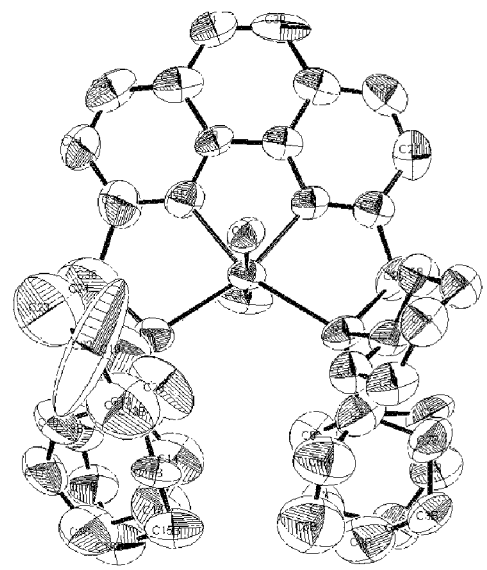
FIG. 2 shows a result of the X-ray single crystal structural analysis of a ruthenium complex (Compound 2f) used in Reaction Example A3 (Oak Ridge Thermal Ellipsoid Plot).

FIG. 2 shows the result of an X-ray single crystal structural analysis (Oak Ridge Thermal Ellipsoid Plot) of Compound 2f.

Example A6

Synthesis of Compound 2g: RUPTBU3

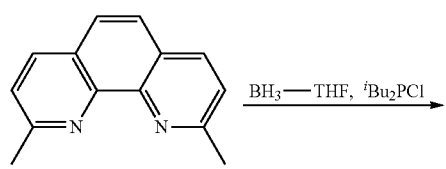

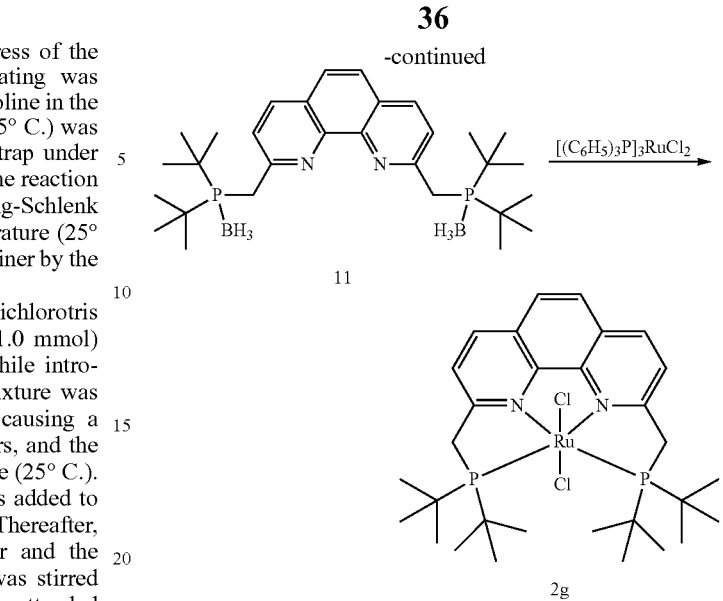

A reaction was performed in the same manner as in Example A5, except that chloro di-t-butyl phosphine was used instead of chloro dicyclohexyl phosphine, thereby obtaining Compound 2g (RUPTBU3).

The spectral data of Compound 2g (RUPTBU3) is shown below.

$^1$H NMR (600 MHz, CDCl$_3$): δ 8.11 (d, 2H, J=8.2 Hz, C$_{12}$H$_6$N$_2$), 7.87 (d, 2H, J=8.3 Hz, C$_{12}$H$_6$N$_2$), 7.80 (s, 2H, C$_{12}$H$_6$N$_2$), 4.04 (d, 4H, J=8.2 Hz, PCH$_2$), 1.48 (d, 36H, J=11.7 Hz, C(CH$_3$)$_3$). $^{13}$C NMR (151 MHz, CDCl$_3$): δ 166.4, 150.1, 132.7, 128.7, 125.3, 125.3, 121.7, 39.5 (d, $^1J_{PC}$=17.4 Hz), 37.5, 30.7. $^{31}$P{$^1$H} NMR (243 MHz, CDCl$_3$): δ 70.7. HRMS (ESI, (M-Cl)$^+$) Calcd for C$_{30}$H$_{46}$ClN$_2$P$_2$Ru$^+$: 633.19. Found m/z=633.19.

Reaction Example A1

Reduction of Amide

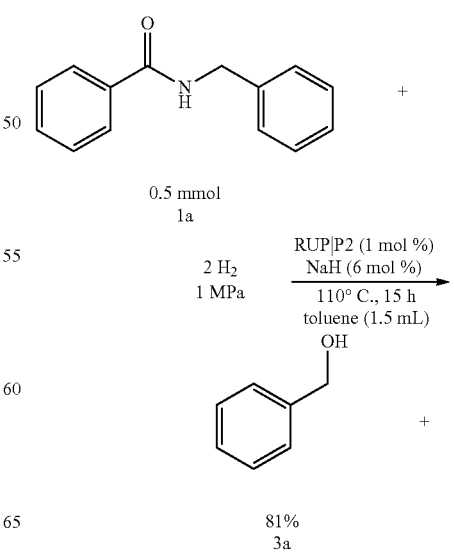

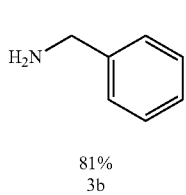

81%
3b

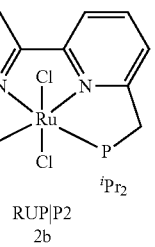

RUP|P2
2b

In an argon gas atmosphere, a stirrer, a ruthenium complex (Compound 2b; RUPIP2) (2.9 mg, 0.005 mmol), sodium hydride (1.3 mg, 0.03 mmol), N-benzylbenzamide (105.63 mg, 0.5 mmol) and toluene (1.5 mL) were placed in a dried fluororesin tube (30 mL). Thereafter, the tube containing the compound was rapidly inserted into an autoclave. Subsequently, the autoclave was hermetically sealed while being grounded, and hydrogen gas was introduced into the autoclave from a hydrogen compressed gas cylinder connected via a stainless-steel pipe, thereby substituting the inside of the autoclave with hydrogen gas. More specifically, 1-MPa hydrogen gas pressure was applied inside the autoclave, and then the hydrogen gas pressure was removed through a leak valve. This operation (substitution and desubstitution) was repeated 10 times. Finally, the hydrogen gas inside the autoclave was set to 1 MPa, and a reaction was performed for 15 hours using a constant-temperature bath at 110° C.

After the reaction was completed, the autoclave was cooled to substantially room temperature by being immersed in an icy bath. Then, the leak valve of the autoclave was opened and the hydrogen gas inside the autoclave was released into the air. Subsequently, the tube was taken out of the autoclave, thereby obtaining a reaction product (solution). For $^1$H NMR analysis, an internal standard substance (1,1,2,2-tetra chloro ethane) was added to the solution. Based on the hydrogen atom amount of the internal standard substance, the yield of the reaction product was calculated. As a result, the yields of benzyl alcohol and benzylamine were both 81% (corresponding to Entry 2 in Table 1 described later).

Reaction Example A2

Reduction of Amide

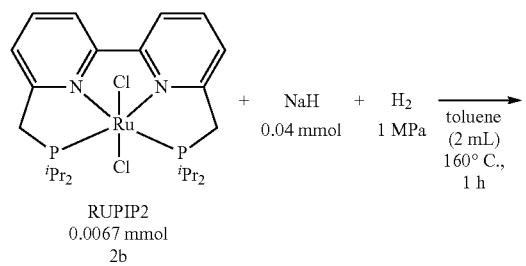

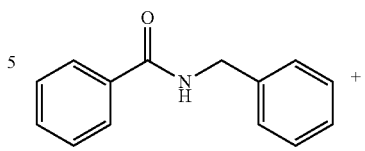

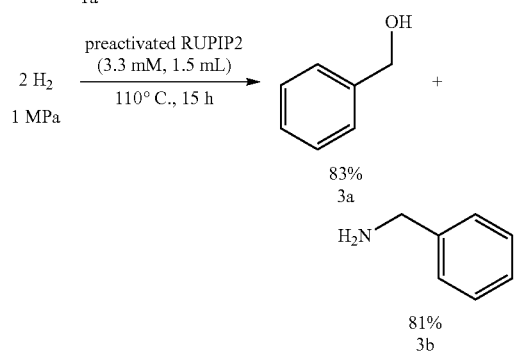

(1) Preactivation of Catalyst

In an argon gas atmosphere, a stirrer, a ruthenium complex (Compound 2b; RUPIP2) (3.9 mg, 0.0067 mmol), sodium hydride (1.7 mg, 0.04 mmol), and toluene (2.0 mL) were placed in a dried fluororesin tube (30 mL). Thereafter, the tube containing the compound was rapidly inserted into an autoclave. Subsequently, the autoclave was hermetically sealed while being grounded, and hydrogen gas was introduced into the autoclave from a hydrogen compressed gas cylinder connected via a stainless-steel pipe, thereby substituting the inside of the autoclave with hydrogen gas. More specifically, 1-MPa hydrogen gas pressure was applied inside the autoclave, and then the hydrogen gas pressure was removed through a leak valve. This operation (substitution and desubstitution) was repeated 10 times. Finally, the hydrogen gas inside the autoclave was set to 1 MPa, and a reaction was performed for an hour using a constant-temperature bath at 160° C.

(2) Hydrogenation Reaction of Substrate

After the reaction was completed, the autoclave was cooled to substantially room temperature by being immersed in an icy bath. Then, the leak valve of the autoclave was opened and the hydrogen gas inside the autoclave was released into the air. Subsequently, in an argon gas atmosphere, the reaction solution (1.5 mL) was obtained from the autoclave using a gas-tight syringe, and placed in another autoclave (a stirrer, and N-benzylbenzamide (105.63 mg, 0.5 mmol) were placed in a dried fluororesin tube (30 mL) in an argon gas atmosphere; thereafter, the tube containing this compound was rapidly inserted into an autoclave, and the inside of the autoclave was substituted with argon). Subsequently, the autoclave was hermetically sealed while being grounded, and hydrogen gas was introduced into the autoclave from a hydrogen compressed gas cylinder connected via a stainless-steel pipe, thereby substituting the inside of the autoclave with hydrogen gas. More specifically, 1-MPa hydrogen gas pressure was applied inside the autoclave, and then the hydrogen gas pressure was removed through a leak valve. This operation (substitution and desubstitution) was repeated 10 times. Finally, the hydrogen gas inside the autoclave was set to 1 MPa, and a reaction was performed for 15 hours using a constant-temperature bath at 110° C.

For $^1$H NMR analysis, an internal standard substance (1,1,2,2-tetra chloro ethane) was added to the solution. Based on the hydrogen atom amount of the internal standard substance, the yield of the reaction product was calculated. As a result, the yields of benzyl alcohol and benzylamine were 83% and 81%, respectively (corresponding to Entry 8 in Table 1 described later).

Reaction Example A3

Hydrogenation Reaction of Various Substrates

A hydrogenation reaction was performed in the same manner as in Reaction Examples A1 and A2, except that the conditions specified in Table 1 were used. Table 1 shows the results.

Reaction Example A1 is an example performed without preactivation of catalyst. Reaction Example A2 is an example performed with preactivation of catalyst. The step of Reaction Example A2 may be expressed as follows.

(1) Condition of Preactivation of Catalyst $$\text{Catalyst} + \text{Base} + \text{H}_2 \xrightarrow[P_1]{\text{toluene (1.0 – 3.0 mL)}, T_1, t_1} \text{preactivation Ru Catalyst}$$

(2) Condition of Hydrogenation Reaction $$\text{Substrate} + \text{H}_2 \xrightarrow[\text{toluene (1.0–2.0 mL)}, T_2, t_2]{\text{preactivation Ru Catalyst}} \text{Product}$$
$$0.5 – 1.0 \text{ mmol } P_2$$

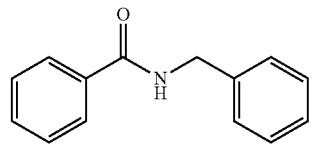 [SMILES: O=C(NCc1ccccc1)c1ccccc1]

1a

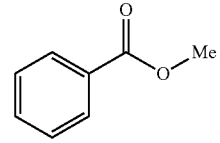

1b

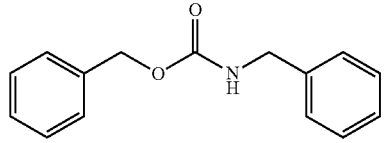

1c

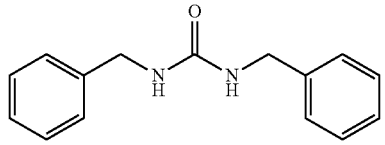

1d

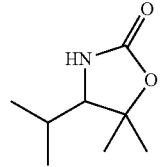

1e

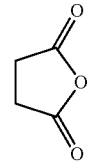

1f

TABLE 1

| entry | Substrate (mmol) | Catalyst (mol %) | Base (mol %) | Condition of preactivation of catalyst ($P_1$ (MPa), $T_1$ (° C.), $t_1$ (h)) | Condition of hydrogenation reaction ($P_2$ (MPa), $T_2$ (° C.), $t_2$ (h)) | Product(s)[a] (%) | |
|---|---|---|---|---|---|---|---|
| 1 | 1a (0.5) | 2a (1) | NaH (6) | none | 1, 110, 15 | 3a (0) | 3b (0) |
| 2 | 1a (0.5) | 2b (1) | NaH (6) | none | 1, 110, 15 | 3a (81) | 3b (81) |
| 3 | 1a (0.5) | 2c (1) | NaH (6) | none | 1, 110, 15 | 3a (82) | 3b (80) |
| 4 | 1a (0.5) | 2d (1) | NaH (6) | none | 1, 110, 15 | 3a (57) | 3b (56) |
| 5 | 1a (0.5) | 2e (1) | NaH (6) | none | 1, 110, 15 | 3a (4) | 3b (<1) |
| 6 | 1a (0.5) | 2f (1) | NaH (6) | none | 1, 110, 15 | 3a (6) | 3b (4) |
| 7 | 1a (0.5) | 2g (1) | NaH (6) | none | 1, 110, 15 | 3a (1) | 3b (<1) |
| 8 | 1a (0.5) | 2b (1) | NaH (6) | 1, 160, 1 | 1, 110, 15 | 3a (83) | 3b (81) |
| 9 | 1b (1.0) | 2c (1) | NaH (8) | none | 6, 160, 4 | 3a (99) | |
| 10 | 1c (1.0) | 2c (1) | NaH (6) | 8, 160, 2 | 6, 160, 24 | 3a (99) | 3b (94) |
| 11 | 1d (1.0) | 2c (1) | NaH (6) | 8, 160, 2 | 6, 160, 24 | 3b (99) | |
| 12 | 1e (1.0) | 2c (1) | NaH (6) | 8, 160, 2 | 6, 190, 120 | 3c (52) | |
| 13 | 1f (0.5) | 2f (2) | NaH (8) | 8, 160, 5 | 8, 190, 18 | 3d (98) | |
| 14 | 1g (1.0) | 2c (2) | NaH (12) | 8, 160, 5 | 8, 190, 24 | 3e (6) | 3f (10) |
| 15 | 1h (0.5) | 2c (2) | NaH (12) | 8, 160, 5 | 8, 190, 18 | 3d (7) | 1i (91) |
| 16 | 1i (1.0) | 2f (2) | NaH (4) | 8, 160, 5 | 8, 160, 18 | 3d (99) | |

[a]NMR analysis

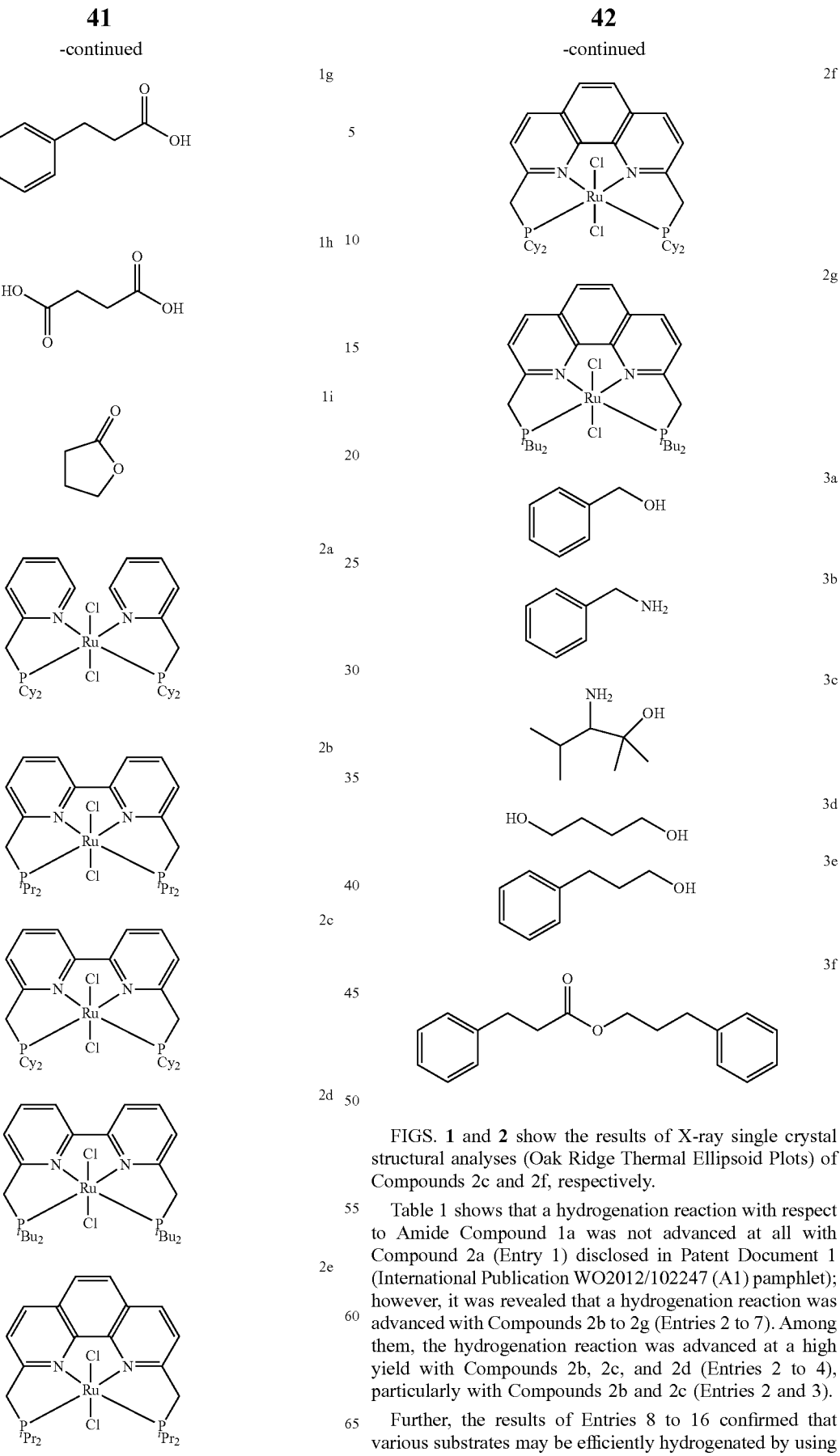

FIGS. 1 and 2 show the results of X-ray single crystal structural analyses (Oak Ridge Thermal Ellipsoid Plots) of Compounds 2c and 2f, respectively.

Table 1 shows that a hydrogenation reaction with respect to Amide Compound 1a was not advanced at all with Compound 2a (Entry 1) disclosed in Patent Document 1 (International Publication WO2012/102247 (A1) pamphlet); however, it was revealed that a hydrogenation reaction was advanced with Compounds 2b to 2g (Entries 2 to 7). Among them, the hydrogenation reaction was advanced at a high yield with Compounds 2b, 2c, and 2d (Entries 2 to 4), particularly with Compounds 2b and 2c (Entries 2 and 3).

Further, the results of Entries 8 to 16 confirmed that various substrates may be efficiently hydrogenated by using the metal complex of the present invention.

Reaction Example A4

Dehydrogenation Reaction

The following dehydrogenation reaction (oxidation reaction) was performed using Compound 2c obtained in Example A2. A pyrrole skeleton of Lipitor was synthesized.

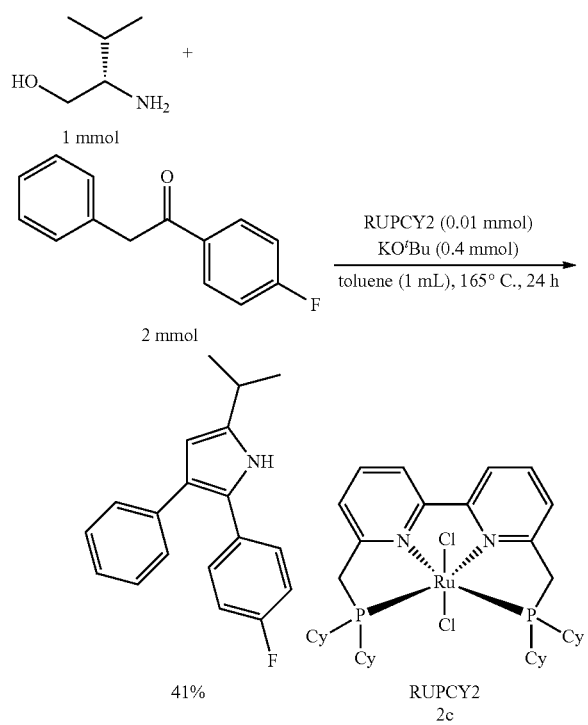

A stirrer, a ruthenium complex (Compound 2c; RUPCY2) (7.5 mg, 0.01 mmol), potassium tert-butoxide (44.9 mg, 0.4 mmol), benzil-4-fluoro phenyl ketone (429 mg, 2.0 mmol), toluene (1.0 mL), and L-Valinol (0.11 mL, 1.0 mmol) were added to a 10-mL Young-Schlenk container that had been dried under reduced pressure and substituted with nitrogen. Thereafter, the mixture was reacted for 24 hours in a constant-temperature bath at 165° C. After the reaction was completed, a 1.5-M hydrogen chloride-methanol solution (400 µL) was added to the mixture, and then 1-phenyl-1-propanol was added as a standard substance. $^1$H NMR measurement was performed using a deuterated chloroform solvent. As a result, the target product, i.e., 2-(4-fluorophenyl)-5-isopropyl-3-phenyl-1H-pyrrole was obtained at an NMR yield of 41%.

Reaction Example A5

Reduction Of Amide

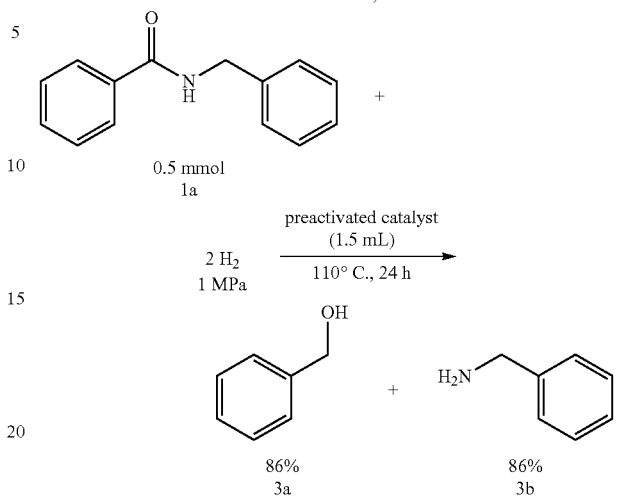

(1) Preactivation of Catalyst

In an argon gas atmosphere, a stirrer, a ruthenium complex (Compound 2b; RUPIP2) (0.0067 mmol, 3.98 mg) and sodium-2-methyl-2-adamantoxide (0.067 mmol, 12.6 mg) were placed in a dried fluororesin tube (30 mL). Thereafter, the tube containing this compound was rapidly inserted into an autoclave, and toluene (2.0 mL) was added in an argon atmosphere. Subsequently, the autoclave was hermetically sealed while being grounded, and hydrogen gas was introduced into the autoclave from a hydrogen compressed gas cylinder connected via a stainless-steel pipe, thereby substituting the inside of the autoclave with hydrogen gas. More specifically, 1-MPa hydrogen gas pressure was applied inside the autoclave, and then the hydrogen gas pressure was removed through a leak valve. This operation (substitution and desubstitution) was repeated 10 times. Finally, the hydrogen gas inside the autoclave was set to 1 MPa, and a reaction was performed for 5 hours using a constant-temperature bath at 160° C.

(2) Hydrogenation Reaction of Substrate

After the reaction was completed, the autoclave was cooled to substantially room temperature by being immersed in an icy bath. Then, the leak valve of the autoclave was opened and the hydrogen gas inside the autoclave was released into the air. Subsequently, in an argon gas atmosphere, the reaction solution (1.5 mL) was obtained from the autoclave using a gas-tight syringe, and placed in another autoclave (a stirrer, and N-benzylbenzamide (0.5 mmol, 105.63 mg) were placed in a dried fluororesin tube (30 mL) in an argon gas atmosphere; thereafter, the tube containing this compound was rapidly inserted into an autoclave, and the inside of the autoclave was substituted with argon). Subsequently, the autoclave was hermetically sealed while being grounded, and hydrogen gas was introduced into the autoclave from a hydrogen compressed gas cylinder connected via a stainless-steel pipe, thereby substituting the inside of the autoclave with hydrogen gas. More specifically, 1-MPa hydrogen gas pressure was applied inside the autoclave, and then the hydrogen gas pressure was removed through a leak valve. This operation (substitution and desubstitution) was repeated 10 times. Finally, the hydrogen gas inside the autoclave was set to 1 MPa, and a reaction was performed for 24 hours using a constant-temperature bath at 110° C. For $^1$H NMR analysis, an internal standard substance (mesitylene) was added to the solution. Based on the hydrogen atom amount of the internal standard substance, the yield of the reaction product was calculated. The results of the analysis showed that the yields of benzyl alcohol and benzylamine were both 86% (corresponding to Entry 8 in Table 2 described later).

Reaction Example A6

Hydrogenation Reaction of Various Substrates

A hydrogenation reaction was performed in the same manner as in Reaction Example A5, except that the conditions specified in Table 2 were used. Tables 2 and 3 show the results.

TABLE 2

| entry | amide | P/ MPa | T/ °C. | t/ h | conversion | alcohol | amine | aminoalcohol |
|---|---|---|---|---|---|---|---|---|
| 1 | benzamide (PhC(O)NH$_2$) | 6 | 160 | 39 | >99 | 90 | — | — |
| 2 | N,N-dimethylbenzamide | 1 | 110 | 15 | 98 | 98 | — | — |
| 3 | N,N-diethylbenzamide | 3 | 130 | 15 | >99 | 98 | — | — |
| 4 | N-benzylacetamide | 2 | 120 | 15 | 89 | — | 89 | — |
| 5 | N-octylbenzamide | 1 | 110 | 24 | >99 | >99 | >99 | — |
| 6 | 4-methoxy-N-benzylbenzamide | 2 | 120 | 15 | 87 | 87 | 86 | — |
| 7 | 4-methyl-N-benzylbenzamide | 2 | 110 | 39 | 94 | 9 | 88 | — |
| 8 | N-benzylbenzamide | 1 | 110 | 24 | 88 | 86 | 86 | — |

TABLE 2-continued

| entry | amide | P/ MPa | T/ °C. | t/ h | result[a] (%) | | | |
|---|---|---|---|---|---|---|---|---|
| | | | | | conversion | alcohol | amine | aminoalcohol |
| 9 | 4-(F₃C)C₆H₄-C(O)NH-CH₂-C₆H₄-Cl (structure) | 0.5 | 80 | 15 | 79 | 79 | 77 | — |

[a] NMR analysis

TABLE 3

| entry | amide | P/ MPa | T/ °C. | t/ h | result[a] (%) | | | |
|---|---|---|---|---|---|---|---|---|
| | | | | | conversion | alcohol | amine | aminoalcohol |
| 10 | 4-Ph-C₆H₄-C(O)NH-CH₂Ph (structure) | 2 | 120 | 24 | 93 | 93 | 91 | — |
| 11 | 4-(F₃C)C₆H₄-C(O)NH-CH₂Ph (structure) | 1 | 110 | 15 | 98 | 98 | 96 | — |
| 12 | Me(H₂C)₇-C(O)NH-(CH₂)₇Me (structure) | 3 | 130 | 39 | 93 | 93 | 92 | — |
| 13 | Cyclohexyl-C(O)NH-(CH₂)₇Me (structure) | 4 | 140 | 62 | 98 | 98 | 96 | — |
| 14 | tBu-C(O)NH-(CH₂)₇Me (structure) | 8 | 160 | 48 | 92 | 65 | 74 | — |
| 15 | caprolactam (structure) | 3 | 130 | 39 | 92 | — | 3[b] | 90 |
| 16 | N-methyl caprolactam (structure) | 2 | 120 | 15 | 57 | — | —[b] | 57 |
| 17 | 2-pyrrolidinone (structure) | 8 | 190 | 39 | 87 | — | 65[b] | 2 |

TABLE 3-continued

| entry | amide | P/ MPa | T/ °C. | t/ h | result[a] (%) | | |
|---|---|---|---|---|---|---|---|
| | | | | | conversion | alcohol | amine | aminoalcohol |
| 18 | (structure: 4-CF3-C6H4-C(O)NH-CH(CH2Ph)-C(O)NH-(CH2)7Me) | 8 | 160 | 24 | >99 | >99[c] | >99[d] | 96[e] |

[a] NMR analysis
[b] Cyclic amine was obtained
[c] A was obtained
[d] B was obtained
[e] C was obtained

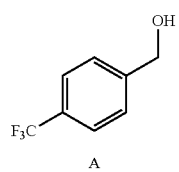

A

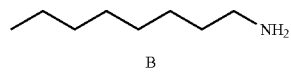

B

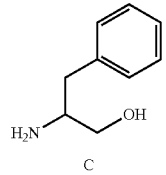

C

B. Cobalt Complex

Example B1

Synthesis of Compound 2h: COPCY2

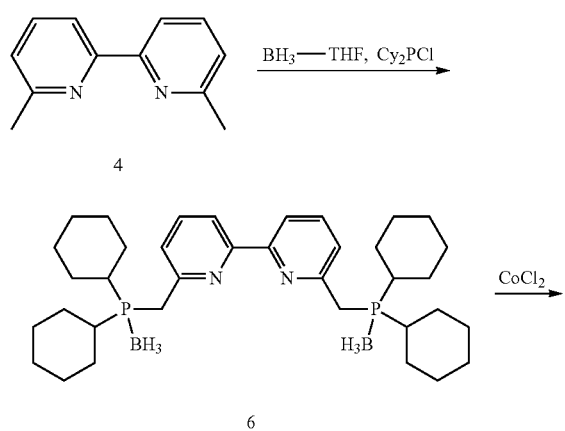

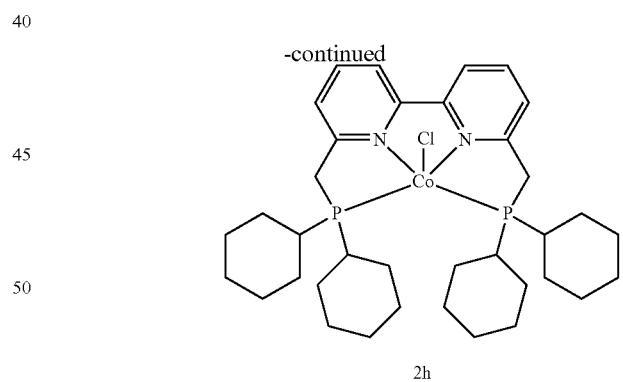

2h

Synthesis of Compound 2h

Compound 6 (6,6'-bis dicyclohexyl phosphino methyl-2,2'-bipyridine borane complex) (302.2 mg, 0.50 mmol) produced in the same manner as in Example A2(1) and degassed morpholine (12.5 mL) were placed in a 100-mL Young-Schlenk container substituted with argon gas. Thereafter, the Young-Schlenk container was placed in an oil bath, and heated to 120° C. while stirring the components in the Young-Schlenk container, thereby causing a reaction. The progress of the reaction was confirmed by TLC, and the heating was stopped after two hours. Subsequently, the morpholine in the reaction mixture restored to room temperature (25° C.) was removed after collection with a liquid nitrogen trap under reduced pressure (0.1 to 2 mmHg). At this time, the reaction mixture was sufficiently stirred, and the Young-Schlenk container was immersed in water at room temperature (25° C.) to prevent cooling of the Young-Schlenk container by the heat of vaporization.

After sufficiently removing the morpholine, anhydrous cobalt (II) chloride (II) (65.0 mg, 0.50 mmol) and 2-propanol (25 mL) were added, and the mixture was heated to 83° C. using an oil bath, thereby causing a reaction overnight. Thereafter, the heating was stopped, and the reaction mixture was restored to room temperature (25° C.).

Subsequently, with the reaction mixture restored to room temperature (25° C.), the solvent was removed after collection with a liquid nitrogen trap under reduced pressure (0.1 to 2 mmHg) until precipitates were generated and the reaction solution had a suspension state. Thereafter, the reaction solution was heated again to 83° C. using an oil bath, thereby dissolving the precipitates. After confirming that all precipitates were dissolved, the power of the oil bath was turned off with the Young-Schlenk container immersed therein, and the solution was allowed to cool. The generated reddish brown crystal was filtered out and dried, thereby obtaining 247.8 mg (0.35 mmol, 70%) of Compound 2h (COPCY2) as a reddish brown crystal.

The spectral data of Compound 2h (COPCY2) is shown below.

HRMS (FAB, (M-Cl)$^+$) Calcd for $C_{36}H_{54}ClN_2P_2Co^+$: 670.2783. Found m/z=670.2707.

Figure 3:
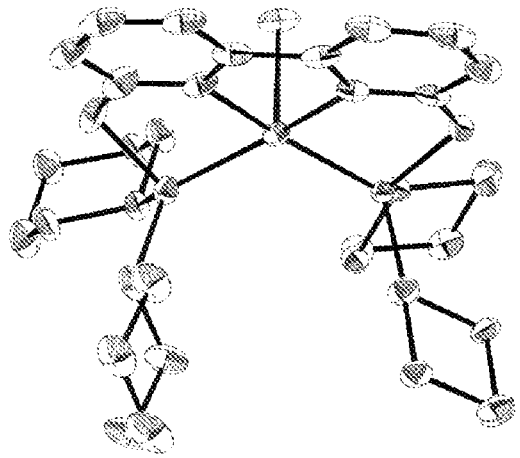
FIG. 3 shows a result of the X-ray single crystal structural analysis of a cobalt complex (Compound 2h) obtained in Example B1.

FIG. 3 shows the results of an X-ray single crystal structural analysis (Oak Ridge Thermal Ellipsoid Plot).

Reaction Example B1

Reduction of Ketone

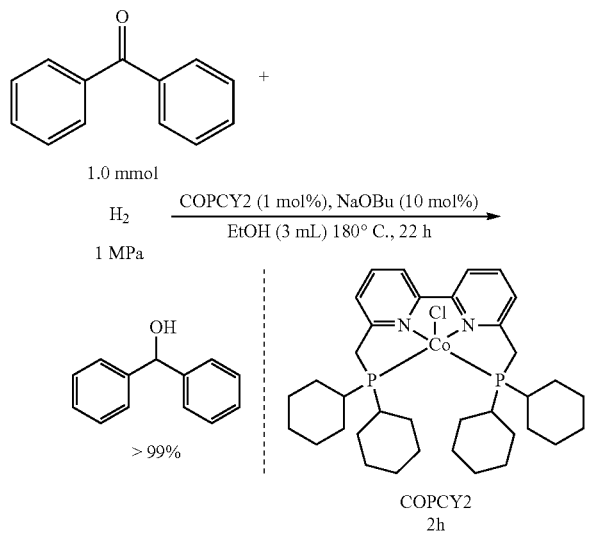

A stirrer, a cobalt complex (Compound 2h; COPCY3) (6.71 mg, 0.010 mmol), sodium t-butoxide (9.6 mg, 0.10 mmol), and dehydrated and degassed ethanol (3 mL) were placed in a dried fluororesin tube (30 mL). Thereafter, the tube containing this mixture was rapidly inserted into an autoclave. Subsequently, the autoclave was hermetically sealed while being grounded, and hydrogen gas was introduced into the autoclave from a hydrogen compressed gas cylinder connected via a stainless-steel pipe, thereby substituting the inside of the autoclave with hydrogen gas. More specifically, 0.8-MPa hydrogen gas pressure was applied inside the autoclave, and then the hydrogen gas pressure was removed through a leak valve. This operation (substitution and desubstitution) was repeated 10 times. Finally, the hydrogen gas pressure inside the autoclave was set to 1 MPa, and a reaction was performed for 22 hours using a constant-temperature bath at 160° C.

After the reaction was completed, the autoclave was cooled to substantially room temperature by being immersed in an icy bath. Then, the leak valve of the autoclave was quietly opened and the hydrogen gas inside the autoclave was released into the air. Subsequently, the tube was taken out of the autoclave, thereby obtaining a reaction product (solution). A hydrogen chloride diethylether solution (0.05-mL, 2-M diethylether solution, 0.10 mmol) was added to this solution; thereafter, the mixture was concentrated under reduced pressure using an evaporator. For $^1$H NMR analysis, an internal standard substance (mesitylene) was added to the solution. Based on the integration value of the hydrogen atom amount of the internal standard substance, the yield of the reaction product was calculated. The results showed that the yield of diphenyl methanol was >99%.

C. Iron Complex

Example C1

Synthesis of Compound 2i: FEPCY2

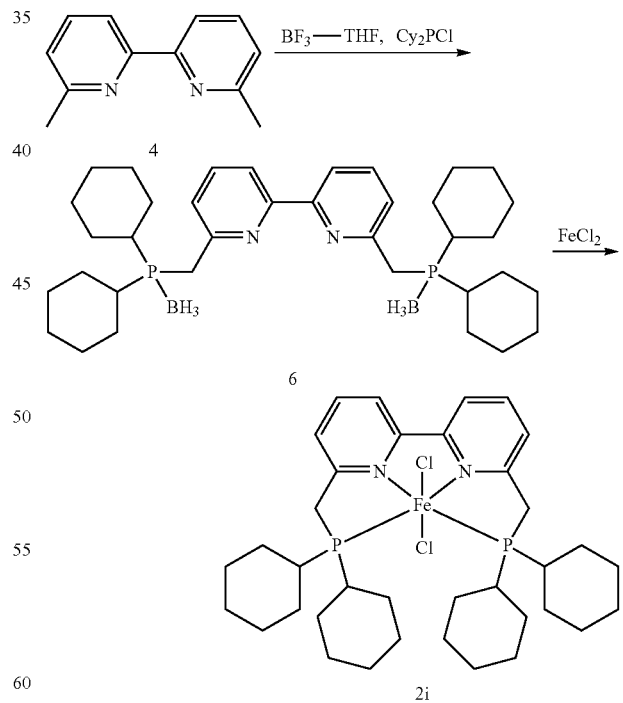

Synthesis of Compound 2i

Compound 6 (6,6'-bis dicyclohexyl phosphino methyl-2, 2'-bipyridine borane complex) (147.3 mg, 0.21 mmol) produced in the same manner as in Example A2(1), distilled diethylamine (5.0 mL) and THF (8 mL) were placed in a 100-mL Young-Schlenk container substituted with argon gas. Thereafter, the Young-Schlenk container was placed in an oil bath, and heated to 60° C. while stirring the components in the Young-Schlenk container, thereby causing a reaction. The progress of the reaction was confirmed by TLC, and the heating was stopped after four days. Subsequently, the solvent in the reaction mixture restored to room temperature (25° C.) was removed after collection with a liquid nitrogen trap under reduced pressure (0.1 to 2 mmHg). At this time, the reaction mixture was sufficiently stirred, and the Young-Schlenk container was immersed in water at room temperature (25° C.) to prevent cooling of the Young-Schlenk container by the heat of vaporization.

After sufficiently removing the solvent, anhydrous iron (II) chloride (25.6 mg, 0.20 mmol), and dehydrated and degassed ethanol (5 mL) were added while introducing argon gas into the container, and the mixture was heated to 80° C. using an oil bath, thereby causing a reaction overnight. Thereafter, the heating was stopped, and the reaction mixture was restored to room temperature (25° C.).

Subsequently, with the reaction mixture restored to room temperature (25° C.), the solvent was removed after collection with a liquid nitrogen trap under reduced pressure (0.1 to 2 mmHg) until precipitates were generated and the reaction solution had a suspension state. Thereafter, the reaction solution was heated again to 80° C. using an oil bath, thereby dissolving the precipitates. After confirming that all precipitates were dissolved, the power of the oil bath was turned off with the Young-Schlenk container immersed therein, and the mixture was allowed to cool. The generated reddish brown crystal was filtered out, washed with hexane, and dried, thereby obtaining 35.2 mg (0.05 mmol, 25%) of Compound 2i (FEPCY2) as a reddish brown crystal.

The spectral data of Compound 2i (FEPCY2) is shown below.

HRMS (ESI, (M-Cl)$^+$) Calcd for $C_{36}H_{54}ClFeN_2P_2{}^+$: 667.2796. Found m/z=667.2724.

Figure 4:
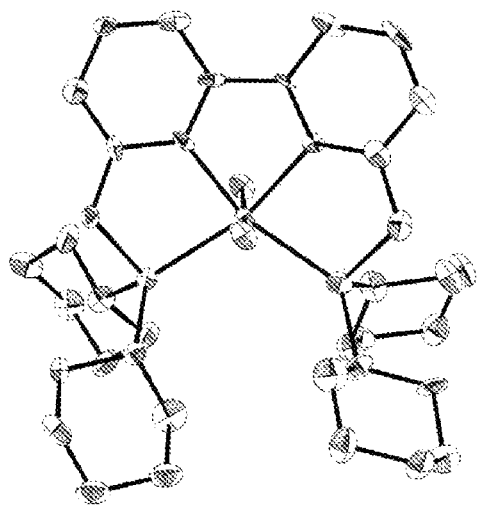
FIG. 4 shows a result of the X-ray single crystal structural analysis of a cobalt complex (Compound 2i) obtained in Example C1 (Oak Ridge Thermal Ellipsoid Plot).

FIG. 4 shows the results of an X-ray single crystal structural analysis (Oak Ridge Thermal Ellipsoid Plot).

Example C2

Synthesis of Compound 2j: FEPCY3

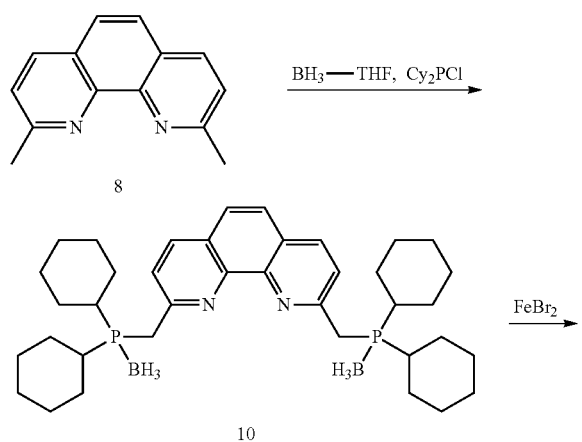

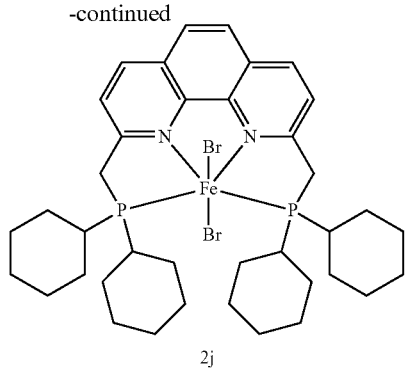

Synthesis of Compound 2j

Compound 10 (2,9-bis dicyclohexyl phosphino methyl-1,10-phenanthroline borane complex) (604.4 mg, 1.0 mmol) produced in the same manner as in Example A5(1) and degassed morpholine (15.0 mL) were placed in a 100-mL Young-Schlenk container substituted with argon gas. Thereafter, the Young-Schlenk container was placed in an oil bath, and heated to 120° C. while stirring the components in the Young-Schlenk container, thereby causing a reaction. The progress of the reaction was confirmed by TLC, and the heating was stopped after two hours. Subsequently, the solvent in the reaction mixture restored to room temperature (25° C.) was removed after collection with a liquid nitrogen trap under reduced pressure (0.1 to 2 mmHg). At this time, the reaction mixture was sufficiently stirred, and the Young-Schlenk container was immersed in water at room temperature (25° C.) to prevent cooling of the Young-Schlenk container by the heat of vaporization.

After sufficiently removing the morpholine, anhydrous iron (II) bromide (215.7 mg, 1.0 mmol) and dehydrated and degassed ethanol (25 mL) were added while introducing argon gas into the container, and the mixture was heated to 80° C. using an oil bath, thereby causing a reaction overnight. Thereafter, the heating was stopped, and the reaction mixture was restored to room temperature (25° C.).

Subsequently, with the reaction mixture restored to room temperature (25° C.), the solvent was removed after collection with a liquid nitrogen trap under reduced pressure (0.1 to 2 mmHg) until precipitates were generated and the reaction solution had a suspension state. Thereafter, the reaction solution was heated again to 80° C. using an oil bath, thereby dissolving the precipitates. After confirming that all precipitates were dissolved, the power of the oil bath was turned off with the Young-Schlenk container immersed therein, and the solution was allowed to cool. The generated reddish brown crystal was filtered out, washed with hexane, and dried, thereby obtaining 444.3 mg (0.54 mmol, 54%) of Compound 2j (FEPCY3) as a reddish brown crystal.

The spectral data of Compound 2j (FEPCY3) is shown below.

HRMS (ESI, (M-Br)$^+$) Calcd for $C_{38}H_{54}BrFeN_2P_2{}^+$: 735.2292. Found m/z=735.2325.

Figure 5:
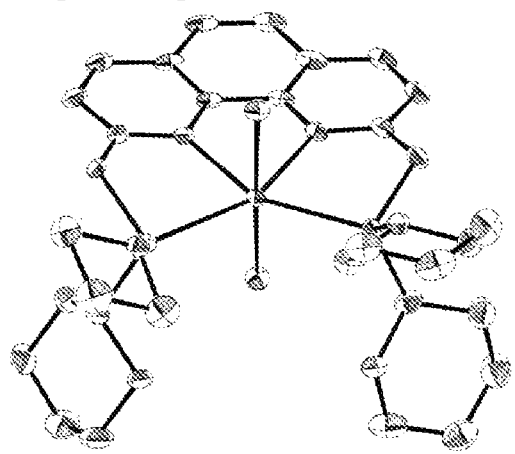
FIG. 5 a result of the X-ray single crystal structural analysis of an iron complex (Compound 2j) obtained in Example C2 (Oak Ridge Thermal Ellipsoid Plot).

FIG. 5 shows the results of an X-ray single crystal structural analysis (Oak Ridge Thermal Ellipsoid Plot).

As in other Reaction Examples, the hydrogen transfer reaction may also be advanced with the iron complex thus synthesized above.

D. Nickel Complex

Example D1

Synthesis of Compound 2k: NIPCY2

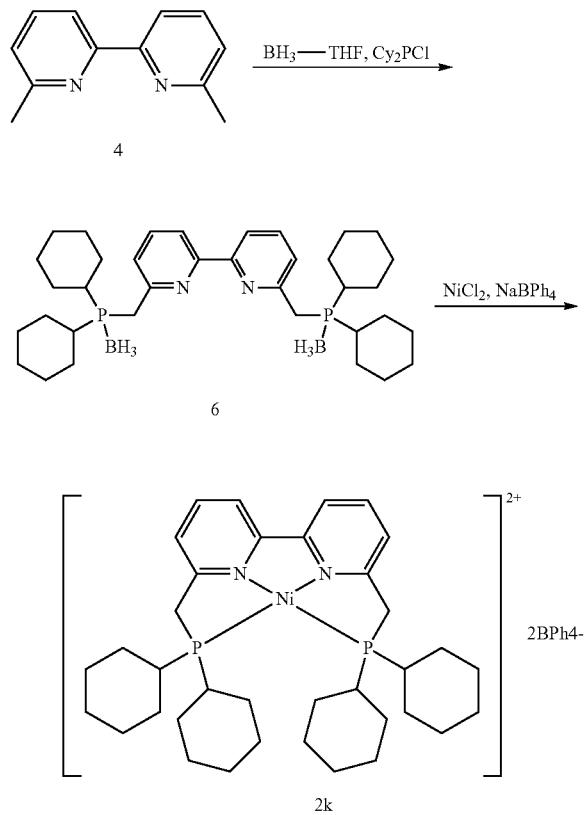

Synthesis of Compound 2k

Compound 6 (6, 6'-bis((dicyclohexyl phosphino)methyl)-2,2' bipyridine-diborane complex) (140.9 mg, 0.23 mmol) produced in the same manner as in Example A2(1), diethylamine (8 mL), and THF (10 mL) were placed in a 100-mL Young-Schlenk container substituted with argon gas. Thereafter, the Young-Schlenk container was placed in an oil bath, and heated to 65° C. while stirring the components in the Young-Schlenk container, thereby causing a reaction. The heating was stopped after 45 hours. Subsequently, the diethylamine and THF in the reaction mixture restored to room temperature (25° C.) were removed after collection with a liquid nitrogen trap under reduced pressure (0.1 to 2 mmHg).

After sufficiently removing the diethylamine, nickel(II) chloride (30.7 mg, 0.24 mmol) and dehydrated methanol (10 mL) were added while introducing argon gas into the Schlenk container, and the mixture was heated to 70° C. using an oil bath, thereby causing a reaction. Three hours later, the heating was stopped, and the precipitates in the mixed solution were removed by Celite filtration in an argon atmosphere.

Sodium tetraphenyl borate (398.9 mg, 1.17 mmol) and dehydrated methanol (5 mL) were placed in another Schlenk container. The mixture was stirred at room temperature (25° C.) for 30 minutes, causing it to be dissolved. The solution was added to the above reacted solution while introducing argon gas, thereby immediately generating flesh-colored precipitates. After 4 hours of stirring, the generated flesh-colored precipitates were collected by filtration in an argon atmosphere, thereby obtaining 211.3 mg (0.166 mmol, 71%) of a nickel complex (Compound 2k).

The spectral data of the nickel complex (Compound 2k) is shown below.

$^1$H NMR (600 MHz, CD$_3$CN): δ 6 8.15 (t, 2H, J=7.9 Hz, C$_{10}$H$_6$N$_2$), 7.98 (d, 2H, J=8.2 Hz, C$_{10}$H$_6$N$_2$), 7.67 (d, 2H, J=8.2 Hz, C$_{10}$H$_6$N$_2$), 7.25 (br, 16H, B(C$_6$H$_5$)$_4$), 6.97 (t, 16H, J=7.2 Hz, B(C$_6$H$_5$)$_4$), 6.81 (t, 8H, J=7.2 Hz, B(C$_6$H$_5$)$_4$), 3.80 (t, 4H, J=6.2 Hz, PCH$_2$), 1.24-2.30 (m, 44H, C$_6$H$_{11}$). $^{13}$C NMR (151 MHz, CD$_3$CN): δ 164.8, 164.4, 164.1, 163.8, 161.9, 155.4, 143.1, 136.2, 126.1, 122.2, 121.9, 35.8, 35.2, 29.8, 28.2, 27.0, 26.6, 25.7. $^{31}$P NMR (243 MHz, CD$_3$CN): δ5.2.

Reaction Example D1

Reduction of Ketone

The reduction reaction using molecular hydrogen of ketone was performed as follows. The reaction scheme is shown below.

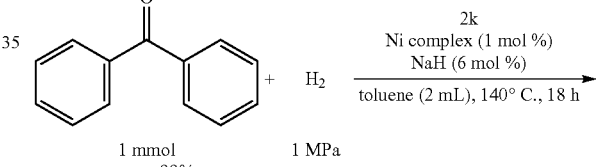

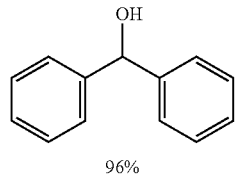

A stirrer, a nickel complex (Compound 2k) (12.7 mg, 0.01 mmol), sodium hydride (2.4 mg, 0.1 mmol), and benzophenone (182.2 mg, 1.0 mmol) were placed in a dried fluororesin tube (30 mL). The tube containing the mixture was rapidly inserted into an autoclave. Thereafter, dehydrated toluene (2 mL) was added to the mixture in the tube while introducing argon gas into the autoclave; then, the autoclave was rapidly hermetically sealed. Hydrogen gas was introduced into the autoclave from a hydrogen compressed gas cylinder connected via a stainless-steel pipe, thereby substituting the inside of the autoclave with hydrogen gas. More specifically, 1-MPa hydrogen gas pressure was applied inside the autoclave, and then the hydrogen gas pressure was removed through a leak valve. This operation was repeated three times. Finally, the hydrogen gas pressure inside the autoclave was set to 1 MPa, and a reaction was performed for 18 hours using a constant-temperature bath at 140° C.

After the reaction was completed, the autoclave was cooled to substantially room temperature by being immersed in an icy bath. Then, the leak valve of the autoclave was opened and the hydrogen gas inside the autoclave was released into the air. Subsequently, the tube was taken out of the autoclave, thereby obtaining a reaction product (solution). A hydrogen chloride-methanol solution (2.0 M, 50 µL, 0.1 mmol) was added to this solution to neutralize the solution. Thereafter, an internal standard substance (N,N-dimethyl formamide) was added to the solution. Based on the integration value of the hydrogen atom amount of the internal standard substance, the yield of the reaction product was calculated. The results showed that the yield of diphenyl methanol was 96%.

E. Rhodium Complex

Example E1

(Synthesis of Compound 21: RHPCY2(III))

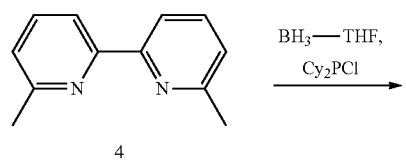

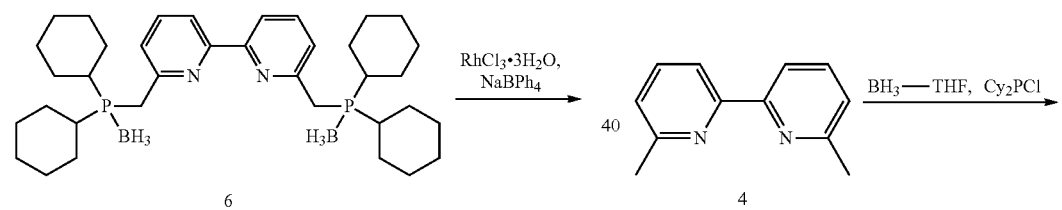

Synthesis of Compound 21

Compound 6 (6,6'-bis dicyclohexyl phosphino methyl-2, 2'-bipyridine borane complex) (120 mg, 0.2 mmol) produced in the same manner as in Example A2(1) and degassed morpholine (5 mL) were placed in a Schlenk container in an argon gas atmosphere, and the mixture was stirred for two hours at 120° C. The transparent solution was cooled to room temperature, and the morpholine was removed after collection with a liquid nitrogen trap under reduced pressure (0.1 to 2 mmHg). Dried and degassed ethanol (3 mL) and rhodium trichloride.trihydrate (RhCl$_3$/3H$_2$O) (0.2 mmol, 53 mg, added by being dissolved in 2 mL of dried and degassed ethanol) were added to the resulting white solid. After the reaction mixture was stirred for three hours at 80° C., and cooled to room temperature, yellow precipitates were confirmed. The precipitates were separated by Celite filtration in an argon atmosphere. A solution of sodium tetraphenyl borate (NaBPh$_4$) (0.2 mmol, 68 mg, added by being dissolved in 2 mL of dried and degassed methanol) was added to the filtrate; immediately, yellow precipitates were confirmed. After 30 minutes of stirring at room temperature, the precipitates were filtered out in an argon atmosphere, washed with dried ethanol, and dried under reduced pressure, thereby obtaining a rhodium(III)complex (Compound 21) (90 mg, 42%) as a pale yellow solid.

The spectral data of the rhodium(III)complex (Compound 21) is shown below.

$^1$H NMR (600 MHz, CD$_3$CN): δ=8.20 (d, J=7.6 Hz, 2H), 8.12 (t, J=7.6 Hz, 2H), 7.77 (d, J=7.6 Hz, 2H), 7.21 (br s, 8H), 6.93 (t, J=6.8 Hz, 8H), 6.82 (t, J=6.8 Hz, 4H), 4.13 (d, J=5.5 Hz, 4H), 2.62-2.61 (m, 4H), 1.76-1.65 (m, 28H), 1.25-1.19 (m, 12H); $^{13}$C{$^1$H} NMR (150.78 MHz, CD$_3$CN): δ=164.8, 164.6, 164.3, 164.0, 160.5, 155.9, 140.6, 135.7, 125.6, 122.0, 121.7, 39.4 (t, J$_{P-C}$=10.1 Hz) 36.9 (t, J$_{P-C}$=10.1 Hz), 29.6, 28.7, 27.1, 27.0, 25.5; $^{31}$P{$^1$H} NMR (242.75 MHz, CD$_3$CN): δ=43.24, 42.83 (d, J$_{Rh-P}$=98.6 Hz); HRMS (ESI, (M-BPh$_4$)$^+$) Calcd for C$_{36}$H$_{54}$Cl$_2$N$_2$P$_2$Rh$^+$: 749.2189. Found m/z=749.2232.

Example E2

(Synthesis of Compound 2m: RHPCY2(I))

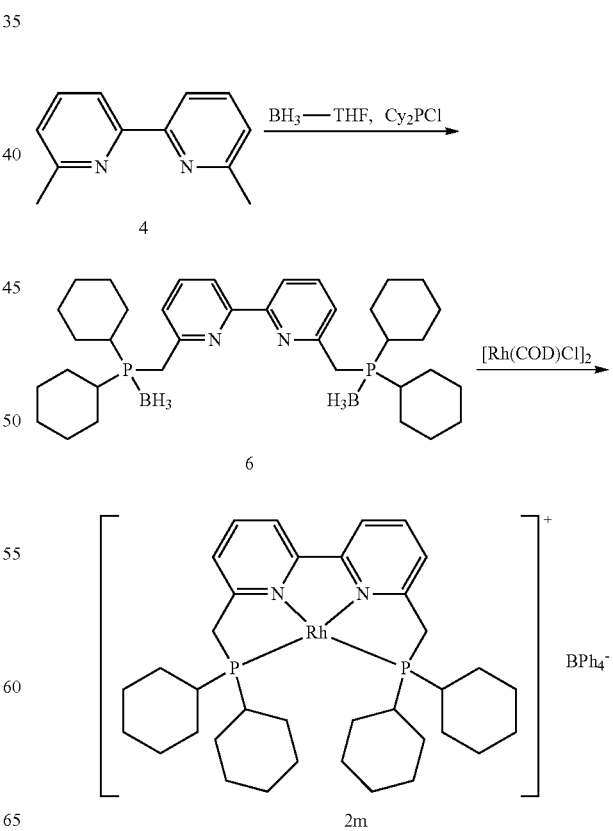

Synthesis of Compound 2m

Compound 6 (120 mg, 0.2 mmol) produced in the same manner as in Example A2(1) and degassed morpholine (5 mL) were placed in a Schlenk container in an argon gas atmosphere, and the mixture was stirred for two hours at 120° C. The transparent solution was restored to room temperature, and the morpholine was removed after collection with a liquid nitrogen trap under reduced pressure (0.1 to 2 mmHg). Dried and degassed ethanol (4 mL) and cyclooctadiene rhodium chloride dimer([Rh(cod)Cl]$_2$) (0.1 mmol, 49 mg) were added to the resulting white solid. After the reaction mixture was stirred for two hours at 80° C. and cooled to 50° C., a solution of sodium tetraphenyl borate (NaBPh$_4$) (0.2 mmol, 68 mg, added by being dissolved in 2 mL of dried and degassed methanol) was added to the filtrate. The resulting mixture was cooled to room temperature and further stirred for 30 minutes. The precipitates were filtered out in an argon atmosphere, washed with dried ethanol, and dried under reduced pressure, thereby obtaining a rhodium(I)complex (Compound 2m) (96 mg, 48%) as a deep green solid.

The spectral data of the rhodium(I)complex (Compound 2m) is shown below.

$^1$H NMR (600 MHz, DMSO-d$_6$): δ=8.28 (d, J=8.3 Hz, 2H), 8.17 (t, J=7.6 Hz, 2H), 7.84 (d, J=8.3 Hz, 2H), 7.21 (br s, 8H), 6.95 (t, J=7.6 Hz, 8H), 6.82 (t, J=6.8 Hz, 4H), 3.71 (s, 4H), 1.80-1.70 (m, 24H), 1.43-1.17 (m, 20H); $^{13}$C{$^1$H} NMR (150.78 MHz, DMSO-d$_6$) δ=164.3, 164.0, 163.6, 163.3, 162.0, 155.4, 137.8, 136.0, 125.7, 125.1, 122.0, 121.1, 38.06 (t, J$_{P-C}$=10.1 Hz) 34.8 (t, J$_{P-C}$=10.1 Hz), 28.7, 28.0, 26.7, 26.6, 26.1; $^{31}$P{$^1$H} NMR (242.75 MHz, DMSO-d$_6$): δ=60.22, 59.55 (d, J$_{Rh-P}$=164.4 Hz): HRMS (ESI+): m/z calcd for C$_{36}$H$_{54}$N$_2$P$_2$Rh (M−BPh$_4$): 679.2812. found 679.2783.

Reaction Example E1

Reduction of Ester

The results of a hydrogenation reaction of an ester compound (methyl-3-phenyl propionate) using the rhodium(III) complex (Compound 21) and rhodium(I)complex (Compound 2m) obtained above are shown below.

Preactivation of Catalyst

A rhodium complex and sodium hydride were placed in an autoclave Teflon tube equipped with a stirrer, and the tube was fixed to an autoclave, followed by argon substitution. In an argon atmosphere, toluene was added and the hydrogen pressure was set to 8 MPa. The mixture was stirred for the specified time at 160° C. Thereafter, the autoclave was cooled to room temperature.

Reaction with Substrate (Ester)

The hydrogen gas was carefully released from the autoclave in an argon atmosphere, and methyl-3-phenyl propionate (0.5 mmol, 0.079 mL) was added. Thereafter, the hydrogen pressure in the autoclave was increased to 8 MPa. The mixture was stirred for the specified time at 160° C. Thereafter, the autoclave was cooled to room temperature, and the hydrogen gas was carefully released. The reaction mixture was quenched with hydrochloric acid, and the solvent was removed. Thereafter, the reaction product was analyzed by $^1$H NMR.

(1) Reaction using Rhodium(III)Complex (Compound 21)

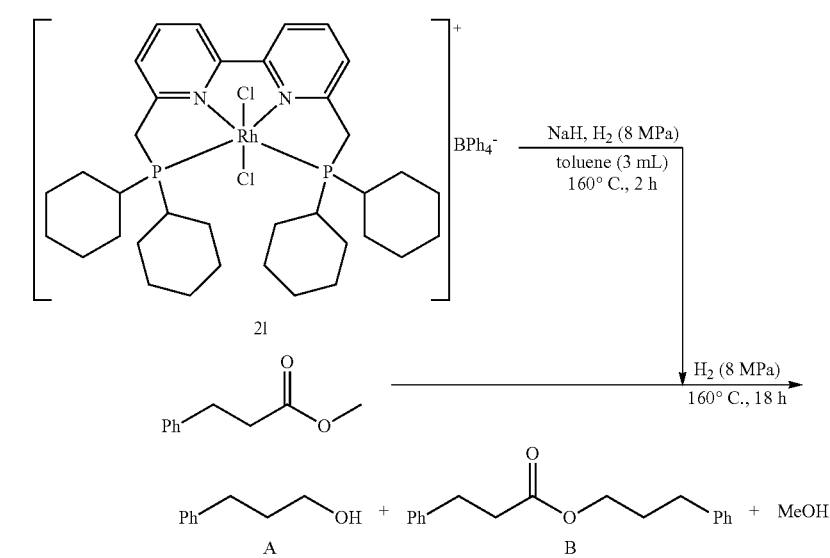

| Entry | Rh (mol %) | NaH (mol %) | A (%)[b] | B (%)[b] |
|---|---|---|---|---|
| 1 | 1 | 6 | — | — |
| 2 | 2 | 12 | 30 | 20 |
| 3[c] | 2 | 12 | 19 | 17 |

[a]All reactions were performed using ester (0.5 mmol, 79 μl).

[b]Crude reaction product was subjected to $^1$H NMR measurement using mesitylene as an internal standard substance.

[c]Reaction was performed for 24 hours at 160° C. without preactivation of catalyst.

(2) Reaction using Rhodium(I)Complex (Compound 2m)

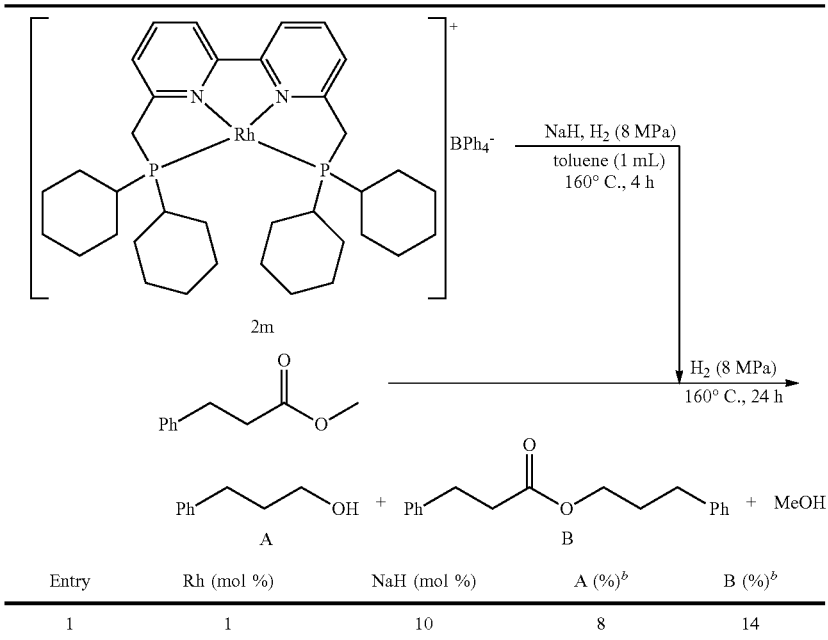

| Entry | Rh (mol %) | NaH (mol %) | A (%)[b] | B (%)[b] |
|---|---|---|---|---|
| 1 | 1 | 10 | 8 | 14 |

[a]All reactions were performed using ester (0.5 mmol, 79 µl).
[b]Crude reaction product was subjected to ¹H NMR measurement using mesitylene as an internal standard substance.

F. Iridium Complex

Example F1

(Synthesis of Compound 2n: Ir(I)PCY2)

A tetraphenyl borate 6,6'-bis((dicyclohexyl phosphino)methyl)-2,2' bipyridine-iridium complex was obtained as follows. The reaction scheme is shown below.

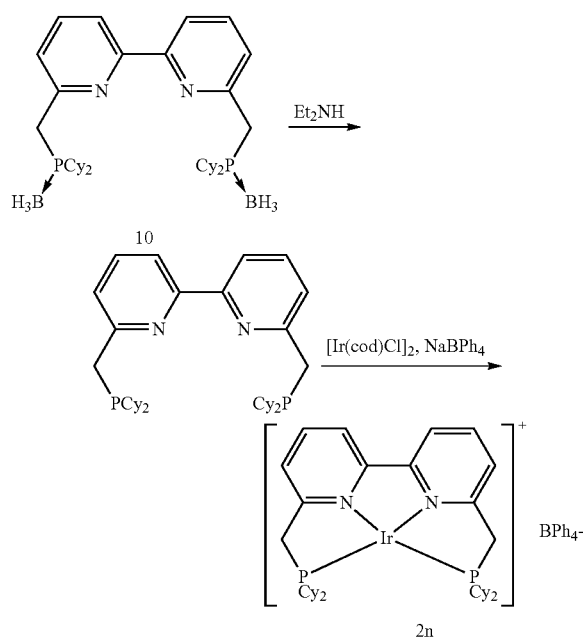

A 6,6'-bis((dicyclohexyl phosphino)methyl)-2,2'-bipyridine-diborane complex (60.4 mg, 0.10 mmol), diethylamine (5 mL), and THF (5 mL) were placed in a 100-mL Young-Schlenk container that had been dried and substituted with argon gas. Thereafter, the Schlenk container was placed in an oil bath, and heated to 70° C. while stirring the components in the Young-Schlenk container, thereby causing a reaction. The heating was stopped after 48 hours. Subsequently, the diethylamine and THF in the reaction mixture restored to room temperature (25° C.) were removed after collection with a liquid nitrogen trap under reduced pressure (0.1 to 2 mmHg).

After sufficiently removing the diethylamine, chloro(1,5-cyclooctadiene)iridium(I)dimer (33.6 mg, 0.05 mmol) and dehydrated methanol (5 mL) were added while introducing argon gas into the Schlenk container, and the mixture was heated to 75° C. using an oil bath, thereby causing a reaction. Six hours later, the heating was stopped, and the precipitates in the mixed solution were removed by Celite filtration in an argon atmosphere.

Sodium tetraphenyl borate (68.4 mg, 0.2 mmol) and dehydrated methanol (5 mL) were placed in another Schlenk container. The mixture was stirred at room temperature (25° C.) for 30 minutes to be dissolved. The solution was added to the above reacted solution while introducing argon gas, thereby immediately generating yellow precipitates. After an hour of stirring, the generated yellow precipitates were collected by filtration in an argon atmosphere, thereby obtaining 55.5 mg (0.051 mmol, 51%) of an iridium(I) complex (Compound 2n).

The spectral data of the iridium(I)complex (Compound 2n) is shown below.

¹H NMR (600 MHz, DMSO-d6): δ 8.47 (d, 2H, J=8.2 Hz, $C_{10}H_6N_2$), 8.26 (t, 2H, J=8.2 Hz, $C_{10}H_6N_2$), 7.89 (d, 2H, J=8.3 Hz, $C_{10}H_6N_2$), 7.17 (m, 8H, $B(C_6H_5)_4$), 6.97 (m, 8H, $B(C_6H_5)_4$), 6.78 (m, 4H, $B(C_6H_5)_4$), 4.11 (m, 2H, $PCH_2$), 3.86 (m, 2H, $PCH_2$), 0.97-2.46 (m, 44H, $C_6H_{11}$). ¹³C NMR (151 MHz, DMSO-d6): δ 161.3, 155.7, 135.4, 129.1, 128.8, 127.3, 126.5, 125.2, 121.3, 115.1, 34.5, 27.7, 27.1, 26.5, 25.4. $^{31}$P NMR (243 MHz, DMSO-d6): δ 19.6.

Example F2

(Synthesis of Compound 2o: Ir(I)PPH2)

A tetraphenyl borate 6,6'-bis((diphenyl phosphino)methyl)-2,2' bipyridine-iridium complex was obtained as follows. The reaction scheme is shown below.

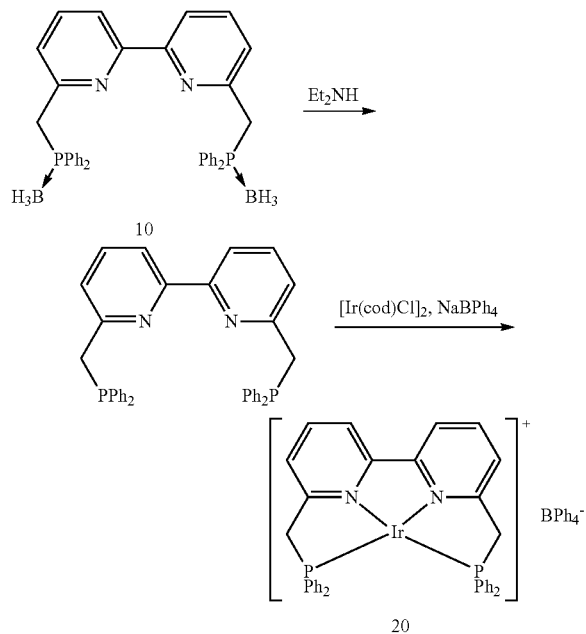

A 6,6'-bis((diphenyl phosphino)methyl)-2,2'-bipyridine-diborane complex (116.1 mg, 0.20 mmol), diethylamine (10 mL), and THF (10 mL) were placed in a 100-mL Young-Schlenk container that had been dried and substituted with argon gas. Thereafter, the Schlenk container was placed in an oil bath, and heated to 75° C. while stirring the components in the Schlenk container, thereby causing a reaction. The heating was stopped after 48 hours. Subsequently, the diethylamine and THF in the reaction mixture restored to room temperature (25° C.) were removed after collection with a liquid nitrogen trap under reduced pressure (0.1 to 2 mmHg).

After sufficiently removing the diethylamine, chloro(1,5-cyclooctadiene)iridium(I)dimer (67.2 mg, 0.10 mmol) and dehydrated methanol (12 mL) were added while introducing argon gas into the Schlenk container, and the mixture was heated to 75° C. using an oil bath, thereby causing a reaction. Seven hours later, the heating was stopped, and the precipitates in the mixed solution were removed by Celite filtration in an argon atmosphere.

Sodium tetraphenyl borate (136.9 mg, 0.4 mmol) and dehydrated methanol (5 mL) were placed in another Schlenk container. The mixture was stirred at room temperature (25° C.) for 30 minutes, causing it to be dissolved. The solution was added to the above reacted solution while introducing argon gas, thereby immediately generating yellow precipitates. After an hour of stirring, the generated yellow precipitates were collected by filtration in an argon atmosphere, thereby obtaining 91.5 mg (0.086 mmol, 43%) of an iridium (I)complex (Compound 2o).

The spectral data of the iridium(I)complex (Compound 2o) is shown below.

$^{1}$H NMR (600 MHz, DMSO-d6): δ 8.62 (d, 2H, J=8.2 Hz, $C_{10}H_6N_2$), 8.37 (t, 2H, J=7.6 Hz, $C_{10}H_6N_2$), 8.07 (d, 2H, J=7.6 Hz, $C_{10}H_6N_2$), 7.66-7.29 (m, 20H, $C_6H_5$), 7.17 (br, 8H, $B(C_6H_5)_4$), 6.92 (t, 8H, J=6.9 Hz, $B(C_6H_5)_4$), 6.78 (t, 4H, J=6.9 Hz, $B(C_6H_5)_4$), 5.10 (m, 2H, $PCH_2$), 4.83 (m, 2H, $PCH_2$). $^{13}$C NMR (151 MHz, DMSO-d6): δ 163.8, 163.5, 163.2, 162.9, 160.9, 156.1, 140.2, 135.5, 133.3, 132.0, 131.4, 129.3, 128.9, 128.5, 128.3, 127.4, 126.7, 125.3, 123.2, 121.5, 115.2. $^{31}$P NMR (243 MHz, DMSO-d6): δ 5.1.

Reaction Example F1

Reduction of Carboxylic Acid

A reduction reaction using molecular hydrogen of formic acid was performed as follows. The reaction scheme is shown below.

[Chem. 41]

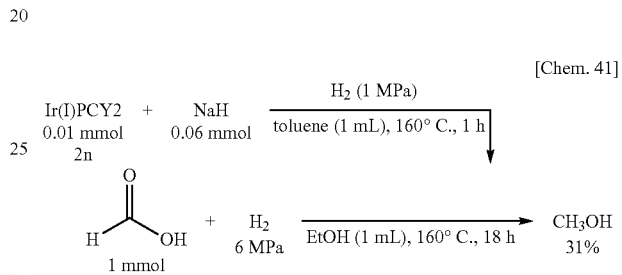

A stirrer, an iridium(I)complex (Compound 2n) (10.9 mg, 0.01 mmol), and sodium hydride (1.4 mg, 0.06 mmol) were placed in a dried fluororesin tube (30 mL). The tube containing the mixture was rapidly inserted into an autoclave. Thereafter, dehydrated toluene (1 mL) was added to the mixture in the tube while introducing argon gas into the autoclave; then, the autoclave was rapidly hermetically sealed. Hydrogen gas was introduced into this autoclave from a hydrogen compressed gas cylinder connected via a stainless-steel pipe, thereby substituting the inside of the autoclave with hydrogen gas. More specifically, 1-MPa hydrogen gas pressure was applied inside the autoclave, and then the hydrogen gas pressure was removed through a leak valve. This operation was repeated three times. Finally, the hydrogen gas pressure inside the autoclave was set to 1 MPa, and the mixture was stirred for an hour using a constant-temperature bath at 160° C. Thereafter, the autoclave was cooled by being immersed in icy bath. The valve of the autoclave restored to substantially room temperature was opened to release the hydrogen gas into the air. While immediately introducing argon gas into the autoclave, formic acid (37.7 mL, 1 mmol) and ethanol (1 mL) were added to the mixture in the tube; then, the autoclave was rapidly hermetically sealed. Hydrogen gas was introduced into the autoclave in the same manner as above, thereby substituting the inside of the autoclave with hydrogen gas. Finally, the hydrogen gas pressure inside the autoclave was set to 6 MPa, and the mixture was stirred for 18 hours using a constant-temperature bath at 160° C.

After the reaction was completed, the autoclave was cooled to substantially room temperature by being immersed in an icy bath. Then, the leak valve of the autoclave was opened and the hydrogen gas inside the autoclave was released into the air. Subsequently, the tube was taken out of the autoclave, thereby obtaining a reaction product (solution). An internal standard substance (mesitylene) was added to the solution. Based on the integration value of the hydrogen atom amount of the internal standard substance, the yield of the reaction product was calculated. The results showed that the yield of the methanol was 31%.

Reaction Example F2

Reduction of Carboxylic Acid

A reduction reaction using molecular hydrogen of succinic acid was performed as follows. The reaction scheme is shown below.

[Chem. 42]

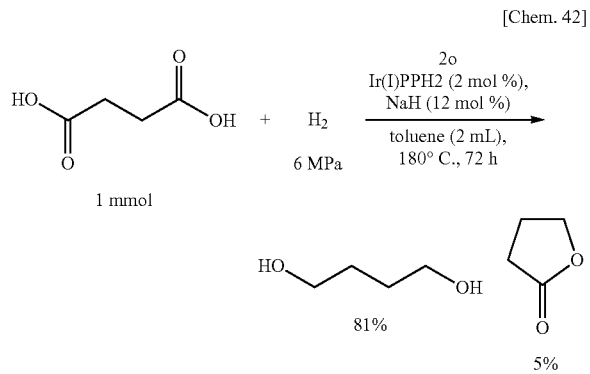

A stirrer, an iridium(I)complex (Compound 2o) (21.3 mg, 0.02 mmol), sodium hydride (2.8 mg, 0.12 mmol), and succinic acid (118.1 mg, 1 mmol) were placed in a dried fluororesin tube (30 mL). The tube containing the mixture was rapidly inserted into an autoclave. Thereafter, dehydrated toluene (2 mL) was added to the mixture in the tube while introducing argon gas into the autoclave; then, the autoclave was rapidly hermetically sealed. Hydrogen gas was introduced into the autoclave from a hydrogen compressed gas cylinder connected via a stainless-steel pipe, thereby substituting the inside of the autoclave with hydrogen gas. More specifically, 1-MPa hydrogen gas pressure was applied inside the autoclave, and then the hydrogen gas pressure was removed through a leak valve. This operation was repeated three times. Finally, the hydrogen gas pressure inside the autoclave was set to 6 MPa, and the mixture was stirred for 72 hours using a constant-temperature bath at 180° C.

After the reaction was completed, the autoclave was cooled to substantially room temperature by being immersed in an icy bath. Then, the leak valve of the autoclave was opened and the hydrogen gas inside the autoclave was released into the air. Subsequently, the tube was taken out of the autoclave, thereby obtaining a reaction product (solution). An internal standard substance (mesitylene) was added to the solution. Based on the integration value of the hydrogen atom amount of the internal standard substance, the yield of the reaction product was calculated. 1,4-butane diol and γ-butyrolactone were obtained at yields of 81% and 5%, respectively.

Reaction Example F3

Reduction of Carboxylic Acid

A reduction reaction using molecular hydrogen of succinic acid was performed as follows. The reaction scheme is shown below.

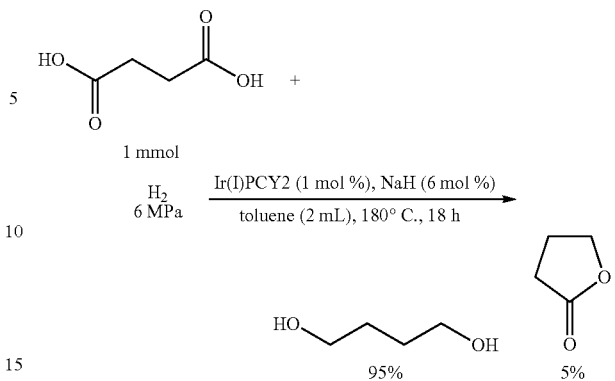

A stirrer, an iridium(I)complex (Compound 2n) (10.9 mg, 0.01 mmol), sodium hydride (1.4 mg, 0.06 mmol), and succinic acid (118.1 mg, 1 mmol) were placed in a dried fluororesin tube (30 mL). The tube containing the mixture was rapidly inserted into an autoclave. Thereafter, dehydrated toluene (2 mL) was added to the mixture in the tube while introducing argon gas into the autoclave; then, the autoclave was rapidly hermetically sealed. Hydrogen gas was introduced into the autoclave from a hydrogen compressed gas cylinder connected via a stainless-steel pipe, thereby substituting the inside of the autoclave with hydrogen gas. More specifically, 1-MPa hydrogen gas pressure was applied inside the autoclave, and then the hydrogen gas pressure was removed through a leak valve. This operation was repeated three times. Finally, the hydrogen gas pressure inside the autoclave was set to 6 MPa, and the mixture was stirred for 18 hours using a constant-temperature bath at 180° C.

After the reaction was completed, the autoclave was cooled to substantially room temperature by being immersed in an icy bath. Then, the leak valve of the autoclave was opened and the hydrogen gas inside the autoclave was released into the air. Subsequently, the tube was taken out of the autoclave, thereby obtaining a reaction product (solution). An internal standard substance (mesitylene) was added to the solution. Based on the integration value of the hydrogen atom amount of the internal standard substance, the yield of the reaction product was calculated. 1,4-butane diol and γ-butyrolactone were obtained at yields of 95% and 5%, respectively.

G. Platinum Complex

Example G1

(Synthesis of Compound 2p: Pt(II)PCY2)

A bis tetraphenyl borate 6,6'-bis((dicyclohexyl phosphino)methyl)-2,2' bipyridine-platinum complex was obtained as follows. The reaction scheme is shown below.

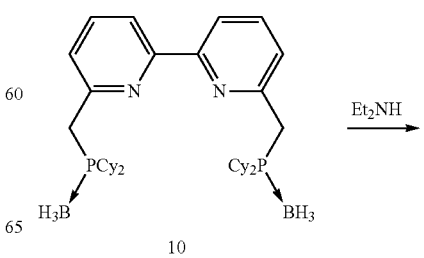

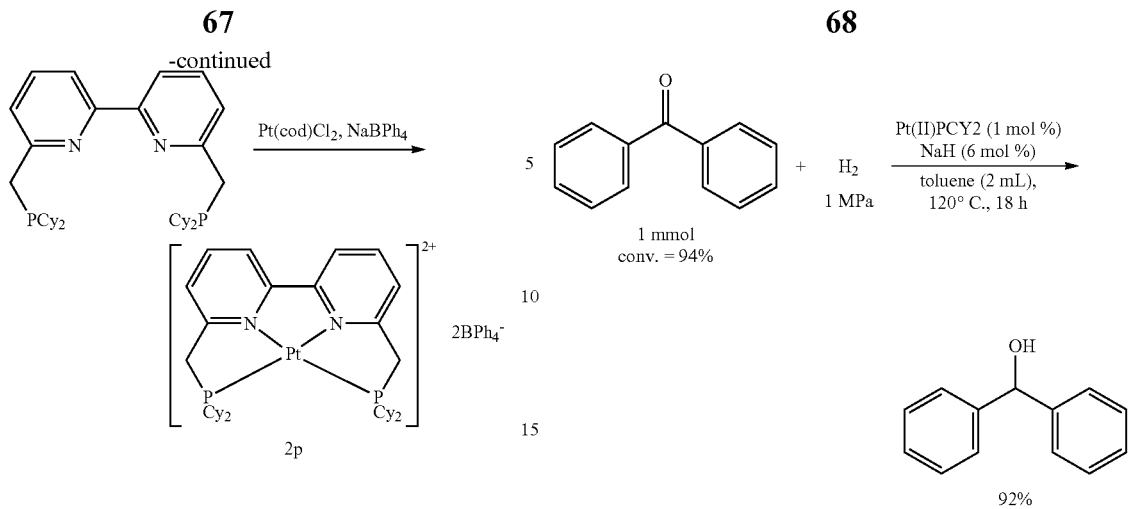

A 6,6'-bis((dicyclohexyl phosphino)methyl)-2,2'-bipyridine-diborane complex (60.4 mg, 0.10 mmol), diethylamine (5 mL), and THF (5 mL) were placed in a 100-mL Young-Schlenk container that had been dried and substituted with argon gas. Thereafter, the Schlenk container was placed in an oil bath, and heated to 70° C. while stirring the components in the Schlenk container, thereby causing a reaction. The heating was stopped after 48 hours. Subsequently, the diethylamine and THF in the reaction mixture restored to room temperature (25° C.) were removed after collection with a liquid nitrogen trap under reduced pressure (0.1 to 2 mmHg).

After sufficiently removing the diethylamine, dichloro(1,5-cyclooctadiene)platinum(II) (37.4 mg, 0.10 mmol) and dehydrated methanol (5 mL) were added while introducing argon gas into the Schlenk container, and the mixture was heated to 75° C. using an oil bath, thereby causing a reaction. Six hours later, the heating was stopped, and the precipitates in the mixed solution were removed by Celite filtration in an argon atmosphere.

Sodium tetraphenyl borate (68.4 mg, 0.2 mmol) and dehydrated methanol (5 mL) were placed in another Schlenk container. The mixture was stirred at room temperature (25° C.) for 30 minutes, causing it to be dissolved. The solution was added to the above reacted solution while introducing argon gas, thereby immediately generating pale yellow precipitates. After an hour of stirring, the generated yellow precipitates were collected by filtration in an argon atmosphere, thereby obtaining 63.5 mg (0.045 mmol, 45%) of a platinum(II)complex (Compound 2p).

The spectral data of the platinum(II)complex (Compound 2p) is shown below.

$^1$H NMR (500 MHz, CD$_3$CN): δ 8.28 (t, 2H, J=8.0 Hz, C$_{10}$H$_6$N$_2$), 8.07 (d, 2H, J=8.0 Hz, C$_{10}$H$_6$N$_2$), 7.89 (d, 2H, J=8.1 Hz, C$_{10}$H$_6$N$_2$), 7.24 (br, 16H, B(C$_6$H$_5$)$_4$), 6.96 (t, 16H, J=7.5 Hz, B(C$_6$H$_5$)$_4$), 6.81 (t, 8H, J=7.5 Hz, B(C$_6$H$_5$)$_4$), 4.05 (m, 4H, PCH$_2$), 1.23-2.36 (m, 44H, C$_6$H$_{11}$). $^{31}$P NMR (179 MHz, CD$_3$CN): δ 35.3 (t, J=1556 Hz).

Reaction Example G1

Reduction of Ketone

A reduction reaction using molecular hydrogen of ketone was performed as follows. The reaction scheme is shown below.

A stirrer, Pt(II)PCY2 (14.1 mg, 0.01 mmol), sodium hydride (2.4 mg, 0.1 mmol), and benzophenone (182.2 mg, 1.0 mmol) were placed in a dried fluororesin tube (30 mL). The tube containing the mixture was rapidly inserted into an autoclave. Thereafter, dehydrated toluene (2 mL) was added to the mixture in the tube while introducing argon gas into the autoclave; then, the autoclave was rapidly hermetically sealed. Hydrogen gas was introduced into the autoclave from a hydrogen compressed gas cylinder connected via a stainless-steel pipe, thereby substituting the inside of the autoclave with hydrogen gas. More specifically, 1-MPa hydrogen gas pressure was applied inside the autoclave, and then the hydrogen gas pressure was removed through a leak valve. This operation was repeated three times. Finally, the hydrogen gas pressure inside the autoclave was set to 1 MPa, and a reaction was performed for 18 hours using a constant-temperature bath at 120° C.

After the reaction was completed, the autoclave was cooled to substantially room temperature by being immersed in an icy bath. Then, the leak valve of the autoclave was opened and the hydrogen gas inside the autoclave was released into the air. Subsequently, the tube was taken out of the autoclave, thereby obtaining a reaction product (solution). A hydrogen chloride-methanol solution (2.0 M, 50 μL, 0.1 mmol) was added to this solution to neutralize the solution. Thereafter, an internal standard substance (N,N-dimethyl formamide) was added to the solution. Based on the integration value of the hydrogen atom amount of the internal standard substance, the yield of the reaction product was calculated. The results showed that the yield of diphenyl methanol was 92%.

H. Palladium Complex

Example H$_1$ (Synthesis of Compound 2q: Pd(II)PCY2)

bis tetraphenyl borate 6,6'-bis((dicyclohexyl phosphino)methyl)-2,2' bipyridine-palladium complex was obtained as follows. The reaction scheme is shown below.

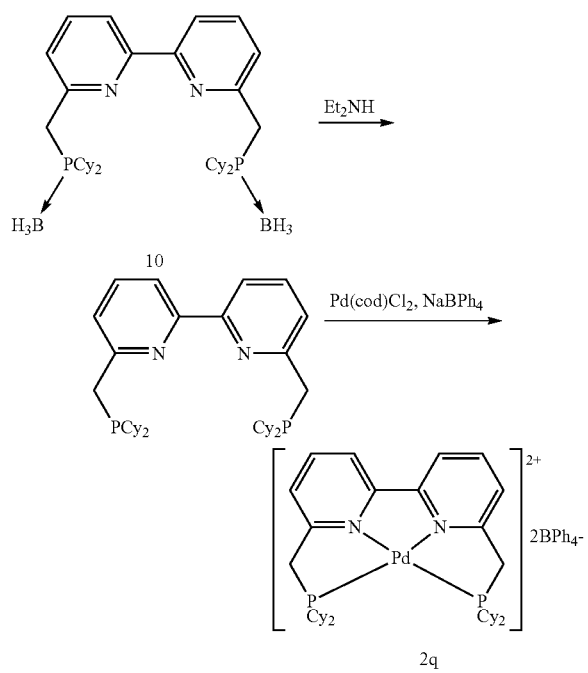

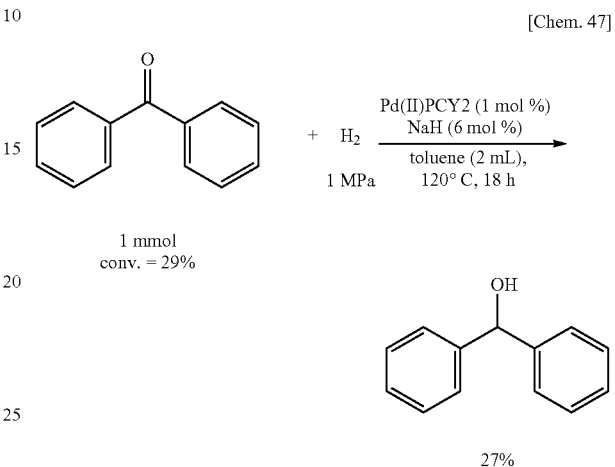

Reaction Example H₁

Reduction of Ketone

A reduction reaction using molecular hydrogen of ketone was performed as follows. The reaction scheme is shown below.

A 6,6'-bis((dicyclohexyl phosphino)methyl)-2,2'-bipyridine-diborane complex (60.4 mg, 0.10 mmol), diethylamine (5 mL), and THF (5 mL) were placed in a 100-mL Young-Schlenk container that had been dried and substituted with argon gas. Thereafter, the Schlenk container was placed in an oil bath, and heated to 70° C. while stirring the components in the Schlenk container, thereby causing a reaction. The heating was stopped after 48 hours. Subsequently, the diethylamine and THF in the reaction mixture restored to room temperature (25° C.) were removed after collection with a liquid nitrogen trap under reduced pressure (0.1 to 2 mmHg).

After sufficiently removing the diethylamine, dichloro(1,5-cyclooctadiene)palladium(II) (28.6 mg, 0.10 mmol) and dehydrated methanol (7 mL) were added while introducing argon gas into the Schlenk container, and the mixture was heated to 75° C. using an oil bath, thereby causing a reaction. Fourteen hours later, the heating was stopped, and the precipitates in the mixed solution were removed by Celite filtration in an argon atmosphere.

Sodium tetraphenyl borate (68.4 mg, 0.2 mmol) and dehydrated methanol (5 mL) were placed in another Schlenk container. The mixture was stirred at room temperature (25° C.) for 30 minutes, causing it to be dissolved. The solution was added to the above reacted solution while introducing argon gas, thereby immediately generating pale yellowish-green precipitates. After an hour of stirring, the generated pale yellowish-green precipitates were collected by filtration in an argon atmosphere, thereby obtaining 93.8 mg (0.071 mmol, 71%) of a palladium(II)complex (Compound 2q).

The spectral data of the palladium(II)complex (Compound 2q) is shown below.

$^1$H NMR (600 MHz, CD$_3$CN): δ 8.24 (t, 2H, J=7.6 Hz, C$_{10}$H$_6$N$_2$), 8.13 (d, 2H, J=8.3 Hz, C$_{10}$H$_6$N$_2$), 7.80 (d, 2H, J=7.6 Hz, C$_{10}$H$_6$N$_2$), 7.27 (br, 16H, B(C$_6$H$_5$)$_4$), 6.99 (t, 16H, J=6.9 Hz, B(C$_6$H$_5$)$_4$), 6.84 (t, 8H, J=6.8 Hz, B(C$_6$H$_5$)$_4$), 4.13 (m, 4H, PCH$_2$), 1.23-2.34 (m, 44H, C$_6$H$_{11}$). $^{31}$P NMR (179 MHz, CD$_3$CN): δ 61.9.

A stirrer, Pd(II)PCY2 (13.2 mg, 0.01 mmol), sodium hydride (2.4 mg, 0.1 mmol), and benzophenone (182.2 mg, 1.0 mmol) were placed in a dried fluororesin tube (30 mL). The tube containing the mixture was rapidly inserted into an autoclave. Thereafter, dehydrated toluene (2 mL) was added to the mixture in the tube while introducing argon gas into the autoclave; then, the autoclave was rapidly hermetically sealed. Hydrogen gas was introduced into the autoclave from a hydrogen compressed gas cylinder connected via a stainless-steel pipe, thereby substituting the inside of the autoclave with hydrogen gas. More specifically, 1-MPa hydrogen gas pressure was applied inside the autoclave, and then the hydrogen gas pressure was removed through a leak valve. This operation was repeated three times. Finally, the hydrogen gas pressure inside the autoclave was set to 1 MPa, and a reaction was performed for 18 hours using a constant-temperature bath at 120° C.

After the reaction was completed, the autoclave was cooled to substantially room temperature by being immersed in an icy bath. Then, the leak valve of the autoclave was opened and the hydrogen gas inside the autoclave was released into the air. Subsequently, the tube was taken out of the autoclave, thereby obtaining a reaction product (solution). A hydrogen chloride-methanol solution (2.0 M, 50 μL, 0.1 mmol) was added to this solution to neutralize the solution. Thereafter, an internal standard substance (N,N-dimethyl formamide) was added to the solution. Based on the integration value of the hydrogen atom amount of the internal standard substance, the yield of the reaction product was calculated. The results showed that the yield of diphenyl methanol was 27%.

INDUSTRIAL APPLICABILITY

The complex of the present invention, which is formed of a tetradentate ligand and a metal, such as ruthenium, is capable of efficiently catalyzing a hydrogen transfer reaction. Therefore, the complex of the present invention is significantly useful as a catalyst for hydrogen transfer reaction.

The invention claimed is:
1. A compound represented by Formula (1a):

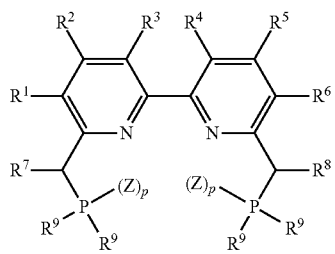

wherein, $R^1$ to $R^8$ are the same or different, and each represents a hydrogen atom, an alkyl group, alkoxy group, or aryl group; or wherein, $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group;
$R^9$ are the same or different, and each represents an alkyl group, cycloalkyl group, or aryl group;
Z are the same or different, and each represents a phosphorus atom-protecting group;
p each represents 1;
the formula excluding a case where $R^1$, $R^2$, and $R^5$ to $R^8$ are hydrogen atoms, $R^3$ and $R^4$ are bonded to form a group represented by —CH=CH—, and $R^9$ is a t-butyl group.

2. A compound represented by Formula (2a):

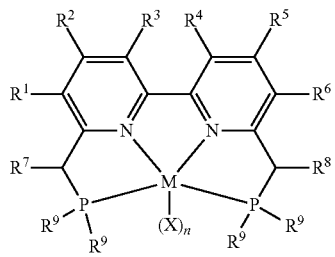

wherein, $R^1$ to $R^8$ are the same or different, and each represents a hydrogen atom, an alkyl group, alkoxy group, or aryl group; or wherein, $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group;
$R^9$ are the same or different, and each represents an alkyl group, cycloalkyl group, or aryl group;
M is nickel (Ni), cobalt (Co), iron (Fe), rhodium (Rh), iridium (Ir), platinum (Pt), palladium (Pd), gold (Au) or copper (Cu);
X is a ligand;
n is 0, 1 or 2;
the formula excluding a case where $R^1$, $R^2$, and $R^5$ to $R^8$ are hydrogen atoms, $R^3$ and $R^4$ are bonded to form a group represented by CH=CH—, and $R^9$ is a t-butyl group.

3. A catalyst for dehydrogenation reaction, represented by Formula (2a):

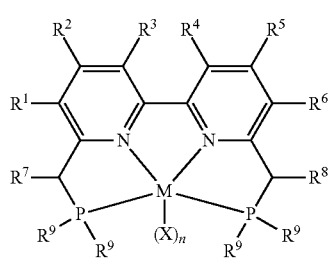

wherein, $R^1$ to $R^8$ are the same or different, and each represents a hydrogen atom, alkyl group, alkoxy group, or aryl group; or wherein, $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group;
$R^9$ are the same or different, and each represents an alkyl group, cyclo alkyl group, or aryl group;
M is nickel (Ni), cobalt (Co), iron (Fe), rhodium (Rh), iridium (Ir), platinum (Pt), palladium (Pd), gold (Au) or copper (Cu);
X is a ligand;
n is 0, 1 or 2;
the formula excluding a case where $R^1$, $R^2$, and $R^5$ to $R^8$ are hydrogen atoms, $R^3$ and $R^4$ are bonded to form a group represented by CH=CH—, and $R^9$ is a t-butyl group.

4. A method for producing a hydrogen transfer reaction product, comprising the step of:
subjecting an organic compound to a dehydrogenation reaction (oxidation reaction) in the presence of the compound according to claim 2.

5. A catalyst for hydrogenation reaction, represented by Formula (2):

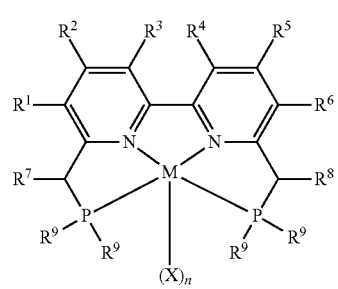

wherein, $R^1$ to $R^8$ are the same or different, and each represents a hydrogen atom, alkyl group, alkoxy group, or aryl group; or wherein, $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group;
$R^9$ are the same or different, and each represents an alkyl group, cycloalkyl group, or aryl group;
M is ruthenium (Ru), nickel (Ni), cobalt (Co), iron (Fe), rhodium (Rh), iridium (Ir), platinum (Pt), palladium (Pd), gold (Au) or copper (Cu);
X is a ligand; and
n is 0, 1 or 2:
the formula excluding a case where $R^1$, $R^2$, and $R^5$ to $R^8$ are hydrogen atoms, $R^3$ and $R^4$ are bonded to form a group represented by —CH=CH—, and $R^9$ is a t-butyl group.

6. A method for producing a hydrogen transfer reaction product, comprising the step of:
   subjecting an organic compound to a hydrogenation reaction in the presence of the catalyst for hydrogenation reaction according to claim 5.

7. A compound represented by Formula (2a):

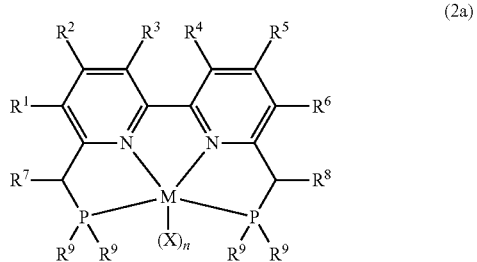

(2a)

wherein, $R^1$ to $R^8$ are the same or different, and each represents a hydrogen atom, alkyl group, alkoxy group, or aryl group; or wherein, $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group;

$R^9$ are the same or different, and each represents an alkyl group, cyclo alkyl group, or aryl group;

M is ruthenium (Ru), nickel (Ni), cobalt (Co), iron (Fe), rhodium (Rh), iridium (Ir), platinum (Pt), palladium (Pd), gold (Au) or copper (Cu);

X is a ligand;

n is 0, 1 or 2;

the formula excluding a case where $R^1$, $R^2$, and $R^5$ to $R^8$ are hydrogen atoms, $R^3$ and $R^4$ are bonded to form a group represented by —CH=CH—, and $R^9$ is a t-butyl group.

8. The compound according to claim 7, wherein, in Formula (2a), $R^9$ are the same or different, and each represents a linear or branched $C_{1-10}$ alkyl group, or $C_{3-8}$ cycloalkyl group.

9. A catalyst for dehydrogenation reaction, represented by Formula (2a):

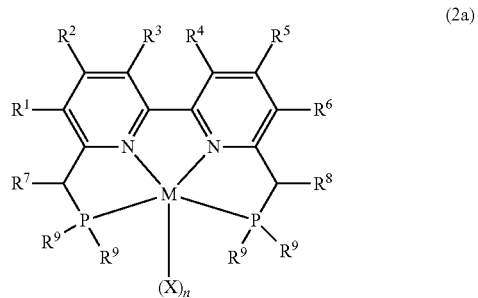

(2a)

wherein, $R^1$ to $R^8$ are the same or different, and each represents a hydrogen atom, alkyl group, alkoxy group, or aryl group; or wherein, $R^1$ and $R^2$, $R^2$ and $R^3$, $R^3$ and $R^4$, $R^4$ and $R^5$, and $R^5$ and $R^6$ are respectively bonded to each other to form a bivalent hydrocarbon group;

$R^9$ are the same or different, and each represents an alkyl group, cycloalkyl group, or aryl group;

M is ruthenium (Ru), nickel (Ni), cobalt (Co), iron (Fe), rhodium (Rh), iridium (Ir), platinum (Pt), palladium (Pd), gold (Au) or copper (Cu);

X is a ligand;

n is 0, 1 or 2;

the formula excluding a case where $R^1$, $R^2$, and $R^5$ to $R^8$ are hydrogen atoms, $R^3$ and $R^4$ are bonded to form a group represented by —CH=CH—, and $R^9$ is a t-butyl group.

10. A method for producing a dehydrogenation reaction product, comprising the step of:
   subjecting an organic compound to a dehydrogenation reaction in the presence of the catalyst for dehydrogenation reaction according to claim 9.

* * * * *